US007566808B2

(12) United States Patent
Rando

(10) Patent No.: US 7,566,808 B2
(45) Date of Patent: Jul. 28, 2009

(54) MANAGEMENT OF OPHTHALMOLOGIC DISORDERS, INCLUDING MACULAR DEGENERATION

(75) Inventor: Robert R. Rando, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 175 days.

(21) Appl. No.: 11/199,594

(22) Filed: Aug. 8, 2005

(65) Prior Publication Data

US 2006/0069078 A1    Mar. 30, 2006

Related U.S. Application Data

(63) Continuation-in-part of application No. PCT/US2005/004990, filed on Feb. 17, 2005.

(60) Provisional application No. 60/545,456, filed on Feb. 17, 2004, provisional application No. 60/567,604, filed on May 3, 2004, provisional application No. 60/578,324, filed on Jun. 9, 2004.

(51) Int. Cl.
C07C 49/20 (2006.01)

(52) U.S. Cl. ..................................... 568/417

(58) Field of Classification Search ................... 568/417
See application file for complete search history.

(56) References Cited

U.S. PATENT DOCUMENTS

| 2,654,722 | A | 10/1953 | Young et al. |
| 3,726,919 | A | 4/1973 | Wooldridge et al. |
| 3,780,103 | A | 12/1973 | Knell |
| 4,108,880 | A | 8/1978 | Gander et al. |
| 4,215,215 | A | 7/1980 | Bollag et al. |
| 4,310,546 | A | 1/1982 | Gander |
| 4,743,400 | A | 5/1988 | Maryanoff |
| 5,661,138 | A | 8/1997 | Peterson et al. |
| 2003/0032078 | A1 | 2/2003 | Travis |
| 2004/0034242 | A1 | 2/2004 | Yang |

FOREIGN PATENT DOCUMENTS

| DE | EP 1354594 A1 | 10/2003 |
| EA | 0 508 842 | 8/1994 |
| FR | 2 212 135 | 7/1974 |
| FR | 2 293 193 | 7/1976 |
| GB | 1 283 887 | 8/1972 |
| WO | WO 99/58126 | 11/1999 |
| WO | WO 99/58216 | 11/1999 |
| WO | WO-02/096857 | 12/2002 |
| WO | WO 2004/082622 A2 | 9/2004 |
| WO | WO-2005/092314 | 10/2005 |
| WO | WO 2006/007314 A1 | 1/2006 |
| WO | WO 2006/047475 | 5/2006 |
| WO | WO 2006/063128 | 6/2006 |
| WO | WO 2006/063128 A2 | 6/2006 |

OTHER PUBLICATIONS

STN Abstract of Journal of Economic Entomology (1972), 65(6), 1644-7.*
CAPLUS abstract of: Kim et al., Tetrahedron Letters (1990), 31(20), 2901-4.*
Allikmets, R. et al., "Mutation of the Stargardt Disease Gene (ABCR) in Age-Related Macular Degeneration"), *Science*, 277:1805-1807 (Sep. 19, 1997).
Allikmets, R., "Simple and Complex ABCR: Genetic Predisposition to Retinal Disease", *Am. J. Hum. Genet.*, 67:793-799 (2000).
Ambati, J. et al., "An animal model of age-related macular degeneration in senescent Ccl-2- or Ccr-2-deficient mice", *Nature Medicine*, 9(11):1390-1397 (Nov. 2003).
Baglietto, L. et al., "Ocular Effects of Fenretinide, a Vitamin A Analog, in a Chemoprevention Trial of Bladder Cancer", *Cancer Detection and Prevention*, 24(4):369-375 (2000).
Ban, Y. et al., "Differential regulation of tight junction permeability during development of the retinal pigment epithelium", *Am. J. Physiol. Cell Physiol.*, 279:C744-C750 (2000).
Berni, B. et al., "Retiniods: in vitro interaction with retinol-binding protein and influence on plasma retinol", *FASEB Journal*, 7:1179-1184 (Sep. 1993).
Bernstein, P. S. et al., "The Specific Inhibition of 11-*cis*—Retinyl Palmitate Formation in the Frog Eye by Diaminophenoxypentane, an Inhibitor of Rhodopsin Regeneration", *Vision Res.*, 25(6):741-748 (1985).
Bernstein, P. S. et al., "Short-circuiting the visual cycle with retinotoxic aromatic amines", *Proc. Natl. Acad. Sci. USA*, 83:1632-1635 (Mar. 1986).
Bernstein, P. S. et al., "Mechanism of Action of Aromatic Amines That Short-Circuit the Visual Cycle", *Biochemistry*, 25:3370-3377 (1986).
Camerini, T. et al., "Safety of the Synthetic Retinoid Fenretinide: Long-Term Results From a Controlled Clinical Trial for the Prevention of Contralateral Breast Cancer", *Journal of Clinical Oncology*, 19(6):1664-1670 (Mar. 15, 2001).
Caruso, R. C. et al., "Effects of Fenretinide (4-HPR) on Dark Adaptation", *Arch. Ophthalmol*, 116:759-763 (Jun. 1998).
Conley, B. et al., "Pilot Trial of the Safety, Tolerability, and Retinoid Levels of N-(4-hydroxyphenyl) Retinamide in Combination With Tamoxifen in Patients at High Risk for Developing Invasive Breast Cancer", *Journal of Clinical Oncology*, 18(2):275-283 (Jan. 2000).

(Continued)

*Primary Examiner*—Kamal A Saeed
*Assistant Examiner*—Robert Havlin
(74) *Attorney, Agent, or Firm*—DeAnn F. Smith, Esq.; Foley Hoag LLP

(57) ABSTRACT

A drug may be used in the preparation of a medicament for the treatment or prevention of an ophthalmologic disorder, wherein the drug inihibits, antagonizes, or short-circuits the visual cycle at a step of the visual cycle that occurs outside a disc of a rod photoreceptor cell.

1 Claim, 23 Drawing Sheets

OTHER PUBLICATIONS

Darrow, R. A. et al., "Biochemical characterization of cell specific enzymes in light-exposed rat retinas: oxidative loss of all-trans retinol dehydrogenase activity", *Current Eye Research*, Wright State University, Dayton, OH 144-151 (Sep. 17, 1996).

Decensi, A. et al., "Effect of the Synthetic Retinoid Fenretinide on Dark Adaptation and the Ocular Surface", *Journal of the National Cancer Institute*, 86(2):105-110 (Jan. 19, 1994).

Decensi, A. et al., "Long-Term Effects of Fenretinide on Retinal Function", *European Journal of Cancer*, 33(1):80-84 (1997).

Dimitrov, N. V. et al., "Alteration of retinol-binding-protein concentrations by the synthetic retinoid fenretinide in healthy human subjects", *Am. J. Clin. Nutr.*, 51:1082-1087 (1990).

Fulton, B. S. et al., "Mechanism of Isomerization of 11-*cis*—Retinal in Lipid Dispersions by Aromatic Amines", *Biochemistry*, 26(1):110-114 (1987).

Garaventa, A. et al., "Phase I Trial and Pharmacokinetics of Fenretinide in Children with Neuroblastoma", *Clinical Cancer Research*, 9:2032-2039 (Jun. 2003).

Giner, J.-L. et al., "Novel Methyltransferase Activity Modifying the Carboxy Terminal Bis(geranylgeranyl)-Cys-Ala-Cys Structure of Small GTP-Binding Proteins", *Biochemistry*, 33:15116-15123 (1994).

Gollapallli, D. R. et al., "RPE65 Operates in the Vertebrate Visual Cycle by Stereospecifically Binding All-*trans*—Retinyl Esters", *Biochemistry*, 42:11824-11830 (2003).

Gollapalli, D. R. et al., "The specific binding of retinoic acid to RPE65 and approaches to the treatment of macular degeneration", *PNAS*, 101(27):10030-10035 (Jul. 6, 2004).

Holven, K. B. et al., "Secretion of N-(4-Hydroxyphenyl) Retinamide-Retinol-Binding Protein from Liver Parenchymal Cells: Evidence for Reduced Affinity of the Complex for Transthyretin", *Int. J. Cancer*, 71:654-659 (1997).

Jahng, W. J. et al., "A Cleavable Affinity Biotinylating Agent Reveals a Retinoid Binding Role for RPE65", *Biochemistry*, 42:6159-6168 (2003).

Kaiser-Kupfer, M. I. et al., "Abnormal Retinal Function Associated With Fenretinide, a Synthetic Retinoid", *Arch Opthalmol.*, 104:69-70 (Jan. 1986).

Kim, S. R. et al., "Rpe65 Leu450Met variant is associated with reduced levels of the retinal pigment epithelium lipofuscin flurorphores A2E and iso-A2E", *PNAS*, 101(32):11668-11672 (Aug. 10, 2004).

Kuksa, V. et al., "Retinoid cycle in the vertebrate retina: experimental approaches and mechanisms of isomerization", *Vision Research*, 43:2959-2981 (2003).

Law, W. C. et al., "The Molecular Basis of Retinoic Acid Induced Night Blindness", *Biochem. and Biophys. Research Comm.*, 161(2):825-829 (Jun. 15, 1989).

Le Doze, F. et al., "Pharmacokinetics of All-*Trans* Retinoic Acid, 13-*cis* Retinoic Acid, and Fenretinide in Plasma and Brain of Rat", *Drug Metabolism and Disposition*, 28(2):205-208 (2000).

Ma, Y.-T. et al., "Inhibitors of the Isoprenylated Protein Endoprotease", *Biochemistry*, 32:2386-2393 (1993).

Maiti, P. et al., "Specificity of Binding of all-*trans*-Retinyl Ester to RPE65", *Biochemistry*, 44:14463-14469 (2005).

Maiti, P. et al., "Small Molecule RPE65 Antagonists Limit the Visual Cycle and Prevent Lipofuscin Formation", *Biochemistry*, 45:852-860 (2006).

Malpeli, G. et al., "Interactions with retinol and retinoids of bovine cellular retinol-binding protein", *Eur. J. Biochem.* 229:486-493 (1995).

Malpeli, G. et al., "Retinoid binding to retinol-binding protein and the interference with the interaction with transthyretin", *Biochimica et Biophysica Acta*, 1294:48-54 (1996).

Marabotti, A. et al., "HINT Predictive Analysis of Binding Between Retinol Binding Protein and Hydrophobic Ligands", *Bioorganic and Medicinal Chemistry Letters*, 10:2129-2132 (2000).

Mata, N. L. et al., "Biosynthesis of a major lipofuscin fluorophore in mice and humans with *ABCR*-mediated retinal and macular degeneration", *PNAS*, 97(13):7154-7159 (Jun. 20, 2000).

Michaelides, M. et al., "The genetics of inherited macular dystrophies", *J. Med. Genet.*, 40:641-650 (2003).

Modiano, M. R. et al., "Ocular Toxic Effects of Fenretinide", *Brief Communications*, 82(12):1063 (Jun. 20, 1990).

Parish, C. A. et al., "Isoprenylation/Methylation of Proteins Enhances Membrane Association by a Hydrophobic Mechanism", *Biochemistry*, 35(26):8473-8477 (Jul. 2, 1996).

Parish, C. A. et al., "On the Mechanism of the Inhibition of Transduction Function by Farnesylcysteine Analogs", *Biochemistry*, 36:2686-2693 (1997).

Quadro, L. et al., "Impaired retinal function and vitamin A availability in mice lacking retinol-binding protein", *EMBO Journal*, 18(17):4633-4644 (1999).

Radu, R. A. et al., "Treatment with isotretinoin inhibits lipofuscin accumulation in a mouse model of recessive Stargardt's macular degeneration", *PNAS*, 100(8):4742-4747 (Apr. 15, 2003).

Radu, R. A. et al., "Isotretinoin treatment inhibits lipofuscin accumulation in a mouse model of recessive Stargardt's macular degeneration", *Novartis Foundation Symposium*, 255:51-67 (2004).

Rando, R. R., "Chemical biology of isoprenylation/methylation", *Biochem. Soc. Trans.*, 24:682-687 (Mar. 13, 1996).

Roberts D., "Fenretinide May Slow Vision Loss in Stargardt's Patients", *Macular Degeneration Support*, at www.mdsupport.org (Jul. 12, 2005).

Rotmensz, N. et al., "Long-Term Tolerability of Fenretinide (4-HPR) in Breast Cancer Patients", *Eur. J. Cancer*, 27(9):1127-1131 (1991).

Smith, J. E. et al., "Secretion of Vitamin A and Retinol-Binding Protein into Plasma Is Depressed in Rats by N-(4-Hydroxyphenyl) retinamide (Fenretinide)", *Nutrient Metabolism*, Nutrition Dept. Pennsylvania State Univ., University Park, PA et al., 1999-2009 (Jun. 22, 1992).

Sparrow, J. R., "Therapy for macular degeneration: Insights from acne", *PNAS*, 100(8):4353-4354 (Apr. 15, 2003).

Stone, E. M. et al., "Allelic variation in *ABCR* associated with Stargardt disease but not age-related macular degeneration", *Nature Genetics*, 20(4):328-329 (1998).

Sundaram, M. et al., "The Transfer of Retinol from Serum Retinol-binding Protein to Cellular Retinol-binding Protein Is Mediated by a Membrane Receptor", *Journ. of Biol. Chem.*, 273(6):3336-3342 (1988).

Thaller, C. et al., "Fenretinide Therapy in Prostate Cancer: Effects on Tissue and Serum Retinoid Concentration", *Journ. of Clin. Oncology*, 18(22):3804-3808 (Nov. 15, 2000).

Tsilou, E. et al., "RPE65, the Major Retinal Pigment Epithelium Microsomal Membrane Protein, Associates with Phospholipid Liposomes", *Arch. of Biochem. and Biophys.*, 346(1):21-27 (Oct. 1, 1997).

Veronesi, U. et al., "Randomized Trial of Fenretinide to Prevent Second Breast Malignancy in Women With Early Breast Cancer", *Journ. of the Natl. Cancer Inst.*, 91(21):1847-1856 (Nov. 3, 1999).

Veronesi, U. et al., "Fifteen-year results of a randomized phase III trial of fenretinide to prevent second breast cancer", *Annals of Oncology*, 1-7 (May 4, 2006).

Wang, H. M. et al., "Long term effects of diaminophenoxypentane in the rat retina: protection against light damage", *Current Eye Research*, Wright State Univ., Dayton, OH, 655-660 (Jun. 14, 1994).

Weng, J. et al., "Insights into the Function of Rim Protein in Photoreceptors and Etiology of Stargardt's Disease from the Phenotype in *abcr* Knockout Mice", *Cell*, 98:13-23 (Jul. 9, 1999).

Xu, Y. et al., "Inhibition of Capacitative $Ca^{2+}$ Entry into Cells by Farnesylcysteine Analogs", *Molecular Pharmacology*, 50:1495-1501 (1996).

Xue, L. et al., "A Palmitoylation Switch Mechanism in the Regulation of the Visual Cycle", *Cell*, 117:761-771 (Jun. 11, 2004).

Yang, Q. et al., "Serum retinol binding protein 4 contributes to insuling resistance in obesity and type 2 diabetes", *Nature*, 436(21):356-362 (2005).

Zanotti, G. et al., "Crystallographic Studies on Complexes between Retinoids and Plasma Retinol-binding Protein", *Journ. of Biol. Chemistry*, 26(47):29613-29620 (1994).

International Search Report dated Dec. 15, 2005.

Database registry, "Methyl 2,4-butanedioate", Abstract, XP002341530, Database Accession No. RN1515-75-9, Chemical Abstracts Service, Columbus, OH, US (Nov. 16, 1984).

Database registry abstract, XP002341531, Database Accession No. RN 1515-76-0, Chemical Abstracts Service, Columbus, OH, US (Nov. 16, 1984).

Harmon et al., "*Trypanosoma brucei*: Effects of Methoprene and Other Isoprenoid Compounds on Procyclic and Bloodstream Forms in Vitro and in Mice," Experimental Parasitology, 87:229-236 (1997).

Kim et al., "Inhibition Effect of New Farnesol Derivatives on All-*Trans*- Retinoic Acid Metabolism," Metabolism, 50(11):1356-1360 (2001).

Kim et al., "Evaluation of Morphogenic Regulatory Activity of Farnesoic Acid and Its Derivatives Against *Candida albicans* Dimorphism," Bioorganic & Medicinal Chemistry Letters 12:895-898 (2002).

Fierz-David et al. XP009079288 "Tabelle I, Fettsaurechloride," Helvetica Chimica ACTA, 22:89 (1939).

Database Beilstein Registry No. 3255439 Abstract, "3-methyl-hexa-2,4-dienoic acid anilide," J. Chem Soc., 2030 (1929) XP-002420726.

Database Beilstein Registry No. 3197114 Abstract, "Hexa-2t,4t-dienanilide," J. Org. Chem., 23:1149-1151 (1958) XP-002420727.

Database Beilstein Registry No. 8331700 Abstract, "deca-2,4,6,8-tetraenoic acid (2,5-dimethoxy-phenyl)-amide," J. Chem. Soc., 9:1143-1146 (1999) XP-002420728.

Database Beilstein Registry No. 2777950 Abstract, "6-t-Butyl-3-methyl-4-N-stearoyl-aminophenol," ICI Ltd. (1967) XP-002420729.

Database Beilstein Registry No. 8155845 Abstract, "N-(3,5-dimethyl-4-hydroxyphenyl)-37,7-dimethyl-(2,E)-2,7-octadienoic amide," Inflammation Res., 45(4):192-197 (1996) XP-002420730.

Database Beilstein Registry No. 3321251 Abstract, "undec-10-enoic acid -(4-hydroxy-anilide)," Justus Liebigs Ann. Chem., 425: (1921) XP-002420731.

Database Beilstein Registry No. 3444613 Abstract, "docos-13-enoic acid-(4-hydroxy-anilide)," Gazzetta Chimica Italiana, 47(I): (1917) XP-002420732.

Database Beilstein Registry No. 3433858 Abstract, "13-cyclopent-2-enyl-tridecanoic acid-(4-hydroxy-anilide)," Chem. Zentralbl, 100(II):1284 (1929) XP-002420733.

Database Beilstein Registry No. 9822611 "{(2E,4E,6E,8E)-[3,7-dimethyl-9-(2,6,6-trimethyl-1-cyclohexenyl)nona-2,4,6,8-tetraenoylamino]}-(3-butyrylamino-4-hydroxy)phenylamide," Chem. Pharm. Bull., 52(5):501-506 (2004) XP-002420734.

European Search Report for Application No. EP 05 72 3179, mailed Sep. 10, 2007.

Corrections: *Biochemistry* 2007, 46(29), 8700.

Declaration from Robert Rando (4 pages).

Statement Concerning Inventorship Dispute 2009.

Declaration from Robert Rando (4 pages) Dec. 19, 2007.

\* cited by examiner

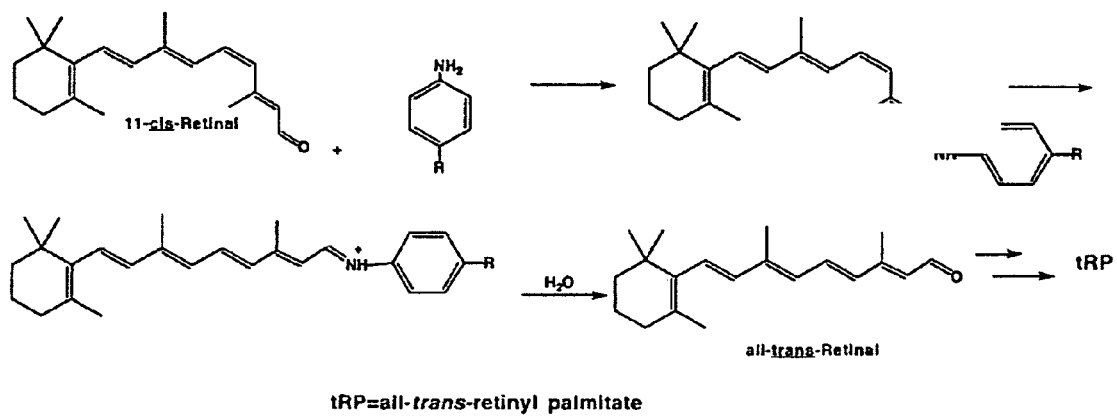
FIG. 3
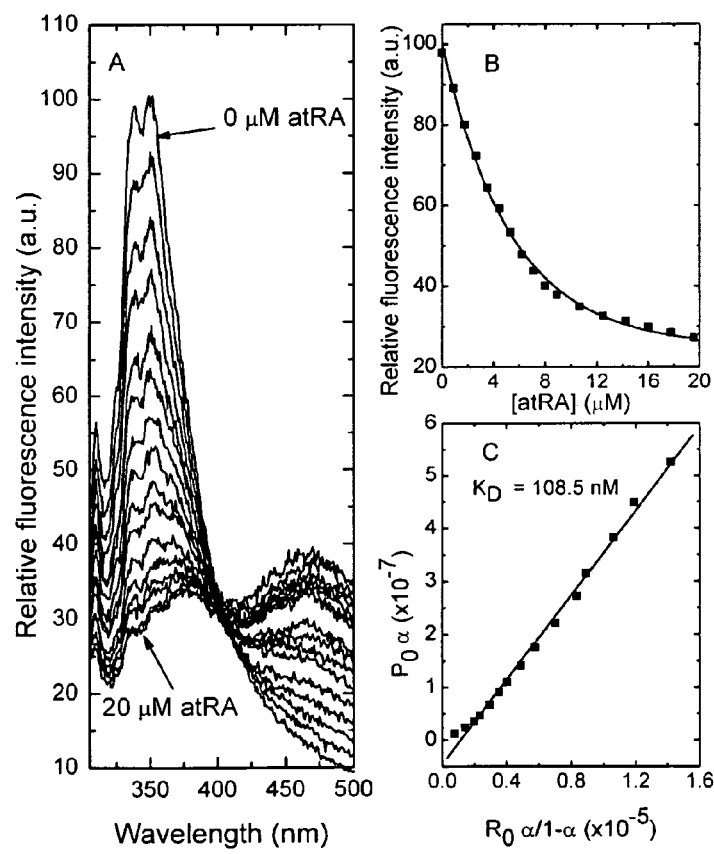
FIGS. 4 A, B, C

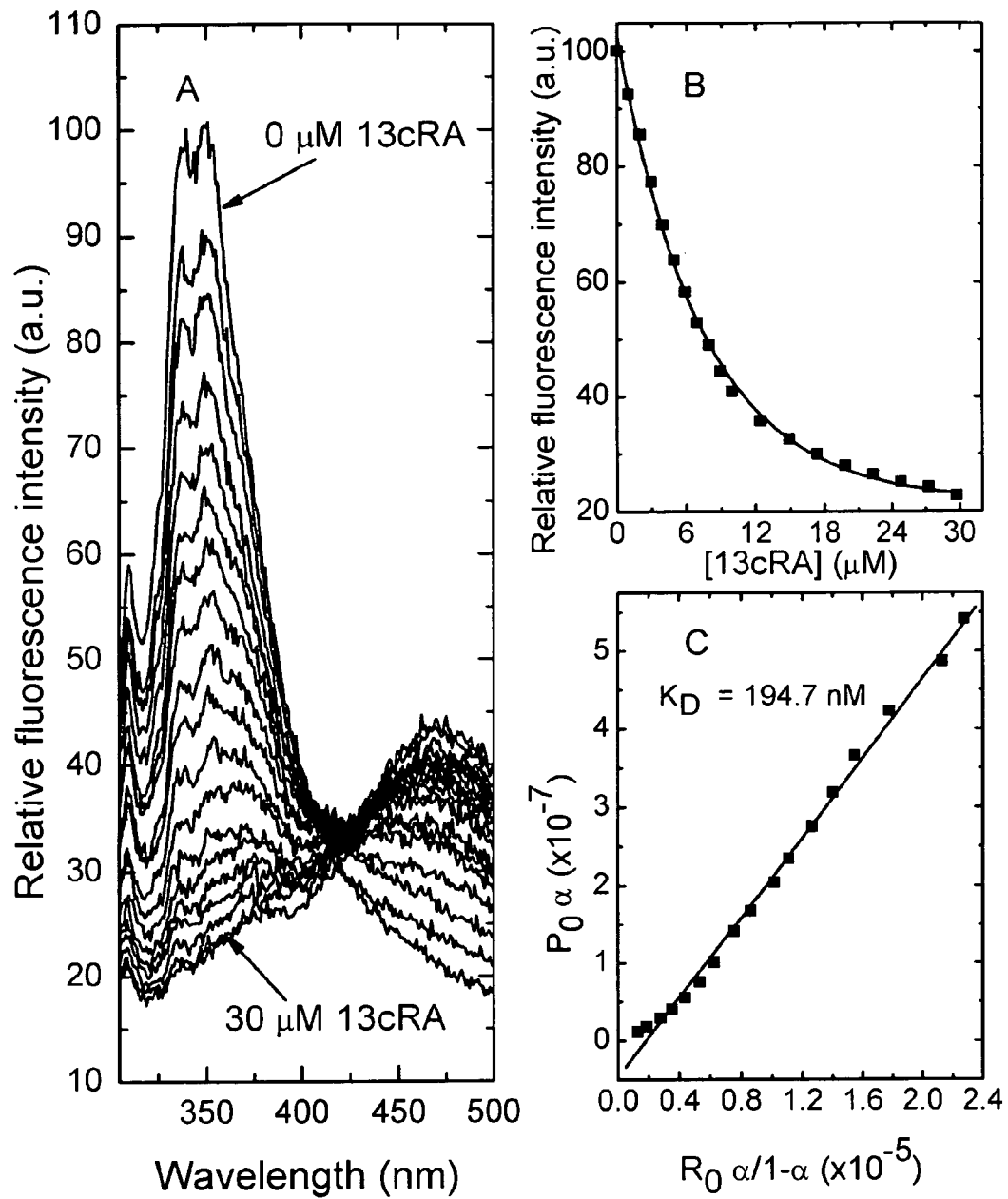
FIGS. 5 A, B, C

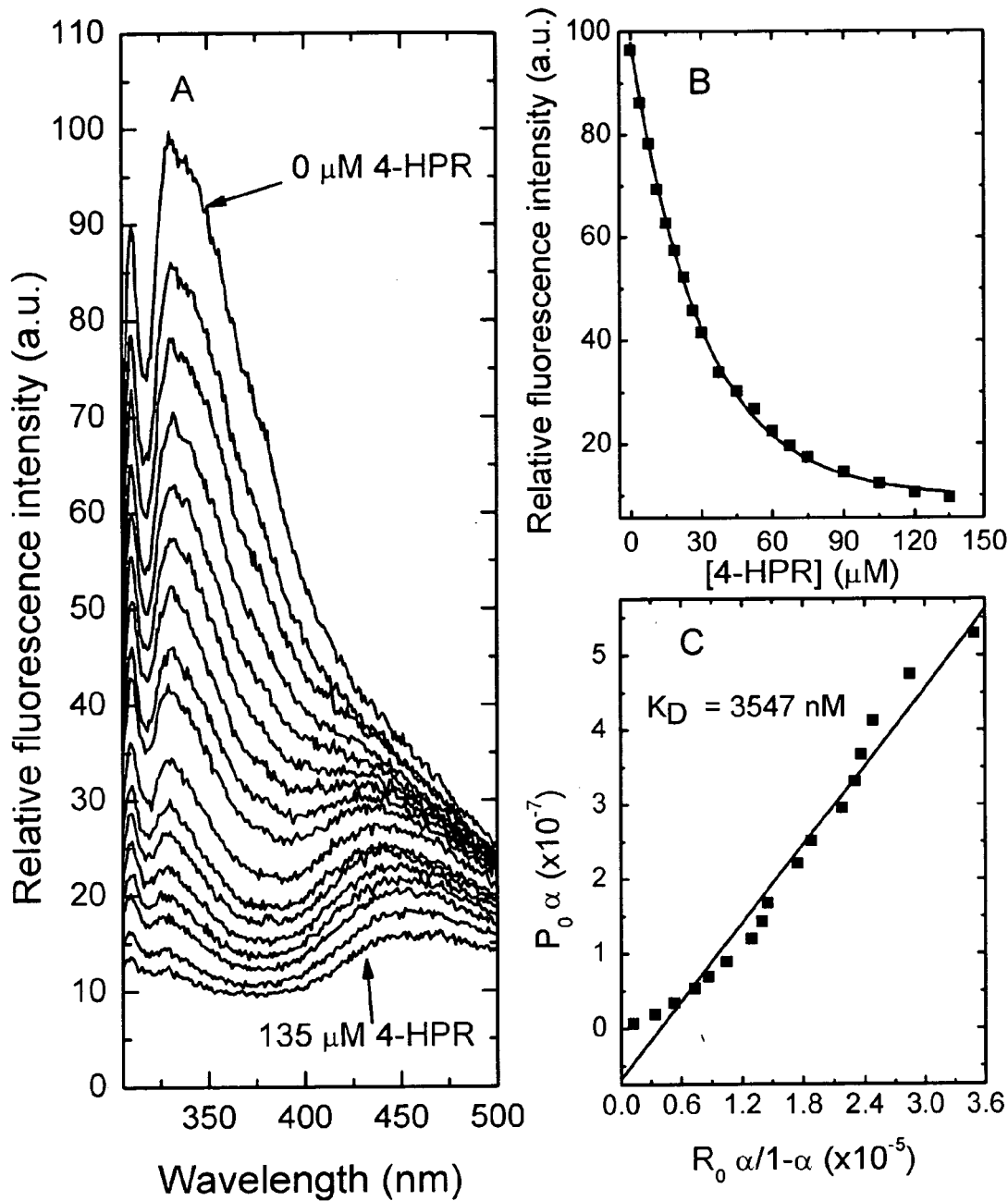
FIGS. 6 A, B, C

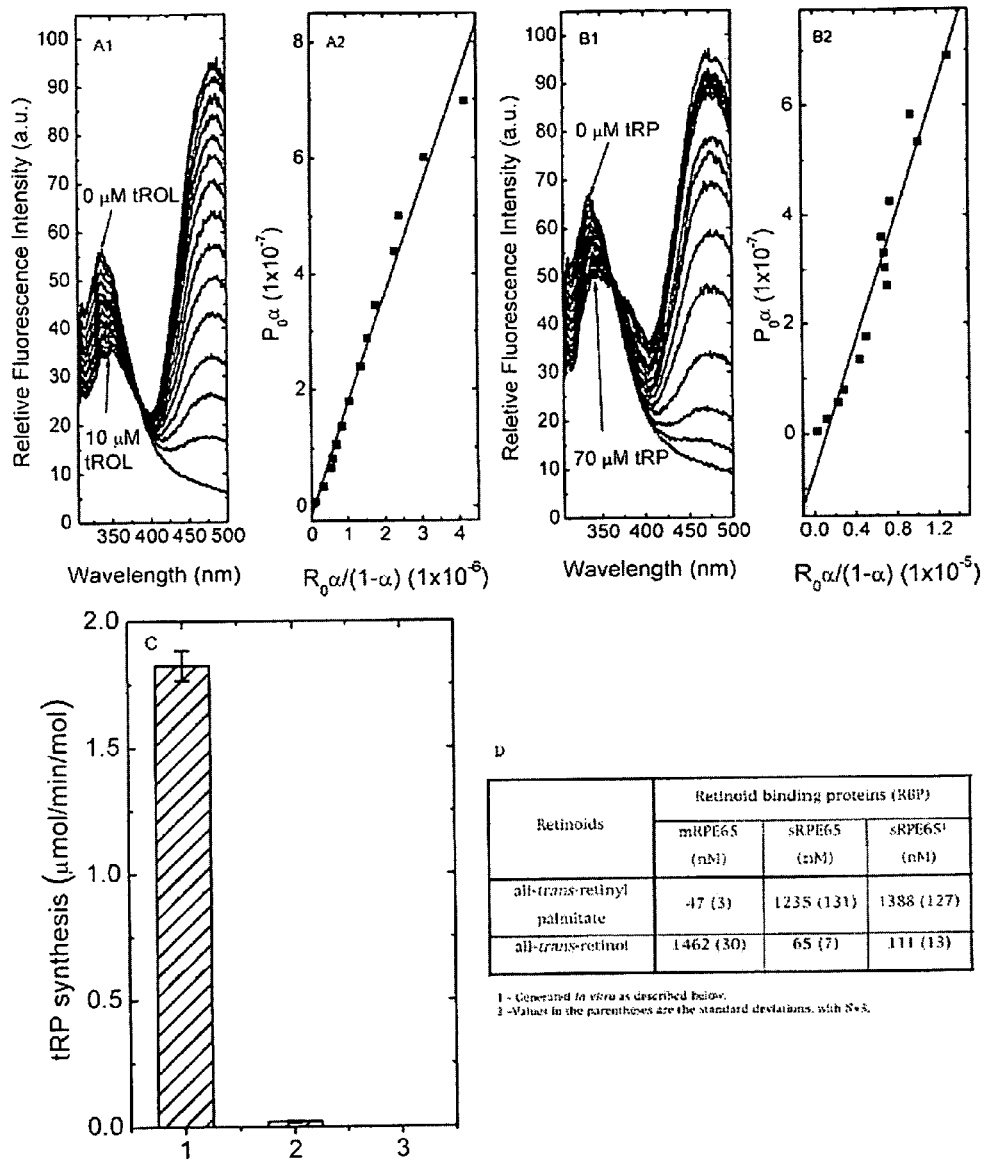
FIGS. 9 A1, A2, B1, B2, C, D

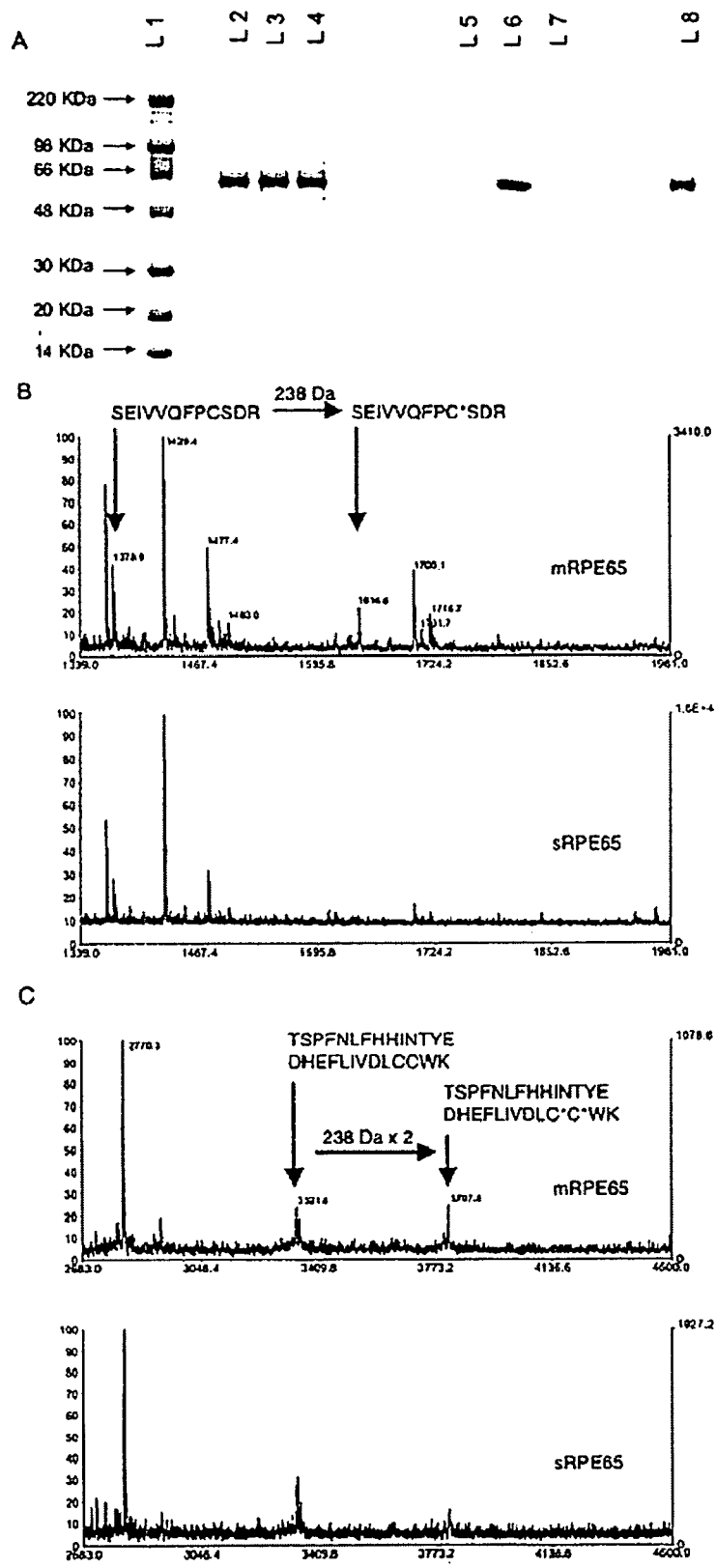
FIGS. 10 A, B, C

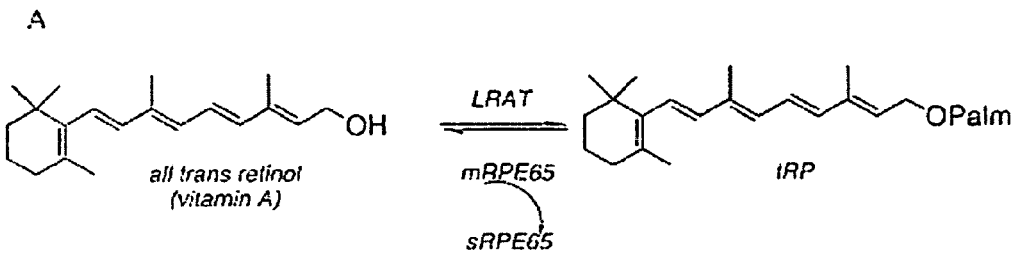
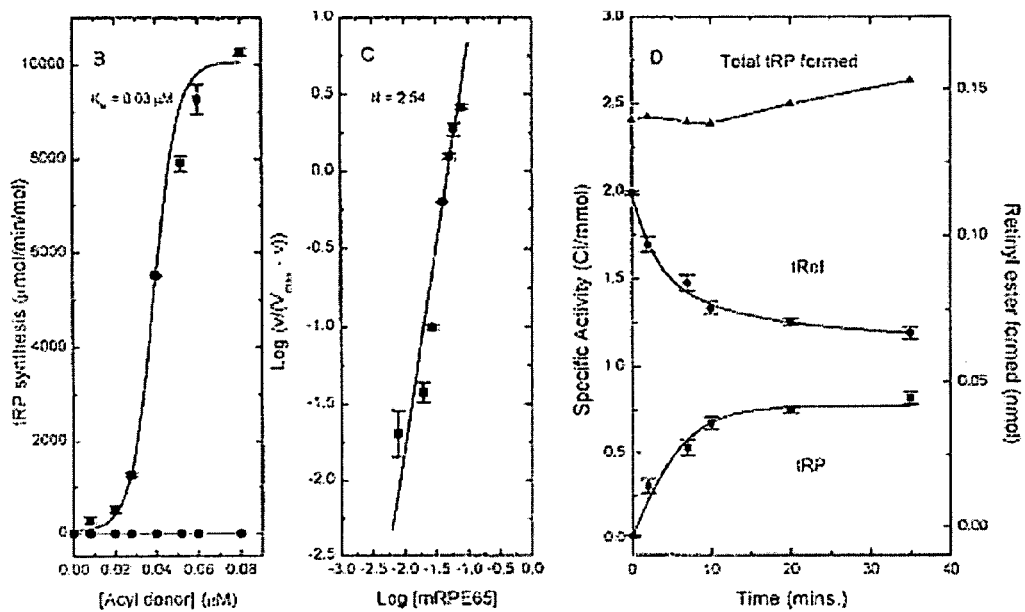
FIGS. 11 A, B, C, D

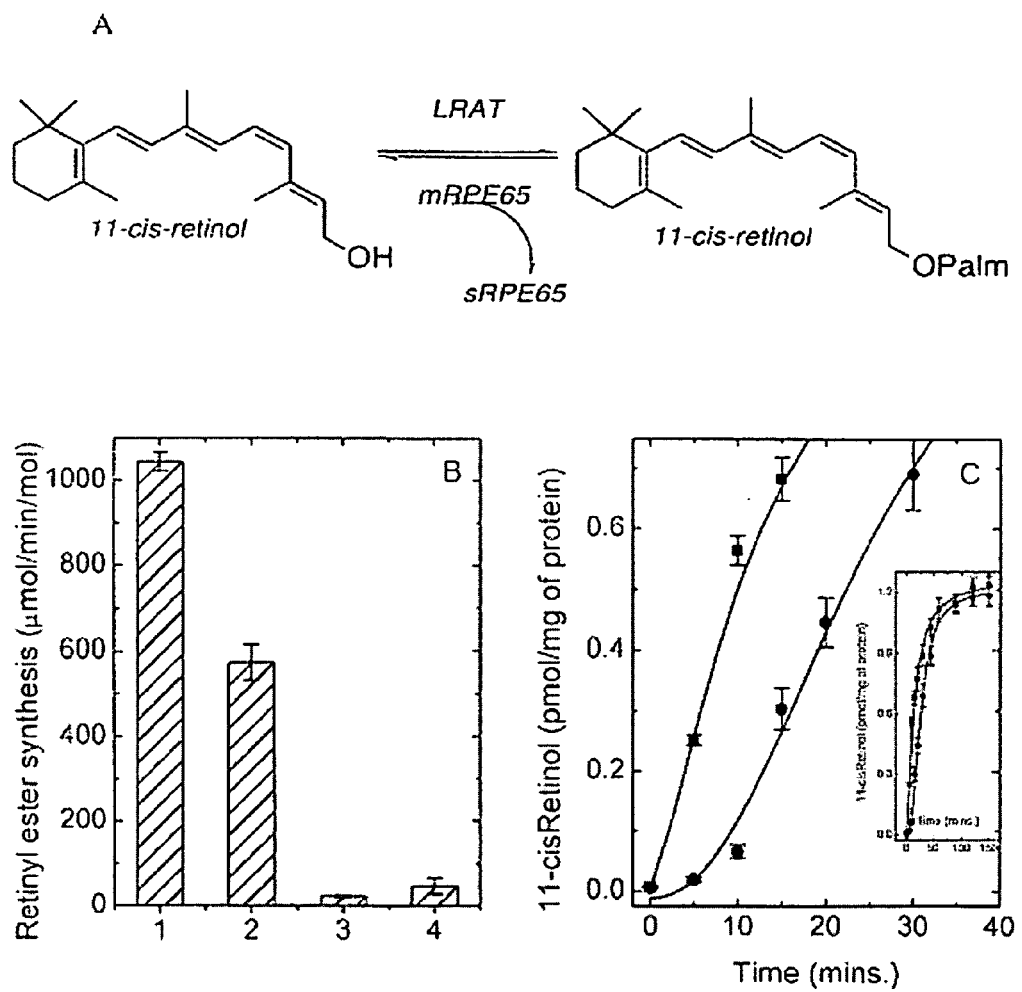
FIGS. 12 A, B, C

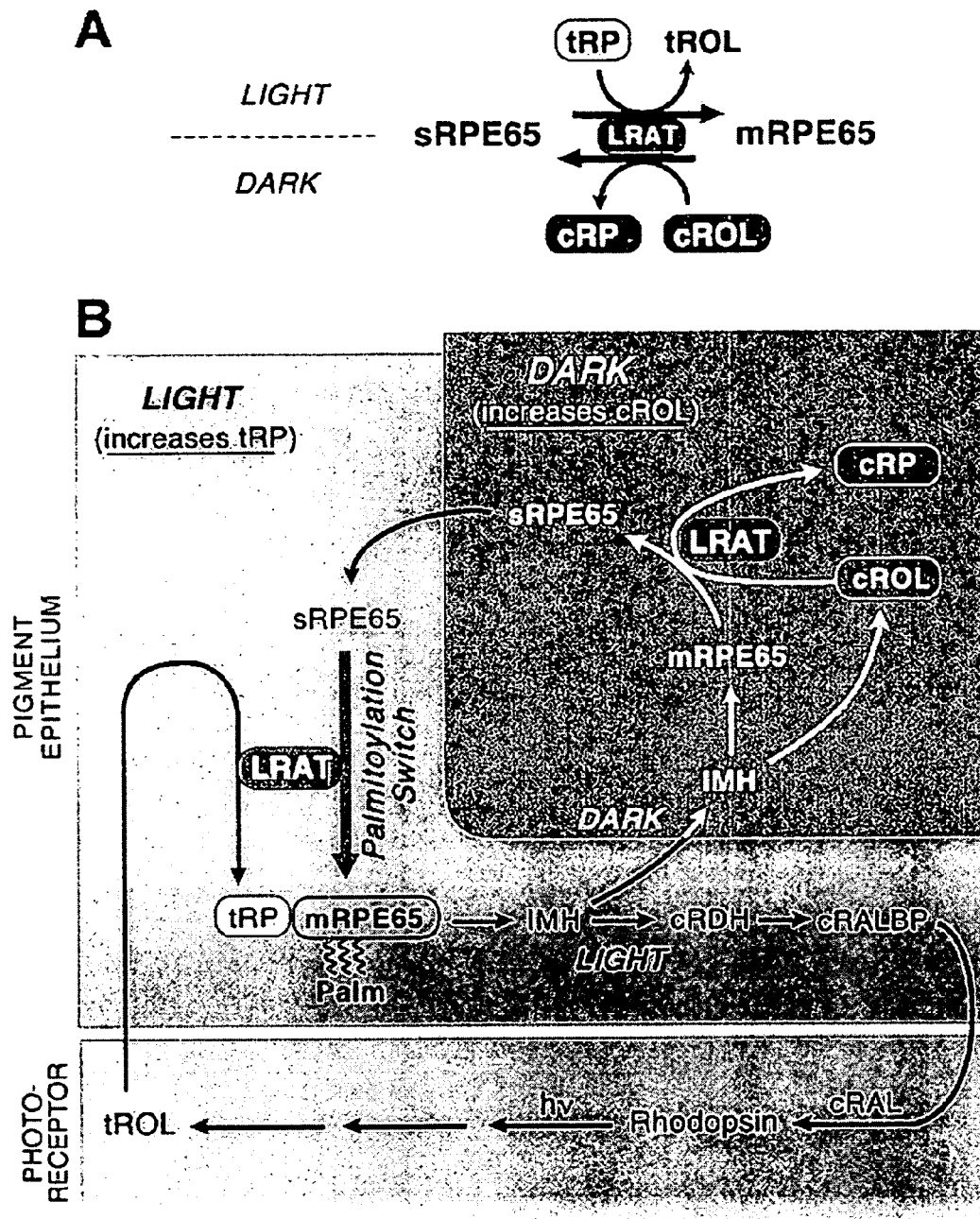
FIGS. 13 A, B

MANAGEMENT OF OPHTHALMOLOGIC DISORDERS, INCLUDING MACULAR DEGENERATION

CROSS-REFERENCE TO RELATED APPLICATION

This application is a continuation-in-part of International Application No. PCT/US2005/004990, filed Feb. 17, 2005, which claims the benefit of U.S. Provisional Patent Application Ser. No. 60/545,456, filed Feb. 17, 2004; U.S. Provisional Patent Application Ser. No. 60/567,604, filed May 3, 2004; and U.S. Provisional Patent Application Ser. No. 60/578,324, filed Jun. 9, 2004. All aforementioned applications are hereby incorporated herein by reference in their entirety.

STATEMENT REGARDING FEDERALLY SPONSORED RESEARCH OR DEVELOPMENT

Support for research leading to subject matter disclosed in this application was provided in part by the National Institutes of Health Grant Nos. R01-EY-04096 and/or R01-EY-015425. Accordingly, the United States Government has certain rights with respect to subject matter of this application.

INTRODUCTION

Age related diseases of vision are an ever-increasing health problem in industrial societies. Age related macular degeneration (AMD) affects millions of persons worldwide and is a leading cause of vision loss and blindness in ageing populations. In this disease, daytime vision (cone dominated vision) degrades with time because cone photoreceptors, which are concentrated in the foveal region of the retina, die. The incidence of this disease increases from less than 10% of the population 50 years of age to over 30% at 75 and continues upwards past this age. The onset of the disease has been correlated with the accumulation of complex and toxic biochemicals in and around the retinal pigment epithelium (RPE) and lipofuscin in the RPE. The accumulation of these retinotoxic mixtures is one of the most important known risk factors in the etiology of AMD.

The RPE forms part of the retinal-blood barrier and also supports the function of photoreceptor cells, including rods and cones. Among other activities, the RPE routinely phagocytoses spent outer segments of rod cells. In at least some forms of macular degeneration, accumulation of lipofuscin in the RPE is due in part to this phagocytosis. Retinotoxic compounds form in the discs of rod photoreceptor outer segments. Consequently, the retinotoxic compounds in the disc are brought into the RPE, where they impair further phagocytosis of outer segments and cause apoptosis of the RPE. Photoreceptors cells, including cone cells essential for daytime vision, then die, denuded of RPE support.

One of the retinotoxic compounds formed in the discs of rod outer segments is N-retinylidene-N-retinylethanolamine ($A_2E$), which is an important component of the retinotoxic lipofuscins. $A_2E$ is normally formed in the discs but in such small amounts that it does not impair RPE function upon phagocytosis. However, in certain pathological conditions, so much $A_2E$ can accumulate in the disc that the RPE is "poisoned" when the outer segment is phagocytosed.

$A_2E$ is produced from all-trans-retinal, one of the intermediates of the rod cell visual cycle. During the normal visual cycle (summarized in FIG. 1), all-trans-retinal is produced inside rod outer-segment discs. The all-trans-retinal can react with phosphatidylethanolamine (PE), a component of the disc membrane, to form N-retinylidene-PE. Rim protein (RmP), an ATP-binding cassette transporter located in the membranes of rod outer-segment discs, then transports all-trans-retinal and/or N-retinylidene-PE out of the disc and into rod outer-segment cytoplasm. The environment there favors hydrolysis of the N-retinylidene-PE. The all-trans-retinal is reduced to all-trans-retinol in the rod cytoplasm. The all-trans-retinol then crosses the rod outer-segment plasma membrane into the extracellular space and is taken up by cells of the retinal pigment epithelium (RPE). The all-trans-retinol is converted through a series of reactions to 11-cis-retinal, which returns to the photoreceptor and continues in the visual cycle.

However, defects in RmP can derange this process by impeding removal of all-trans-retinal from the disc. In a recessive form of macular degeneration called Stargardt's disease ($1/10,000$ incidence rate often affecting children; 25,00 affected individuals in the U.S.), the gene encoding RmP, abcr, is mutated, and the transporter is nonfunctional. As a result, all-trans-retinal and/or N-retinylidene-PE become trapped in the disc. The N-retinylidene-PE can then react with another molecule of all-trans-retinal to form N-retinylidene-N-retinylethanolamine ($A_2E$); this is summarized in FIG. 2. As noted above, some $A_2E$ is formed even under normal conditions; however, its production is greatly increased when its precursors accumulate inside the discs due to the defective transporter, and can thereby cause macular degeneration.

Other forms of macular degeneration may also result from pathologies that result in lipofuscin accumulation. A dominant form of Stargardt's disease, known as chromosome 6-linked autosomal dominant macular dystrophy (ADMD, OMIM #600110), is caused by a mutation in the gene encoding elongation of very long chain fatty acids-4, elovl4.

There are few, if any, preventative treatments for AMD, and therapeutic interventions are available for only certain, less common, forms of the disease.

SUMMARY

This disclosure relates to compositions, systems, and methods for managing macular degeneration, and, more specifically, for preventing the accumulation of retinotoxic compounds in and around the retinal pigment epithelium.

In one embodiment, the accumulation of $A_2E$ in rod outer-segment discs is prevented or reduced. It has been found that $A_2E$ production in discs can be reduced by administering a drug that limits the visual cycle. The limitation can be achieved in a number of ways. In one approach, a drug can effectively short-circuit the portion of the visual cycle that generates the $A_2E$ precursor, all-trans-retinal. In another approach, a drug can inhibit particular steps in the visual cycle necessary for synthesizing all-trans-retinal. In yet another approach, a drug can prevent binding of intermediate products (retinyl esters) to certain chaperone proteins in the retinal pigment epithelium.

In one embodiment, a method of treating or preventing macular degeneration in a subject may include administering to the subject a drug that short-circuits the visual cycle at a step of the visual cycle that occurs outside a disc of a rod photoreceptor cell. In another embodiment, a method of treating or preventing macular degeneration in a subject may include administering to the subject a drug that inhibits and/or interferes with at least one of lecithin retinol acyl transferase, RPE65, 11-cis-retinol dehydrogenase, and isomerohydrolase.

In yet another embodiment, a method of identifying a macular degeneration drug may include administering a candidate drug to a subject having, or at risk for developing, macular degeneration, and measuring accumulation of a retinotoxic compound in the retinal pigment epithelium of the subject.

A wide variety of drugs are contemplated for use. In some embodiments, inhibitors of the visual cycle include retinoic acid analogs. In other embodiments, drugs that short circuit the visual cycle include aromatic amines and hydrazines.

BRIEF DESCRIPTION OF THE FIGURES

FIG. 3 depicts an intervention for short-circuiting the visual cycle.
FIGS. 4A-C depicts data concerning the binding of all-trans-retinoic acid to RPE65.
FIGS. 5A-C depicts data concerning the binding of 13-cis-retinoic acid to RPE65.
FIGS. 6A-C depicts data concerning the binding of N-(4-hydroxyphenyl)retinamide (4-HPR) to RPE65.
FIGS. 9A1, A2, B1, and B2 depict data concerning the binding of all-trans-retinol and all-trans-retinyl palmitate to purified sRPE65.
FIG. 9C depicts data concerning binding of vitamin A to sRPE65.
FIG. 9D lists binding constants measured for various binding partners.
FIGS. 10A-C depict data concerning in vivo palmitoylation of mRPE65.
FIGS. 11A-D depict data concerning interconversion of mRPE65 and sRPE65.
FIGS. 12A-C depict data concerning palmitoylation of 11-cis-retinol.
FIGS. 13A and B depict how regulatory elements described might direct the flow of retinoids in vision.
FIG. 27A shows acute effects of drugs 1 h after 50 mg/kg (i.p).
FIG. 27B shows persistent effects of TDT and TDH 3 days after treatment.

DETAILED DESCRIPTION

Overview

Figure 1:
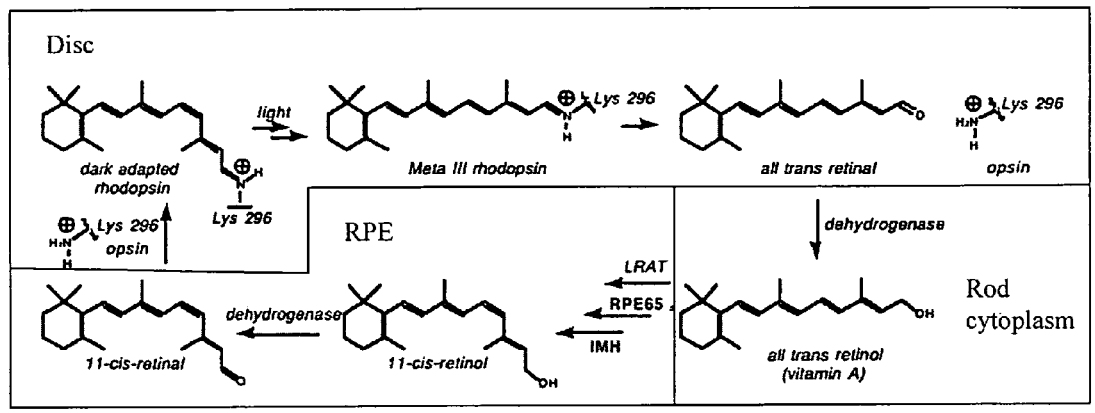
FIG. 1 depicts the visual cycle.

The present disclosure provides compositions and methods for managing macular degeneration by preventing or reducing the accumulation of $A_2E$ in rod outer-segment discs. $A_2E$ accumulation can be prevented or reduced by decreasing the amount of all-trans-retinal present in discs of rod outer segments. In one approach, a drug may be administered that inhibits one or more enzymatic steps in the visual cycle, so that production of all-trans-retinal is diminished. In another approach, a drug may be administered that drives the isomerization of 11-cis-retinal to all-trans-retinal in the RPE, thereby decreasing the amount 11-cis-retinal that returns to the outer segment discs to be reisomerized to all-trans-retinal.

Definitions

For convenience, before further description of exemplary embodiments, certain terms employed in the specification, examples, and appended claims are collected here. These definitions should be read in light of the remainder of the disclosure and as understood by a person of skill in the art.

The articles "a" and "an" are used herein to refer to one or to more than one (i.e., to at least one) of the grammatical object of the article. By way of example, "an element" means one element or more than one element.

The term "access device" is an art-recognized term and includes any medical device adapted for gaining or maintaining access to an anatomic area. Such devices are familiar to artisans in the medical and surgical fields. An access device may be a needle, a catheter, a cannula, a trocar, a tubing, a shunt, a drain, or an endoscope such as an otoscope, nasopharyngoscope, bronchoscope, or any other endoscope adapted for use in the joint area, or any other medical device suitable for entering or remaining positioned within the preselected anatomic area.

The terms "biocompatible compound" and "biocompatibility" when used in relation to compounds are art-recognized. For example, biocompatible compounds include compounds that are neither themselves toxic to the host (e.g., an animal or human), nor degrade (if the compound degrades) at a rate that produces monomeric or oligomeric subunits or other byproducts at toxic concentrations in the host. In certain embodiments, biodegradation generally involves degradation of the compound in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the compound. Consequently, in certain embodiments, toxicology of a biodegradable compound intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise compounds comprising 99%, 98%, 97%, 96%, 95%, 90%, 85%, 80%, 75% or even less of biocompatible compounds, e.g., including compounds and other materials and excipients described herein, and still be biocompatible.

To determine whether a compound or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 µL of various concentrations of the degraded sample products are placed in 96-well tissue culture plates and seeded with human gastric carcinoma cells (GT3TKB) at $10^4$/well density. The degraded sample products are incubated with the GT3TKB cells for 48 hours. The results of the assay may be plotted as % relative growth vs. concentration of degraded sample in the tissue-culture well. In addition, compounds and formulations may also be evaluated by well-known in vivo tests, such as subcutaneous implantations in rats to confirm that they do not cause significant levels of irritation or inflammation at the subcutaneous implantation sites.

The term "biodegradable" is art-recognized, and includes compounds, compositions and formulations, such as those described herein, that are intended to degrade during use. Biodegradable compounds typically differ from non-biodegradable compounds in that the former may be degraded during use. In certain embodiments, such use involves in vivo use, such as in vivo therapy, and in other certain embodiments, such use involves in vitro use. In general, degradation attributable to biodegradability involves the degradation of a biodegradable compound into its component subunits, or digestion, e.g., by a biochemical process, of the compound into smaller subunits. In certain embodiments, two different types of biodegradation may generally be identified. For example, one type of biodegradation may involve cleavage of bonds (whether covalent or otherwise) in the compound. In such biodegradation, monomers and oligomers typically result, and even more typically, such biodegradation occurs by cleavage of a bond connecting one or more of substituents of a compound. In contrast, another type of biodegradation may involve cleavage of a bond (whether covalent or otherwise) internal to side chain or that connects a side chain to the compound. For example, a therapeutic agent or other chemical moiety attached as a side chain to the compound may be released by biodegradation. In certain embodiments, one or the other or both generally types of biodegradation may occur during use of a compound. As used herein, the term "biodegradation" encompasses both general types of biodegradation.

The degradation rate of a biodegradable compound often depends in part on a variety of factors, including the chemical identity of the linkage responsible for any degradation, the molecular weight, crystallinity, biostability, and degree of cross-linking of such compound, the physical characteristics of the implant, shape and size, and the mode and location of administration. For example, the greater the molecular weight, the higher the degree of crystallinity, and/or the greater the biostability, the biodegradation of any biodegradable compound is usually slower. The term "biodegradable" is intended to cover materials and processes also termed "bioerodible".

In certain embodiments, if the biodegradable compound also has a therapeutic agent or other material associated with it, the biodegradation rate of such compound may be characterized by a release rate of such materials. In such circumstances, the biodegradation rate may depend on not only the chemical identity and physical characteristics of the compound, but also on the identity of any such material incorporated therein.

In certain embodiments, compound formulations biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the compound degrades in a period of between about one hour and several weeks, depending on the desired application.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "drug delivery device" is an art-recognized term and refers to any medical device suitable for the application of a drug to a targeted organ or anatomic region. The term includes those devices that transport or accomplish the instillation of the compositions towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has the composition included in its substance or coated on its surface is understood to be a drug delivery device.

When used with respect to a therapeutic agent or other material, the term "sustained release" is art-recognized. For example, a subject composition that releases a substance over time may exhibit sustained release characteristics, in contrast to a bolus type administration in which the entire amount of the substance is made biologically available at one time. For example, in particular embodiments, upon contact with body fluids including blood, tissue fluid, lymph or the like, the compound matrices (formulated as provided herein and otherwise as known to one of skill in the art) may undergo gradual degradation (e.g., through hydrolysis) with concomitant release of any material incorporated therein, for a sustained or extended period (as compared to the release from a bolus). This release may result in prolonged delivery of therapeutically effective amounts of any incorporated a therapeutic agent. Sustained release will vary in certain embodiments as described in greater detail below.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "or" as used herein should be understood to mean "and/or", unless the context clearly indicates otherwise.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject having been diagnosed with the disease, disorder, or condition, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject which may be predisposed to the disease, disorder and/or condition but has not yet been diagnosed as having it. Preventing a condition related to a disease includes stopping the condition from occurring after the disease has been diagnosed but before the condition has been diagnosed.

The term "fluid" is art-recognized to refer to a non-solid state of matter in which the atoms or molecules are free to move in relation to each other, as in a gas or liquid. If unconstrained upon application, a fluid material may flow to assume the shape of the space available to it, covering for example, the surfaces of an excisional site or the dead space left under a flap. A fluid material may be inserted or injected into a limited portion of a space and then may flow to enter a larger portion of the space or its entirety. Such a material may be termed "flowable." This term is art-recognized and includes, for example, liquid compositions that are capable of being sprayed into a site; injected with a manually operated syringe fitted with, for example, a 23-gauge needle; or delivered through a catheter. Also included in the term "flowable" are those highly viscous, "gel-like" materials at room temperature that may be delivered to the desired site by pouring, squeezing from a tube, or being injected with any one of the commercially available injection devices that provide injection pressures sufficient to propel highly viscous materials through a delivery system such as a needle or a catheter. When the compound used is itself flowable, a composition comprising it need not include a biocompatible solvent to allow its dispersion within a body cavity. Rather, the flowable compound may be delivered into the body cavity using a delivery system that relies upon the native flowability of the material for its application to the desired tissue surfaces. For example, if flowable, a composition comprising compounds can be injected to form, after injection, a temporary biomechanical barrier to coat or encapsulate internal organs or tissues, or it can be used to produce coatings for solid implantable devices. In certain instances, flowable subject compositions have the ability to assume, over time, the shape of the space containing it at body temperature.

Viscosity is understood herein as it is recognized in the art to be the internal friction of a fluid or the resistance to flow exhibited by a fluid material when subjected to deformation. The degree of viscosity of the compound may be adjusted by the molecular weight of the compound and other methods for altering the physical characteristics of a specific compound will be evident to practitioners of ordinary skill with no more than routine experimentation. The molecular weight of the compound used may vary widely, depending on whether a rigid solid state (higher molecular weights) desirable, or whether a fluid state (lower molecular weights) is desired.

The phrase "pharmaceutically acceptable" is art-recognized. In certain embodiments, the term includes compositions, compounds and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition, such as macular degeneration. The terms include without limitation pharmaceutically acceptable salts thereof and pro-drugs. Such agents may be acidic, basic, or salts; they may be neutral molecules, polar molecules, or molecular complexes capable of hydrogen bonding; they may be pro-drugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a compound, produces some desired effect at a reasonable benefit/risk ratio applicable to any medical treatment. In certain embodiments, the term refers to that amount necessary or sufficient to eliminate, reduce or maintain (e.g., prevent the spread of) a tumor or other target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a compound matrix, which will depend in part on the chemical and physical characteristics of the compound; the identity of the agent; the mode and method of administration; and any other materials incorporated in the compound matrix in addition to the agent.

"Radiosensitizer" is defined as a therapeutic agent that, upon administration in a therapeutically effective amount, promotes the treatment of one or more diseases or conditions that are treatable with electromagnetic radiation. In general, radiosensitizers are intended to be used in conjunction with electromagnetic radiation as part of a prophylactic or therapeutic treatment. Appropriate radiosensitizers to use in conjunction with treatment with the subject compositions will be known to those of skill in the art.

"Electromagnetic radiation" as used in this specification includes, but is not limited to, radiation having the wavelength of $10^{-20}$ to 10 meters. Particular embodiments of electromagnetic radiation employ the electromagnetic radiation of: gamma-radiation ($10^{-20}$ to $10^{-13}$ m), x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

"Retinol binding protein" (RBP) is the principal carrier of all-trans-retinol, which comprises over 90% of serum vitamin A. RBP is found in serum in association with a cotransport protein called transthyretin or prealbumin. Within cells, retinol and its metabolites are bound to retinol-binding proteins in the cytosol and nucleus (Folli et al. J. Biol. Chem., Vol. 277:41970; Ong, et al. (1994) in *The Retinoids: Biology, Chemistry and Medicine* (Sporn, M. B., Roberts, A. B., and Goodman, D. S., eds), pp. 283-318, Raven Press Ltd., New York; and Li et al. (1996) *Annu. Rev. Nutr.* 16, 205). The eye shows a very marked preference for acquiring retinol from the retinol-RBP complex (Vogel et al. (2002) Biochemistry. 41(51):15360). The RBP family contains 7 members: RBP1-7. RBP1 is also referred to as cellular RBP1, HGNC:9919, CRABP-I, CRBP, CRBP1, and RBPC, and its nucleotide and amino acid sequences are set forth in GenBank Accession Nos. NM_002899 and NP_002890. RBP2 is also referred to as cellular RBP2, HGNC:9920, CRABP-II, CRBP2, CRB-PII, and RBPC2, and its nucleotide and amino acid sequences are set forth in GenBank Accession Nos. NM_004164 and NP_004155. RBP3 is also referred to as insterstitial RBP3, IRBP; RBPI; D10S64; D10S65; and D10S66, and its nucleotide and amino acid sequences are set forth in GenBank Accession Nos. NM_002900 and NP_002891. RBP4 is also referred to as plasma RBP4, and its nucleotide and amino acid sequences are set forth in GenBank Accession Nos. NM_006744 and NP_006735. RBP5 is also referred to as cellular RBP5, CRBP3; CRBPIII; and CRBP-III, and its nucleotide and amino acid sequences are set forth in GenBank Accession Nos. NM_031491 and NP_113679. RBP6 is also referred to as cellular retinoic acid-binding protein 2, cellular retinoic acid binding protein 2, CRABP2, HGNC: 2339, CRABP-II, and its nucleotide and amino acid sequences are set forth in GenBank Accession Nos. NM_001878 and NP_001869. RBP7 is also referred to as cellular RBP7, HGNC:30316, CRBP4, CRBPIV, and MGC70641, and its nucleotide and amino acid sequences are set forth in GenBank Accession Nos: NM_052960 and NP_443192. The RBP that is believed to import Vitamin A into the eye are the CRBPs. Inhibition of other RBPs may also be used for treating and/or preventing diseases of the eye.

The phrases "systemic administration," "administered systemically," "peripheral administration" and "administered peripherally" are art-recognized, and include the administration of a subject composition or other material at a site remote from the site affected by the disease being treated. Administration of an agent directly into, onto or in the vicinity of a lesion of the disease being treated, even if the agent is subsequently distributed systemically, may be termed "local" or "topical" or "regional" administration.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The terms "incorporated" and "encapsulated" are art-recognized when used in reference to a therapeutic agent and a compound, such as a composition disclosed herein. In certain embodiments, these terms include incorporating, formulating or otherwise including such agent into a composition which allows for sustained release of such agent in the desired application. The terms may contemplate any manner by which a therapeutic agent or other material is incorporated into a compound matrix, including for example: the compound is a polymer, and the agent is attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other a therapeutic agent or other material in a subject composition.

More specifically, the physical form in which a therapeutic agent or other material is encapsulated in compounds may vary with the particular embodiment. For example, a therapeutic agent or other material may be first encapsulated in a microsphere and then combined with the compound in such a way that at least a portion of the microsphere structure is maintained. Alternatively, a therapeutic agent or other material may be sufficiently immiscible in a controlled-release compound that it is dispersed as small droplets, rather than being dissolved, in the compound. Any form of encapsulation or incorporation is contemplated by the present disclosure, in so much as the sustained release of any encapsulated therapeutic agent or other material determines whether the form of encapsulation is sufficiently acceptable for any particular use.

The term "biocompatible plasticizer" is art-recognized, and includes materials which are soluble or dispersible in the controlled-release compositions described herein, which increase the flexibility of the compound matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (about 20 weight percent or less), acetyl trihexyl citrate (about 20 weight percent or less), butyl benzyl phthalate, dibutyl phthalate, dioctylphthalate, n-butyryl tri-n-hexyl citrate, diethylene glycol dibenzoate (c. 20 weight percent or less) and the like.

"Small molecule" is an art-recognized term. In certain embodiments, this term refers to a molecule which has a molecular weight of less than about 2000 amu, or less than about 1000 amu, and even less than about 500 amu.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., C1-C30 for straight chain, C3-C30 for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to SH; the term "hydroxyl" means —OH; and the term "sulfonyl" is art-recognized and refers to SO$_2^-$. "Halide" designates the corresponding anion of the halogens, and "pseudohalide" has the definition set forth on page 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

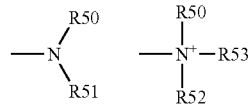

wherein R50, R51 and R52 each independently represent a hydrogen, an alkyl, an alkenyl, (CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group. The term "acylamino" is art-recognized and refers to a moiety that may be represented by the general formula:

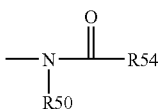

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

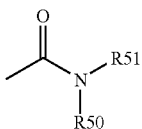

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of S alkyl, —S-alkenyl, —S-alkynyl, and —S—(CH$_2$)$_m$—R61, wherein m and R61 are defined above. Representative alkylthio groups include methylthio, ethyl thio, and the like. The term "carboxyl" is art recognized and includes such moieties as may be represented by the general formulas:

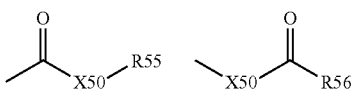

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

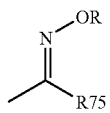

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, O-alkynyl, —O—(CH$_2$)$_m$—R61, where m and R61 are described above.

The term "sulfonate" is art recognized and refers to a moiety that may be represented by the general formula:

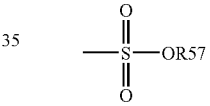

in which R57 is an electron pair, hydrogen, alkyl, cycloalkyl, or aryl.

The term "sulfate" is art recognized and includes a moiety that may be represented by the general formula:

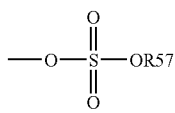

in which R57 is as defined above.

The term "sulfonamido" is art recognized and includes a moiety that may be represented by the general formula:

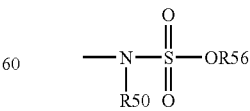

in which R50 and R56 are as defined above.

The term "sulfamoyl" is art-recognized and refers to a moiety that may be represented by the general formula:

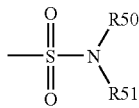

in which R50 and R51 are as defined above.

The term "sulfonyl" is art-recognized and refers to a moiety that may be represented by the general formula:

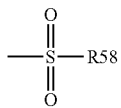

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

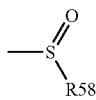

in which R58 is defined above.

The term "phosphoryl" is art-recognized and may in general be represented by the formula:

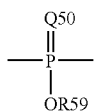

wherein Q50 represents S or O, and R59 represents hydrogen, a lower alkyl or an aryl. When used to substitute, e.g., an alkyl, the phosphoryl group of the phosphorylalkyl may be represented by the general formulas:

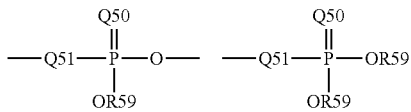

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

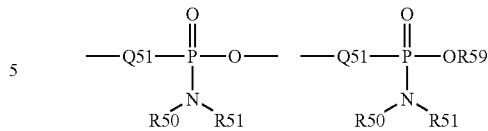

wherein Q51, R50, R51 and R59 are as defined above.

The term "phosphonamidite" is art-recognized and may be represented in the general formulas:

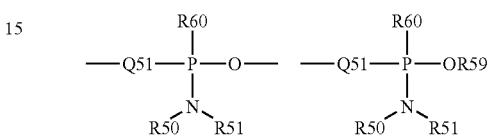

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls. The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

3. Compositions

As described above, macular degeneration may be treated or prevented by interfering with the visual cycle in such a way that diminishes the amount of all-trans-retinal present in the discs of the rod photoreceptor outer segments. Production of retinotoxic compounds by cone cells is negligible and may be ignored, because rods represent 95% of all photoreceptors.

FIG. 1 depicts the mammalian visual cycle. In the course of the visual cycle, a complex of 11-cis-retinal and opsin, known as rhodopsin, passes through a series of biochemical steps initiated by the absorption of light. Various steps of this cycle in distinct places. As FIG. 1 illustrates, the initial steps of light absorption to the dissociation of opsin and the formation of all-trans-retinal occur in the discs of the rod photoreceptor cell outer segment. The reduction of all-trans-retinal to all-trans-retinol takes place in the cytoplasm of the rod cell, and the remaining steps to regenerate 11-cis-retinal occur in the retinal pigment epithelium (RPE).

At least two broad approaches are contemplated for preventing the accumulation of all-trans-retinal in the disc. In one approach, one or more enzymatic steps or chaperone binding steps in the visual cycle may be inhibited so that the synthetic pathway to all-trans-retinal is blocked. In another approach, a portion of the visual cycle is "short-circuited," i.e., an early intermediate in the cycle is shunted to an intermediate that is two or more steps later in the visual cycle, so that these steps of the cycle are bypassed while the all-trans-retinal precursors are not in the disc.

A. Enzyme Inhibitors

Limiting the flux of retinoids through the visual cycle can be achieved by inhibiting any of the key biochemical reactions of the visual cycle. Each step of the cycle is potentially addressable in this fashion. Inhibiting an enzymatic step could thus be used to "stall" the visual cycle in the RPE, thereby keeping all-trans-retinal out of the discs.

Other steps in the visual cycle are also prone to inhibition. For example, as shown in FIG. 1, several enzymes act upon all-trans-retinol and its derivatives upon its return to the RPE, including LRAT (lecithin retinol acyl transferase), 11-cis-retinol dehydrogenase and IMH (isomerohydrolase). In addition, the chaperone RPE65 binds retinyl esters to make those typically hydrophobic compounds available to IMH for processing to 11-cis-retinol. These enzymes and chaperone may be targeted for inhibition and/or interference.

In certain embodiments, an inhibitor of isomerohydrolase (IMH), an inhibitor 11-cis-retinol dehydrogenase, an inhibitor of lecithin retinol acyl transferase (LRAT), or an antagonist of chaperone retinal pigment epithelium (RPE65) has a structure represented by formula I:

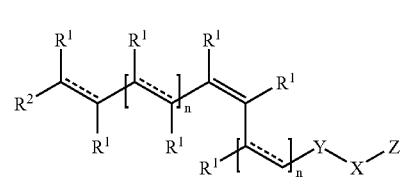

I wherein, independently for each occurrence, n is 0 to 10 inclusive;

$R^1$ is hydrogen or alkyl;

$R^2$ is hydrogen, alkyl, cycloalkyl, alkenyl, cycloalkenyl, alkynyl, aryl, or aralkyl;

Y is —C($R_b$)$_p$—, —C(=O)— or —C($R_b$)$_p$C(=O)—;

X is —O—, —N($R_a$)—, —C($R_b$)$_p$— or —S—;

Z is alkyl, haloalkyl, —(CH$_2$CH$_2$O)$_p$$R_b$ or —C(=O)$R_b$;

p is 0 to 20 inclusive;

$R_a$ is hydrogen, alkyl, aryl or aralkyl;

$R_b$ is hydrogen, alkyl or haloalkyl; and

----- denotes a single bond, a cis double bond, or a trans double bond.

In certain embodiments, an inhibitor of isomerohydrolase (IMH), an inhibitor 11-cis-retinol dehydrogenase, an inhibitor of lecithin retinol acyl transferase (LRAT), or an antagonist of chaperone retinal pigment epithelium (RPE65) has a structure represented by formula II:

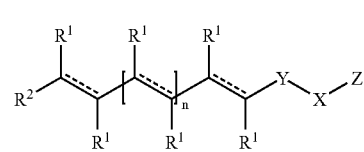

II wherein, independently for each occurrence, n is 0 to 10 inclusive;

$R^1$ is hydrogen or alkyl;

$R^2$ is hydrogen, alkyl, cycloalkyl, alkenyl, cycloalkenyl, alkynyl, aryl, or aralkyl;

Y is —C($R_b$)$_p$—, —C(=O)— or —C($R_b$)$_p$C(=O)—;

X is hydrogen, —O—, —S—, —N($R_a$)—, —N($R_a$)—N($R_a$)—, —C(=O)—, —C(=N$R_a$)—, —C(=NOH)—, —C(=S)— or —C($R_b$)$_p$—;

Z is absent, hydrogen, alkyl, haloalkyl, aryl, aralkyl, —CN, —O$R_b$, —(CH$_2$CH$_2$O)$_p$$R_b$, —C(=O)$R_b$, —C(=O)CH$_2$F, —C(=O)CHF$_2$, —C(=O)CF$_3$, —C(=O)CHN$_2$, —C(=O)O$R_b$, —C(=O)CH$_2$OC(=O)$R_b$, —C(=O)C(=C($R_b$)$_2$)$R_b$,

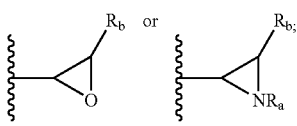

p is 0 to 20 inclusive;
$R_a$ is hydrogen, alkyl, aryl or aralkyl;
$R_b$ is hydrogen, alkyl, haloalkyl, aryl or aralkyl; and
----denotes a single bond, a cis double bond or a trans double bond.

In certain embodiments, an inhibitor of isomerohydrolase (IMH), an inhibitor 11-cis-retinol dehydrogenase, an inhibitor of lecithin retinol acyl transferase (LRAT), or an antagonist of chaperone retinal pigment epithelium (RPE65) has a structure represented by formula III:

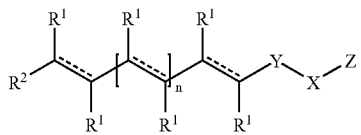

III wherein, independently for each occurrence,
n is 0 to 10 inclusive;
$R^1$ is hydrogen or alkyl;
$R^2$ is hydrogen, alkyl, cycloalkyl, alkenyl, cycloalkenyl, alkynyl, aryl, or aralkyl;
Y is —$CR_b(OR_b)$—, —$CR_b(N(R_a)_2)$—, —$C(R_b)_p$—, —C(=O)— or —$C(R_b)_pC(=O)$—;
X is —O—, —S—, —$N(R_a)$—, —C(=O)—, or —$C(R_b)_p$—;
Z is hydrogen, alkyl, haloalkyl, aryl, aralkyl, —$OR_b$, —$N(R_b)_2$, —$(CH_2CH_2O)_pR_b$, —$C(=O)R_b$, —$C(=NR_a)R_b$, —$C(=NOR_b)R_b$, —$C(OR_b)(R_b)_2$, —$C(N(R_a)_2)(R_b)_2$ or —$(CH_2CH_2O)_pR_b$;
p is 0 to 20 inclusive;
$R_a$ is hydrogen, alkyl, aryl or aralkyl;
$R_b$ is hydrogen, alkyl, haloalkyl, aryl or aralkyl; and
----denotes a single bond or a trans double bond.

In certain embodiments, an inhibitor of isomerohydrolase (IMH), an inhibitor 11-cis-retinol dehydrogenase, an inhibitor of lecithin retinol acyl transferase (LRAT), or an antagonist of chaperone retinal pigment epithelium (RPE65) has a structure represented by formula VI:

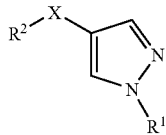

VI wherein, independently for each occurrence,
$R^1$ is hydrogen, alkyl, aryl or aralkyl;
X is alkyl, alkenyl, —$C(R_b)_2$—, —C(=O)—, —$C(=NR_a)$—, —$C(OH)R_b$ or —$C(N(R_a)_2)R_b$—;
$R^2$ is hydrogen, alkyl, cycloalkyl, alkenyl, cycloalkenyl, alkynyl, aryl, or aralkyl;
$R_a$ is hydrogen, alkyl, aryl or aralkyl; and
$R_b$ is hydrogen or alkyl.

In certain embodiments, an inhibitor of isomerohydrolase (IMH), an inhibitor 11-cis-retinol dehydrogenase, an inhibitor of lecithin retinol acyl transferase (LRAT), or an antagonist of chaperone retinal pigment epithelium (RPE65) has a structure represented by formula I:

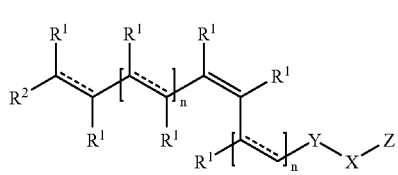

I wherein, independently for each occurrence,
n is 0 to 10 inclusive;
$R^1$ is hydrogen or alkyl;
$R^2$ is hydrogen, alkyl, cycloalkyl, alkenyl, cycloalkenyl, alkynyl, aryl, or aralkyl;
Y is —$C(R_b)_p$—, —C(=O)— or —$C(R_b)_pC(=O)$—;
X is —O—, —$N(R_a)$—, —$C(R_b)_p$— or —S—;
Z is alkyl, haloalkyl, —$(CH_2CH_2O)_pR_b$ or —$C(=O)R_b$;
p is 0 to 20 inclusive;
$R_a$ is hydrogen, alkyl, aryl or aralkyl;
$R_b$ is hydrogen, alkyl or haloalkyl; and
----denotes a single bond, a cis double bond, or a trans double bond.

In certain embodiments, an inhibitor of isomerohydrolase (IMH) has a structure represented by formula Ia, Ib, Ic, or Id:

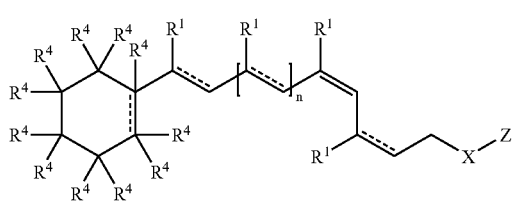

Ia

Ib

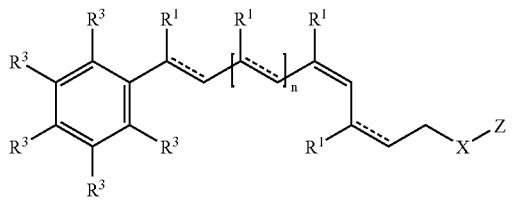

Ic

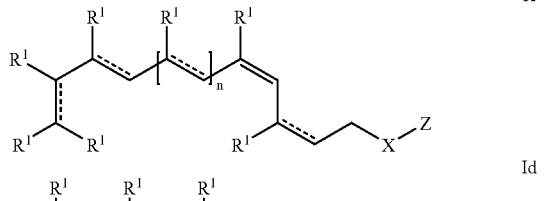

Id wherein, independently for each occurrence,
n is 0 to 4 inclusive;
$R^1$ is hydrogen or alkyl;

R³ is hydrogen, halogen, alkyl, alkenyl, alkynyl, aryl, heteroaryl, aralkyl, aralkyenyl, aralkynyl, heteroalkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, and sulfoxido;

R⁴ is absent, hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, and sulfoxido;

Y is —C($R_b$)$_2$— or —C(═O)—;

X is —O—, —N($R_a$)—, —C($R_b$)$_2$— or —S—;

Z is alkyl, haloalkyl or —C(═O)$R_b$;

$R_a$ is hydrogen, alkyl, aryl or aralkyl;

$R_b$ is hydrogen, alkyl or haloalkyl; and

----denotes a single bond, a cis double bond, or a trans double bond.

In further embodiments, an inhibitor of isomerohydrolase (IMH) has the structure of formula Ia, Ib, Ic, or Id, wherein R¹ is methyl.

In further embodiments, an inhibitor of isomerohydrolase (IMH) has the structure of formula Ia, Ib, Ic, or Id, wherein n is 0.

In further embodiments, an inhibitor of isomerohydrolase (IMH) has the structure of formula Ia, Ib, Ic, or Id, wherein n is 1.

In further embodiments, an inhibitor of isomerohydrolase (IMH) has the structure of formula Ia, Ib, Ic, or Id, wherein Y is —CH$_2$—.

In further embodiments, an inhibitor of isomerohydrolase (IMH) has the structure of formula Ia, Ib, Ic, or Id, wherein X is —O—.

In further embodiments, an inhibitor of isomerohydrolase (IMH) has the structure of formula Ia, Ib, Ic, or Id, wherein X is —N(H)—.

In further embodiments, an inhibitor of isomerohydrolase (IMH) has the structure of formula Ia, Ib, Ic, or Id, wherein Z is —C(═O)$R_b$.

In further embodiments, an inhibitor of isomerohydrolase (IMH) has the structure of formula Ia, Ib, Ic, or Id, wherein Z is —C(═O)$R_b$; and $R_b$ is haloalkyl.

In further embodiments, an inhibitor of isomerohydrolase (IMH) has the structure of formula Ia, Ib, Ic, or Id, wherein Z is alkyl.

In further embodiments, an inhibitor of isomerohydrolase (IMH) has the structure of formula Ia, Ib, Ic, or Id, wherein Z is haloalkyl.

In further embodiments, an inhibitor of isomerohydrolase (IMH) has the structure of formula Ia, Ib, Ic, or Id, wherein R³ is hydrogen.

In further embodiments, an inhibitor of isomerohydrolase (IMH) has the structure of formula Ia, Ib, Ic, or Id, wherein R⁴ is hydrogen, methyl or absent.

In certain embodiments, an inhibitor of isomerohydrolase (IMH) has a structure represented by formula Ie, If, Ig, or Ih:

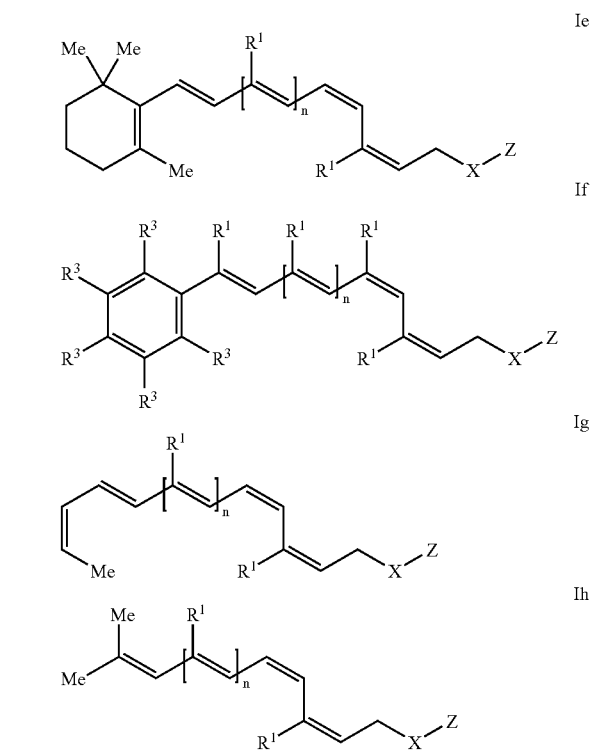

wherein, independently for each occurrence, n is 0 to 4 inclusive;

R¹ is hydrogen or alkyl;

R³ is hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, and sulfoxido;

X is —O—, —N($R_a$)—, —C($R_b$)$_2$— or —S—;

Z is alkyl, haloalkyl or —C(═O)$R_b$;

$R_a$ is hydrogen, alkyl, aryl or aralkyl; and $R_b$ is hydrogen, alkyl or haloalkyl.

In further embodiments, an inhibitor of isomerohydrolase (IMH) has the structure of formula Ie, If, Ig, or Ih, wherein n is 0.

In further embodiments, an inhibitor of isomerohydrolase (IMH) has the structure of formula Ie, If, Ig, or Ih, wherein n is 1.

In further embodiments, an inhibitor of isomerohydrolase (IMH) has the structure of formula Ie, If, Ig, or Ih, wherein X is —O—.

In further embodiments, an inhibitor of isomerohydrolase (IMH) has the structure of formula Ie, If, Ig, or Ih, wherein X is —N(H)—.

In further embodiments, an inhibitor of isomerohydrolase (IMH) has the structure of formula Ie, If, Ig, or Ih, wherein Z is —C(═O)$R_b$.

In further embodiments, an inhibitor of isomerohydrolase (IMH) has the structure of formula Ie, If, Ig, or Ih, wherein Z is —C(═O)$R_b$; and $R_b$ is haloalkyl.

In further embodiments, an inhibitor of isomerohydrolase (IMH) has the structure of formula Ie, If, Ig, or Ih, wherein Z is alkyl.

In further embodiments, an inhibitor of isomerohydrolase (IMH) has the structure of formula Ie, If, Ig, or Ih, wherein Z is haloalkyl.

In further embodiments, an inhibitor of isomerohydrolase (IMH) has the structure of formula Ie, If, Ig, or Ih, wherein $R^3$ is hydrogen.

In further embodiments, an inhibitor of isomerohydrolase (IMH) has the structure of formula Ie, If, Ig, or Ih, wherein X is —O—; and Z is alkyl.

In further embodiments, an inhibitor of isomerohydrolase (IMH) has the structure of formula Ie, If, Ig, or Ih, wherein X is —O—; and Z is haloalkyl.

In further embodiments, an inhibitor of isomerohydrolase (IMH) has the structure of formula Ie, If, Ig, or Ih, wherein X is —N(H)—; and Z is alkyl.

In further embodiments, an inhibitor of isomerohydrolase (IMH) has the structure of formula Ie, If, Ig, or Ih, wherein X is —N(H)—; and Z is haloalkyl.

In one embodiment, an inhibitor of isomerohydrolase (IMH) is 11-cis-retinyl bromoacetate (cBRA):

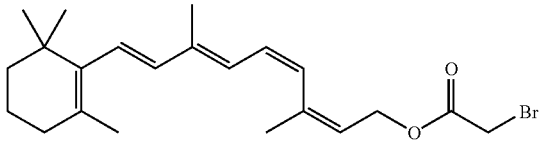

In certain embodiments, an inhibitor of isomerohydrolase (IMH), an inhibitor 11-cis-retinol dehydrogenase, an inhibitor of lecithin retinol acyl transferase (LRAT), or an antagonist of chaperone retinal pigment epithelium (RPE65) has a structure represented by formula II:

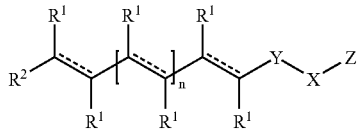

II wherein, independently for each occurrence, n is 0 to 10 inclusive;

$R^1$ is hydrogen or alkyl;

$R^2$ is hydrogen, alkyl, cycloalkyl, alkenyl, cycloalkenyl, alkynyl, aryl, or aralkyl;

Y is —C($R_b$)$_p$—, —C(=O)— or —C($R_b$)$_p$C(=O)—;

X is hydrogen, —O—, —S—, —N($R_a$)—, —N($R_a$)—N($R_a$)—, —C(=O)—, —C(=O)—, —C(=NR$_a$)—, —C(=NOH)—, —C(=S)— or —C($R_b$)$_p$—;

Z is absent, hydrogen, alkyl, haloalkyl, aryl, aralkyl, —CN, —O$R_b$, —(CH$_2$CH$_2$O)$_p$R$_b$, —C(=O)R$_b$, —C(=O)CH$_2$F, —C(=O)CHF$_2$, —C(=O)CF$_3$, —C(=O)CHN$_2$, —C(=O)OR$_b$, —C(=O)CH$_2$OC(=O)R$_b$, —C(=O)C(=C(R$_b$)$_2$)R$_b$,

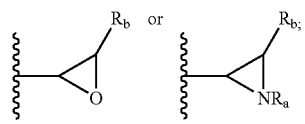

p is 0 to 20 inclusive;

$R_a$ is hydrogen, alkyl, aryl or aralkyl;

$R_b$ is hydrogen, alkyl, haloalkyl, aryl or aralkyl; and

----denotes a single bond, a cis double bond or a trans double bond.

In certain embodiments, an inhibitor of lecithin retinol acyl transferase (LRAT) has a structure represented by formula IIa, IIb, IIc, or IId:

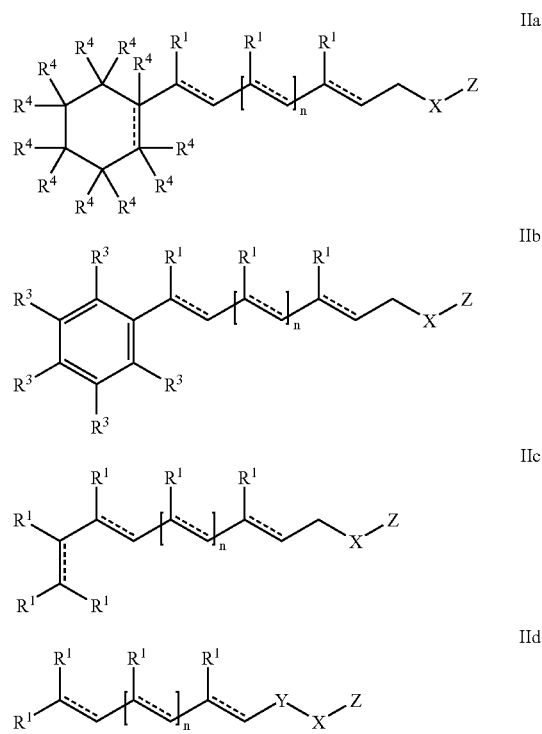

wherein, independently for each occurrence, n is 0 to 4 inclusive;

$R^1$ is hydrogen or alkyl;

$R^3$ is hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, and sulfoxido;

$R^4$ is absent, hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, and sulfoxido;

Y is —C(=O)— or —C(R$_b$)$_2$—;

X is hydrogen, —O—, —S—, —N($R_a$)—, —N($R_a$)—N($R_a$)—, —C(=O)—, —C(=NR$_a$)—, —C(=NOH)—, —C(=S)— or —C($R_b$)$_2$—;

Z is absent, hydrogen, alkyl, haloalkyl, aryl, aralkyl, —CN, —O$R_b$, —C(=O)R$_b$, —C(=O)CH$_2$F, —C(=O)CHF$_2$, —C(=O)CF$_3$, —C(=O)CHN$_2$, —C(=O)CH$_2$OC(=O)R$_b$, —C(=O)OR$_b$, —C(=O)C(=C(R$_b$)$_2$)R$_b$,

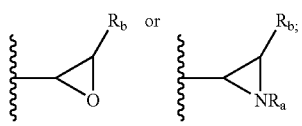

$R_a$ is hydrogen, alkyl, aryl or aralkyl;
$R_b$ is hydrogen, alkyl, haloalkyl, aryl or aralkyl; and
----denotes a single bond, a cis double bond or a trans double bond.

In further embodiments, an inhibitor of lecithin retinol acyl transferase (LRAT) has a structure represented by formula IIa, IIb, IIc, or IId, wherein n is 0.

In further embodiments, an inhibitor of lecithin retinol acyl transferase (LRAT) has a structure represented by formula IIa, IIb, IIc, or IId, wherein n is 1.

In further embodiments, an inhibitor of lecithin retinol acyl transferase (LRAT) has a structure represented by formula IIa, IIb, IIc, or IId, wherein $R^1$ is hydrogen or methyl.

In further embodiments, an inhibitor of lecithin retinol acyl transferase (LRAT) has a structure represented by formula IIa, IIb, IIc, or IId, wherein $R^3$ is hydrogen.

In further embodiments, an inhibitor of lecithin retinol acyl transferase (LRAT) has a structure represented by formula IIa, IIb, IIc, or IId, wherein $R^4$ is hydrogen or methyl.

In further embodiments, an inhibitor of lecithin retinol acyl transferase (LRAT) has a structure represented by formula IIa, IIb, IIc, or IId, wherein Y is —CH$_2$—

In further embodiments, an inhibitor of lecithin retinol acyl transferase (LRAT) has a structure represented by formula IIa, IIb, IIc, or IId, wherein X is —O—.

In further embodiments, an inhibitor of lecithin retinol acyl transferase (LRAT) has a structure represented by formula IIa, IIb, IIc, or IId, wherein X is —NH—.

In further embodiments, an inhibitor of lecithin retinol acyl transferase (LRAT) has a structure represented by formula IIa, IIb, IIc, or IId, wherein X is —C(R$_b$)$_2$—.

In further embodiments, an inhibitor of lecithin retinol acyl transferase (LRAT) has a structure represented by formula IIa, IIb, IIc, or IId, wherein X is —C(=O)—.

In further embodiments, an inhibitor of lecithin retinol acyl transferase (LRAT) has a structure represented by formula IIa, IIb, IIc, or IId, wherein Z is alkyl.

In further embodiments, an inhibitor of lecithin retinol acyl transferase (LRAT) has a structure represented by formula IIa, IIb, IIc, or IId, wherein Z is haloalkyl.

In certain embodiments, an inhibitor of lecithin retinol acyl transferase (LRAT) has a structure represented by formula IIe, IIf, IIg, or IIh:

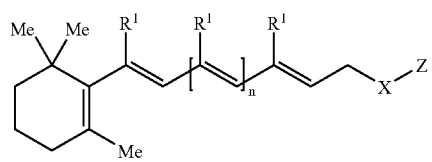

IIe

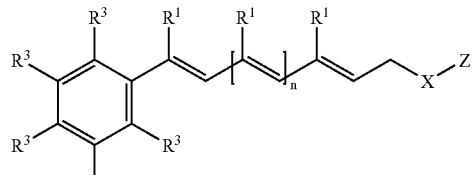

IIf

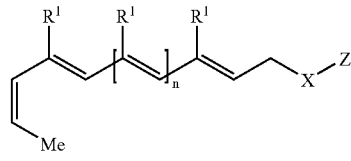

IIg

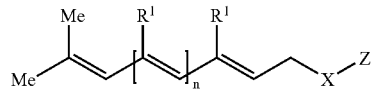

IIh wherein, independently for each occurrence,
n is 0 to 4 inclusive;
$R^1$ is hydrogen or alkyl;
$R^3$ is hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, and sulfoxido;
X is hydrogen, —O—, —S—, —N(R$_a$)—, —N(R$_a$)—N(R$_a$)—, —C(=O)—, —C(=NR$_a$)—, —C(=NOH)—, —C(=S)— or —C(R$_b$)$_2$—;
Z is absent, hydrogen, alkyl, haloalkyl, aryl, aralkyl, —CN, —OR$_b$, —C(=O)R$_b$, —C(=O)CH$_2$F, —C(=O)CHF$_2$, —C(=O)CF$_3$, —C(=O)CHN$_2$, —C(=O)CH$_2$OC(=O)R$_b$, —C(=O)OR$_b$, —C(=O)C(=C(R$_b$)$_2$)R$_b$,

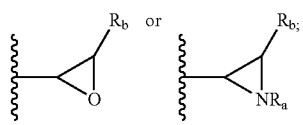

$R_a$ is hydrogen, alkyl, aryl or aralkyl; and
$R_b$ is hydrogen, alkyl, haloalkyl, aryl or aralkyl.

In further embodiments, an inhibitor of lecithin retinol acyl transferase (LRAT) has a structure represented by formula IIe, IIf, IIg, or IIh, wherein n is 0.

In further embodiments, an inhibitor of lecithin retinol acyl transferase (LRAT) has a structure represented by formula IIe, IIf, IIg, or IIh, wherein n is 1.

In further embodiments, an inhibitor of lecithin retinol acyl transferase (LRAT) has a structure represented by formula IIe, IIf, IIg, or IIh, wherein $R^1$ is hydrogen or methyl.

In further embodiments, an inhibitor of lecithin retinol acyl transferase (LRAT) has a structure represented by formula IIe, IIf, IIg, or IIh, wherein $R^3$ is hydrogen.

In further embodiments, an inhibitor of lecithin retinol acyl transferase (LRAT) has a structure represented by formula IIe, IIf, IIg, or IIh, wherein $R^4$ is hydrogen or methyl.

In further embodiments, an inhibitor of lecithin retinol acyl transferase (LRAT) has a structure represented by formula IIe, IIf, IIg, or IIh, wherein X is —O—.

In further embodiments, an inhibitor of lecithin retinol acyl transferase (LRAT) has a structure represented by formula IIe, IIf, IIg, or IIh, wherein X is —NH—.

In further embodiments, an inhibitor of lecithin retinol acyl transferase (LRAT) has a structure represented by formula IIe, IIf, IIg, or IIh, wherein X is —CH$_2$—.

In further embodiments, an inhibitor of lecithin retinol acyl transferase (LRAT) has a structure represented by formula IIe, IIf, IIg, or IIh, wherein X is —C(=O)—.

In further embodiments, an inhibitor of lecithin retinol acyl transferase (LRAT) has a structure represented by formula IIe, IIf, IIg, or IIh, wherein Z is alkyl.

In further embodiments, an inhibitor of lecithin retinol acyl transferase (LRAT) has a structure represented by formula IIe, IIf, IIg, or IIh, wherein Z is haloalkyl.

In further embodiments, an inhibitor of lecithin retinol acyl transferase (LRAT) has a structure represented by formula IIe, IIf, IIg, or IIh, wherein Z is —C(=O)R$_b$.

In further embodiments, an inhibitor of lecithin retinol acyl transferase (LRAT) has a structure represented by formula IIe, IIf, IIg, or IIh, wherein X is —O—; and Z is —C(=O)R$_b$.

In further embodiments, an inhibitor of lecithin retinol acyl transferase (LRAT) has a structure represented by formula IIe, IIf, IIg, or IIh, wherein X is —CH$_2$—; and Z is —C(=O)R$_b$.

In further embodiments, an inhibitor of lecithin retinol acyl transferase (LRAT) has a structure represented by formula IIe, IIf, IIg, or IIh, wherein X is —NH—; and Z is —C(=O)R$_b$.

In one embodiment, an inhibitor of lecithin retinol acyl transferase (LRAT) is 13-desmethyl-13,14-dihydro-all-trans-retunyl trifluoroacetate (RFA):

In one embodiment, an inhibitor of lecithin retinol acyl transferase (LRAT) is all-trans-retinyl α-bromoacetate.

In certain embodiments, an inhibitor of isomerohydrolase (IMH), an inhibitor 11-cis-retinol dehydrogenase, an inhibitor of lecithin retinol acyl transferase (LRAT), or an antagonist of chaperone retinal pigment epithelium (RPE65) has a structure represented by formula III:

III wherein, independently for each occurrence, n is 0 to 10 inclusive;

R$^1$ is hydrogen or alkyl;

R$^2$ is hydrogen, alkyl, cycloalkyl, alkenyl, cycloalkenyl, alkynyl, aryl, or aralkyl;

Y is —CR$_b$(OR$_b$)—, —CR$_b$(N(R$_a$)$_2$)—, —C(R$_b$)$_p$—, —C(=O)— or —C(R$_b$)$_p$C(=O)—;

X is —O—, —S—, —N(R$_a$)—, —C(=O)—, or —C(R$_b$)$_p$—;

Z is hydrogen, alkyl, haloalkyl, aryl, aralkyl, —OR$_b$, —N(R$_b$)$_2$, —(CH$_2$CH$_2$O)$_p$R$_b$, —C(=O)R$_b$, —C(=NR$_a$)R$_b$, —C(=NOR$_b$)R$_b$, —C(OR$_b$)(R$_b$)$_2$, —C(N(R$_a$)$_2$)(R$_b$)$_2$ or —(CH$_2$CH$_2$O)$_p$R$_b$;

p is 0 to 20 inclusive;

R$_a$ is hydrogen, alkyl, aryl or aralkyl;

R$_b$ is hydrogen, alkyl, haloalkyl, aryl or aralkyl; and

----denotes a single bond or a trans double bond.

In certain embodiments, an antagonist of retinal pigment epithelium (RPE65) has a structure represented by formula IIIa, IIIb, IIIc or IIId:

IIIa

IIIb

IIIc

IIId wherein, independently for each occurrence, n is 0 to 4 inclusive;

R$^1$ is hydrogen or alkyl;

Y is —C(=O)—, —CR$_b$(OR$_b$)—, —CR$_b$(N(R$_a$)$_2$)— or —C(R$_b$)$_2$—;

X is —O—, —S—, —N(R$_a$)—, —C(=O)—, or —C(R$_b$)$_2$—;

Z is hydrogen, alkyl, haloalkyl, aryl, aralkyl, —OR$_b$, —N(R$_b$)$_2$, —C(=O)R$_b$, —C(=NR$_a$)R$_b$, —C(=NOH)R$_b$, —C(OR$_b$)(R$_b$)$_2$, —C(N(R$_a$)$_2$)(R$_b$)$_2$ or —(CH$_2$CH$_2$O)$_p$R$_b$;

R$_a$ is hydrogen, alkyl, aryl or aralkyl;

R$_b$ is hydrogen, alkyl, haloalkyl, aryl or aralkyl;

p is 0 to 10 inclusive; and

----denotes a single bond or a trans double bond.

In further embodiments, an antagonist of retinal pigment epithelium (RPE65) has a structure represented by formula IIIa, IIIb, IIIc, or IIId, wherein n is 0.

In further embodiments, an antagonist of retinal pigment epithelium (RPE65) has a structure represented by formula IIIa, IIIb, IIIc, or IIId, wherein n is 1.

In further embodiments, an antagonist of retinal pigment epithelium (RPE65) has a structure represented by formula IIIa, IIIb, IIIc, or IIId, wherein R$^1$ is hydrogen or methyl.

In further embodiments, an antagonist of retinal pigment epithelium (RPE65) has a structure represented by formula IIIa, IIIb, IIIc, or IIId, wherein $R^3$ is hydrogen.

In further embodiments, an antagonist of retinal pigment epithelium (RPE65) has a structure represented by formula IIIa, IIIb, IIIc, or IIId, wherein $R^4$ is hydrogen or methyl.

In further embodiments, an antagonist of retinal pigment epithelium (RPE65) has a structure represented by formula IIIa, IIIb, IIIc, or IIId, wherein X is —O—.

In further embodiments, an antagonist of retinal pigment epithelium (RPE65) has a structure represented by formula IIIa, IIIb, IIIc, or IIId, wherein X is —NH—.

In further embodiments, an antagonist of retinal pigment epithelium (RPE65) has a structure represented by formula IIIa, IIIb, IIIc, or IIId, wherein X is —C($R_b$)$_2$—.

In further embodiments, an antagonist of retinal pigment epithelium (RPE65) has a structure represented by formula IIIa, IIIb, IIIc, or IIId, wherein X is —C(=O)—.

In further embodiments, an antagonist of retinal pigment epithelium (RPE65) has a structure represented by formula IIIa, IIIb, IIIc, or IIId, wherein Z is alkyl.

In further embodiments, an antagonist of retinal pigment epithelium (RPE65) has a structure represented by formula IIIa, IIIb, IIIc, or IIId, wherein Z is haloalkyl.

In certain embodiments, an antagonist of retinal pigment epithelium (RPE65) has a structure represented by formula IIIe, IIIf, IIIg, or IIIh:

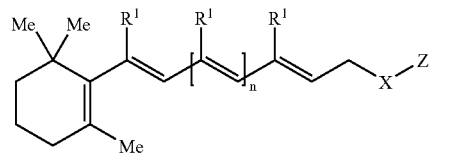

IIIe

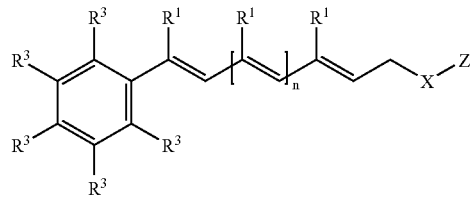

IIIf

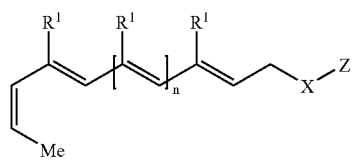

IIIg

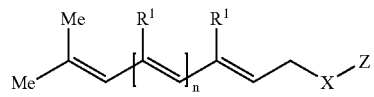

IIIh wherein, independently for each occurrence,
n is 0 to 4 inclusive;
$R^1$ is hydrogen or alkyl;
X is —O—, —S—, —N($R_a$)—, —C(=O)—, or —C($R_b$)$_2$—;
Z is hydrogen, alkyl, haloalkyl, aryl, aralkyl, —O$R_b$, —N($R_b$)$_2$, —C(=O)$R_b$, —C(=N$R_a$)$R_b$, —C(=NOH)$R_b$, —C(O$R_b$)($R_b$)$_2$, —C(N($R_a$)$_2$)($R_b$)$_2$ or —(CH$_2$CH$_2$O)$_p$$R_b$;
$R_a$ is hydrogen, alkyl, aryl or aralkyl;
$R_b$ is hydrogen, alkyl, haloalkyl, aryl or aralkyl; and
p is 0 to 10 inclusive.

In further embodiments, an antagonist of retinal pigment epithelium (RPE65) has a structure represented by formula IIIe, IIIf, IIIg, or IIIh, wherein n is 0.

In further embodiments, an antagonist of retinal pigment epithelium (RPE65) has a structure represented by formula IIIe, IIIf, IIIg, or IIIh, wherein n is 1.

In further embodiments, an antagonist of retinal pigment epithelium (RPE65) has a structure represented by formula IIIe, IIIf, IIIg, or IIIh, wherein $R^1$ is hydrogen or methyl.

In further embodiments, an antagonist of retinal pigment epithelium (RPE65) has a structure represented by formula IIIe, IIIf, IIIg, or IIIh, wherein Y is —C(=O)—.

In further embodiments, an antagonist of retinal pigment epithelium (RPE65) has a structure represented by formula IIIe, IIIf, IIIg, or IIIh, wherein Y is —CH$_2$—.

In further embodiments, an antagonist of retinal pigment epithelium (RPE65) has a structure represented by formula IIIe, IIIf, IIIg, or IIIh, wherein Z is —C(=O)$R_b$.

In further embodiments, an antagonist of retinal pigment epithelium (RPE65) has a structure represented by formula IIIe, IIIf, IIIg, or IIIh, wherein Z is —CH(OH)$R_b$—.

In further embodiments, an antagonist of retinal pigment epithelium (RPE65) has a structure represented by formula IIIe, IIIf, IIIg, or IIIh, wherein Z is CH(NH)$R_b$.

In further embodiments, an antagonist of retinal pigment epithelium (RPE65) has a structure represented by formula IIIe, IIIf, IIIg, or IIIh, wherein Z is alkyl.

In further embodiments, an antagonist of retinal pigment epithelium (RPE65) has a structure represented by formula IIIe, IIIf, IIIg, or IIIh, wherein Z is haloalkyl.

In one embodiment, an antagonist of retinal pigment epithelium (RPE65) is 13-cis-retinoic acid (isoretinoin, ACCUTANE®):

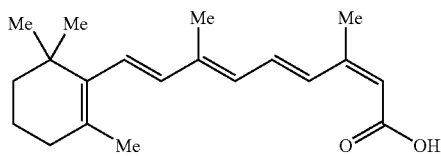

In certain embodiments, an antagonist of retinal pigment epithelium (RPE65) has a structure represented by formula IV:

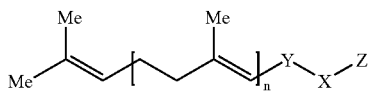

IV wherein, independently for each occurrence,
n is 1, 2, 3 or 4;
Y is —C($R_b$)$_2$—, —C(=O)— or —OC(=O)—;
X is —O—, —N$R_a$—, —C($R_b$)$_2$— or —C(=O)—;
Z is —C(=O)$R_b$, —O$R_b$, —N($R_b$)$_2$, alkyl or haloalkyl;
$R_a$ is hydrogen, alkyl, haloalkyl, aryl or aralkyl; and
$R_b$ is hydrogen, alkyl, haloalkyl, aryl or aralkyl.

In further embodiments, an inhibitor of retinal pigment epithelium (RPE65) has a structure represented by formula IV, wherein Y is —CH$_2$—.

In further embodiments, an antagonist of retinal pigment epithelium (RPE65) has a structure represented by formula IV, wherein X is —O—.

In further embodiments, an antagonist of retinal pigment epithelium (RPE65) has a structure represented by formula IV, wherein Z is —C(=O)R$_b$; and R$_b$ is alkyl.

In further embodiments, an antagonist of retinal pigment epithelium (RPE65) has a structure represented by formula IV, wherein Z is alkyl.

In further embodiments, an antagonist of retinal pigment epithelium (RPE65) has a structure represented by formula IV, wherein Y is —CH$_2$—; X is —O—; Z is —C(=O)R$_b$; and R$_b$ is alkyl.

In further embodiments, an antagonist of retinal pigment epithelium (RPE65) has a structure represented by formula IV, wherein Y is —CH$_2$—; X is —O—; and Z is alkyl.

In further embodiments, an antagonist of retinal pigment epithelium (RPE65) has a structure represented by formula IV, wherein Y is —CH$_2$—; X is —C(=O)—; and Z is alkyl.

In further embodiments, an antagonist of retinal pigment epithelium (RPE65) has a structure represented by formula IV, wherein Y is —CH$_2$—; X is —C(=O)—; Z is —N(R$_b$)$_2$; and R$_b$ is alkyl.

In one embodiment, an antagonist of retinal pigment epithelium (RPE65) is geranyl palmitate (K$_D$=301 nM):

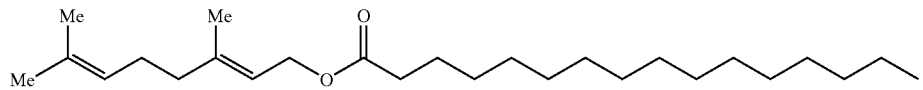

In one embodiment, an antagonist of retinal pigment epithelium (RPE65) is farnesyl palmitate (K$_D$=63 nM)

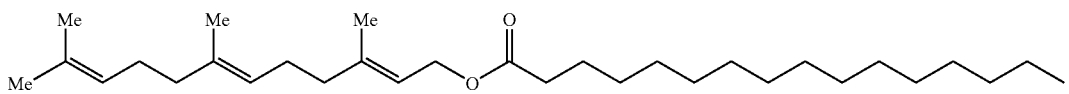

In one embodiment, an antagonist of retinal pigment epithelium (RPE65) is geranylgeranyl palmitate (K$_D$=213 nM):

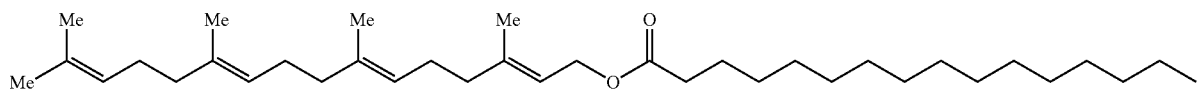

In one embodiment, an antagonist of retinal pigment epithelium (RPE65) is geranyl palmityl ether (K$_D$=416 nM):

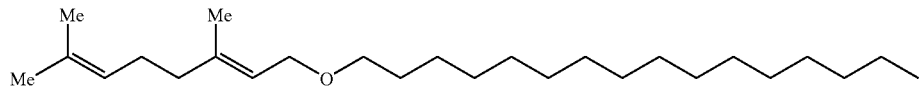

In one embodiment, an antagonist of retinal pigment epithelium (RPE65) is farnesyl palmityl ether ($K_D$=60 nM):

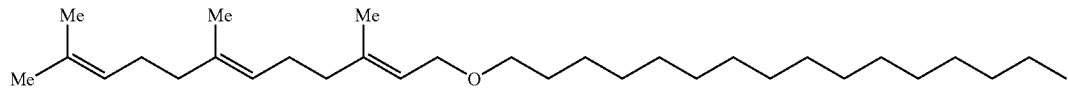

10

In one embodiment, an antagonist of retinal pigment epithelium (RPE65) is geranylgeranyl palmityl ether ($K_D$=195 nM):

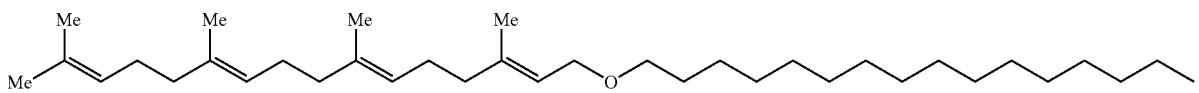

In one embodiment, an antagonist of retinal pigment epithelium (RPE65) is the following compound:

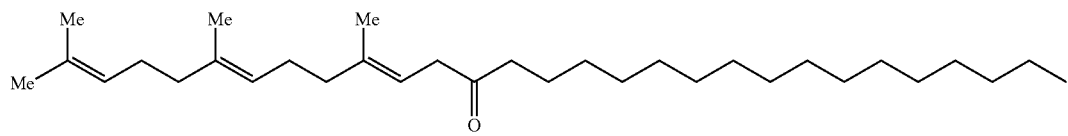

In one embodiment, an antagonist of retinal pigment epithelium (RPE65) is the following compound ($K_D$=96 nM):

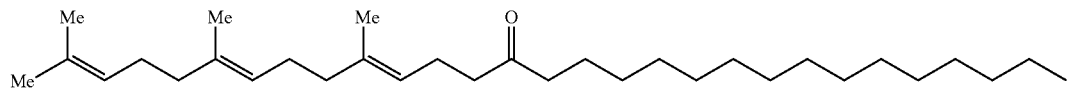

In one embodiment, an antagonist of retinal pigment epithelium (RPE65) is the following compound:

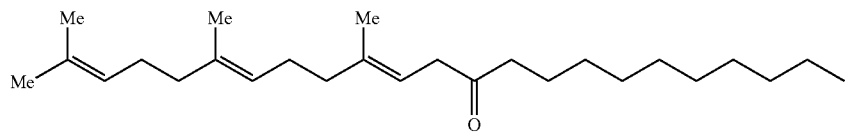

In one embodiment, an antagonist of retinal pigment epithelium (RPE65) is the following compound ($K_D$=56 nM):

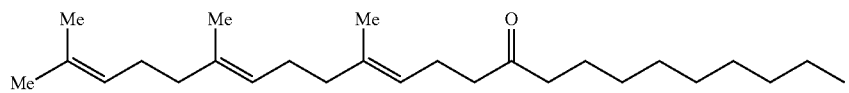

In one embodiment, an antagonist of retinal pigment epithelium (RPE65) is farnesyl octyl ketone:

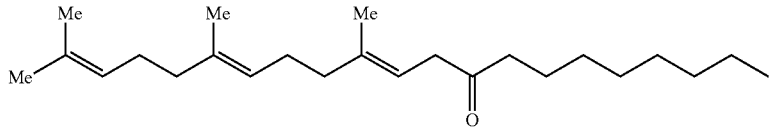

In one embodiment, an antagonist of retinal pigment epithelium (RPE65) is octyl farnesimide:

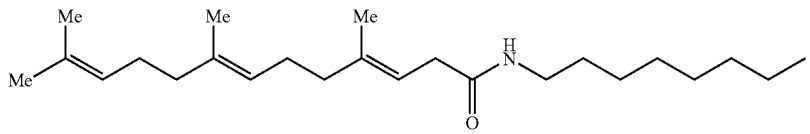

In one embodiment, an antagonist of retinal pigment epithelium (RPE65) is palmityl farnesimide:

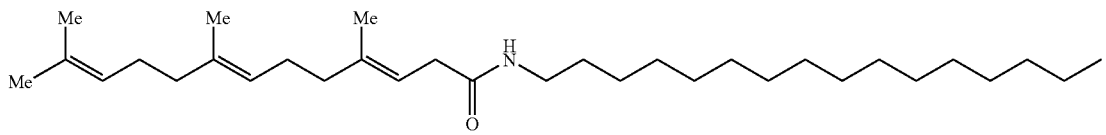

In one embodiment, an antagonist of retinal pigment epithelium (RPE65) is the following compound ($K_D$=56 nM):

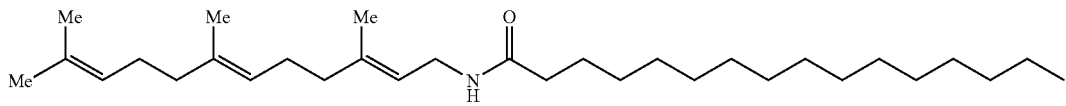

In one embodiment, an antagonist of retinal pigment epithelium (RPE65) is the following compound ($K_D$=58±5 nM), called 13,17,21-Trimethyl-docosa-12,16,20-trien-11-one or "TDT":

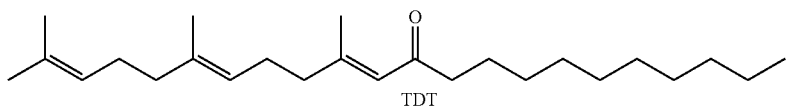

TDT

In one embodiment, an antagonist of retinal pigment epithelium (RPE65) is the following compound ($K_D$=96±14 nM), called 3,7,11-Trimethyl-dodeca-2,6,10-trienoic acid hexadecylamide or "TDH":

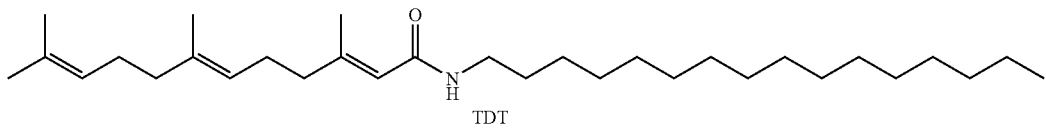
TDT

In certain embodiments, an antagonist of retinal pigment epithelium (RPE65) has a structure represented by formula V:

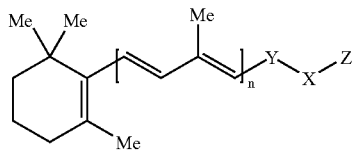

wherein, independently for each occurrence,
n is 1, 2 or 3;
Y is —C(R$_b$)$_2$—, —C(=O)— or —CH(OH)—;
X is —O—, —NR$_a$— or —C(R$_b$)$_2$—;
Z is —C(=O)R$_b$, hydrogen, —(CH$_2$CH$_2$O)$_p$R$_b$, alkyl or haloalkyl;
R$_a$ is hydrogen, alkyl, haloalkyl, aryl or aralkyl;
R$_b$ is hydrogen, alkyl, haloalkyl, aryl or aralkyl; and
p is 1 to 10 inclusive.

In further embodiments, an antagonist of retinal pigment epithelium (RPE65) has a structure represented by formula V, wherein Y is —CH$_2$—.

In further embodiments, an antagonist of retinal pigment epithelium (RPE65) has a structure represented by formula V, wherein Y is —C(=O)—.

In further embodiments, an antagonist of retinal pigment epithelium (RPE65) has a structure represented by formula V, wherein Y is —CH(OH)—.

In further embodiments, an antagonist of retinal pigment epithelium (RPE65) has a structure represented by formula V, wherein X is —O—.

In further embodiments, an antagonist of retinal pigment epithelium (RPE65) has a structure represented by formula V, wherein X is —NR$_a$—

In further embodiments, an antagonist of retinal pigment epithelium (RPE65) has a structure represented by formula V, wherein X is —C(R$_b$)—.

In further embodiments, an antagonist of retinal pigment epithelium (RPE65) has a structure represented by formula V, wherein Z is alkyl.

In further embodiments, an antagonist of retinal pigment epithelium (RPE65) has a structure represented by formula V, wherein Z is —C(=O)R$_b$; and R$_b$ is alkyl.

In further embodiments, an antagonist of retinal pigment epithelium (RPE65) has a structure represented by formula V, wherein Z is —(CH$_2$CH$_2$O)$_p$R$_b$; and R$_b$ is alkyl.

In one embodiment, an antagonist of retinal pigment epithelium (RPE65) is β-ionoacetyl palmitate ($K_D$=153 nM):

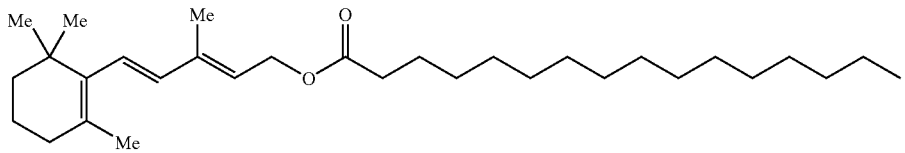

In one embodiment, an antagonist of retinal pigment epithelium (RPE65) is β-ionoacetyl palmityl ether ($K_D$=156 nM):

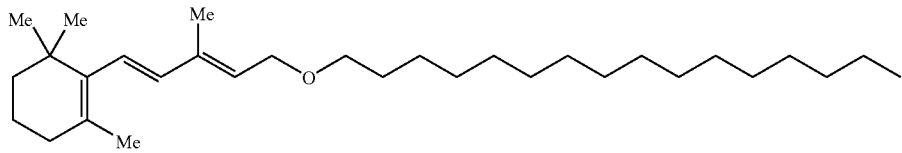

In one embodiment, an antagonist of retinal pigment epithelium (RPE65) is retinyl palmitate (4a; $K_D$=47 nM):

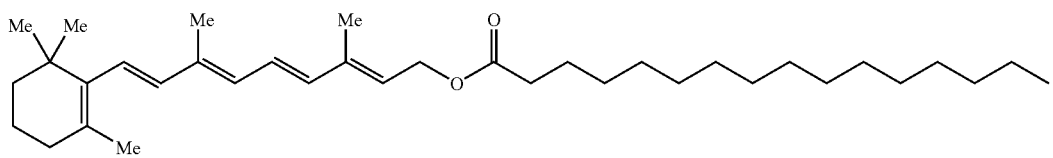

In one embodiment, an antagonist of retinal pigment epithelium (RPE65) is retinyl hexanoate (4b; $K_D$=235 nM):

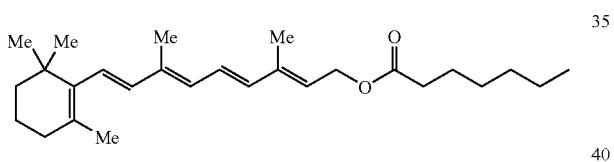

In one embodiment, an antagonist of retinal pigment epithelium (RPE65) is retinyl pentanoate:

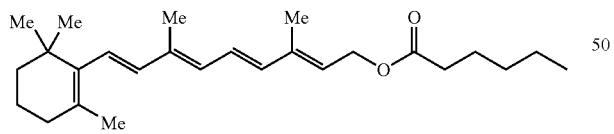

In one embodiment, an antagonist of retinal pigment epithelium (RPE65) is retinyl acetate (4c; $K_D$=1,300 nM):

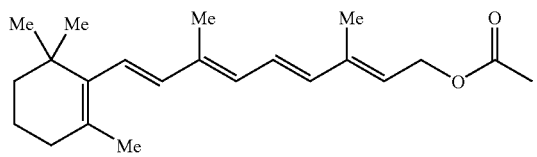

In one embodiment, an antagonist of retinal pigment epithelium (RPE65) is palmityl retinyl ether (4d, $K_D$=25 nM):

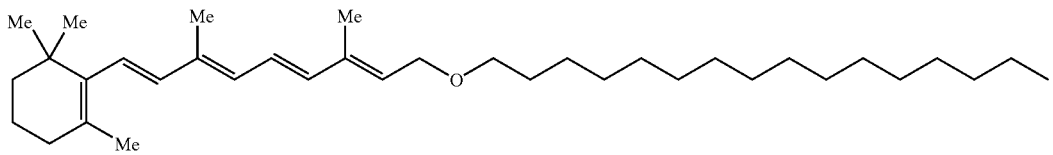

In one embodiment, an antagonist of retinal pigment epithelium (RPE65) is hexyl retinyl ether ($K_D$=151 nM):

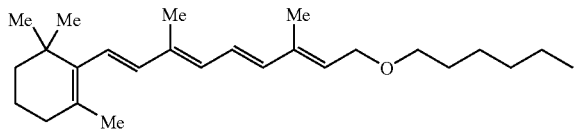

In one embodiment, an antagonist of retinal pigment epithelium (RPE65) is methyl retinyl ether ($K_D$=24 nM):

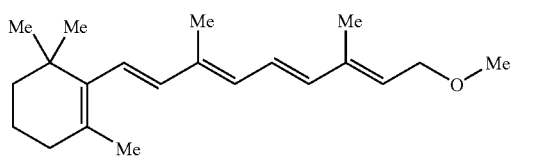

In one embodiment, an antagonist of retinal pigment epithelium (RPE65) is retinyl [2-(2'-methoxy)ethoxy]ethyl ether ($K_D$=486 nM):

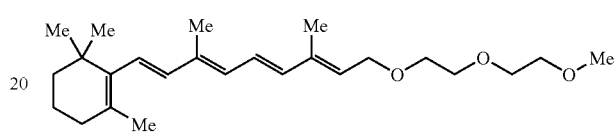

In one embodiment, an antagonist of retinal pigment epithelium (RPE65) is:

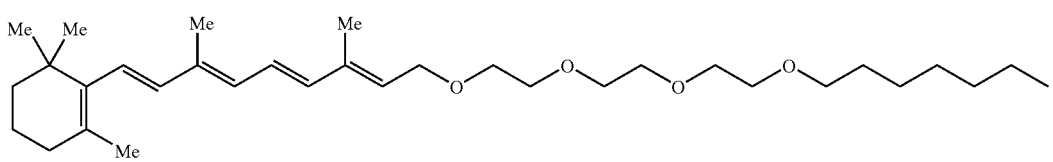

In one embodiment, an antagonist of retinal pigment epithelium (RPE65) is N-palmityl retinimide ($K_D$=40 nM):

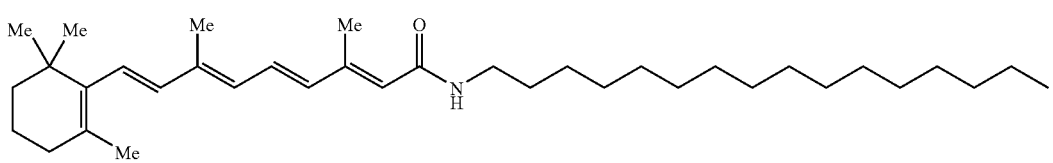

In one embodiment, an antagonist of retinal pigment epithelium (RPE65) is N,N-dimethyl retinimide ($K_D$=3,577 nM):

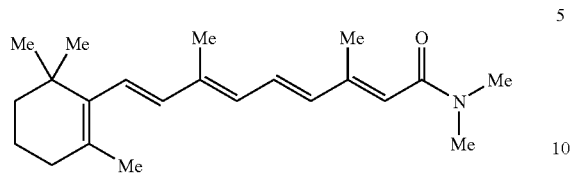

In one embodiment, an antagonist of retinal pigment epithelium (RPE65) is N-tert-butyl retinimide ($K_D$=4,321 nM):

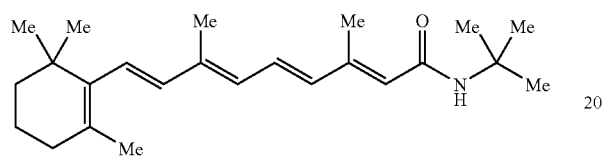

In one embodiment, an antagonist of retinal pigment epithelium (RPE65) is palmityl retinyl alcohol ($K_D$=170 nM):

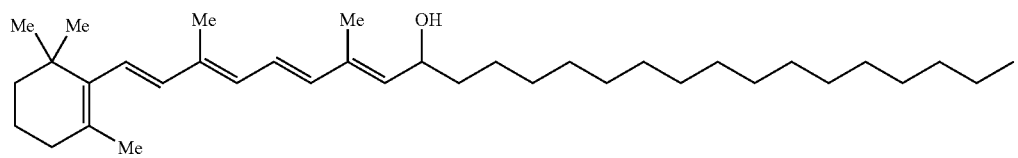

In one embodiment, an antagonist of retinal pigment epithelium (RPE65) is methyl retinyl alcohol:

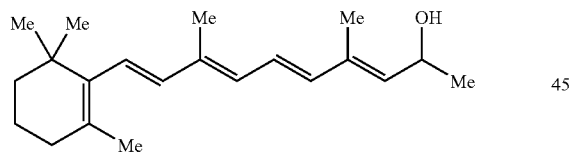

In one embodiment, an antagonist of retinal pigment epithelium (RPE65) is palmityl retinyl ketone ($K_D$=64 nM):

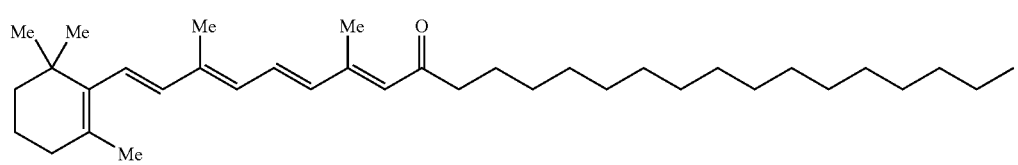

In one embodiment, an antagonist of retinal pigment epithelium (RPE65) is retinyl decyl ketone:

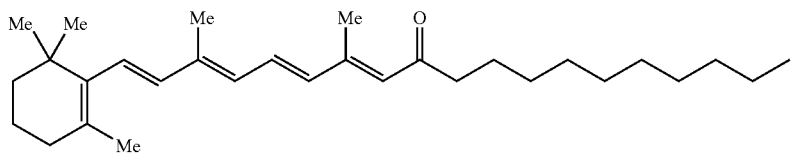

In one embodiment, an antagonist of retinal pigment epithelium (RPE65) is methyl retinyl ketone ($K_D$=3,786 nM):

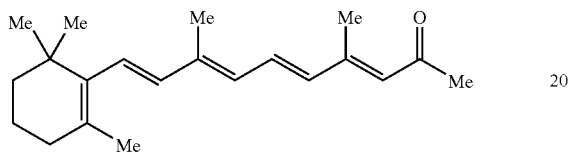

In one embodiment, an antagonist of retinal pigment epithelium (RPE65) is the following compound (4e):

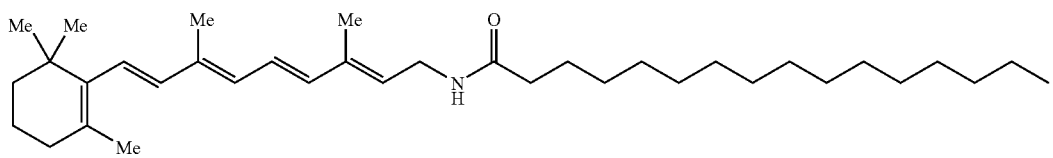

In one embodiment, an antagonist of retinal pigment epithelium (RPE65) is the following compound (4f; $K_D$=64 nM)

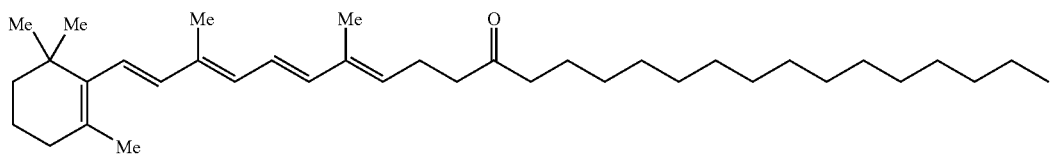

In one embodiment, an antagonist of retinal pigment epithelium (RPE65) is the following compound ($K_D$=173 nM):

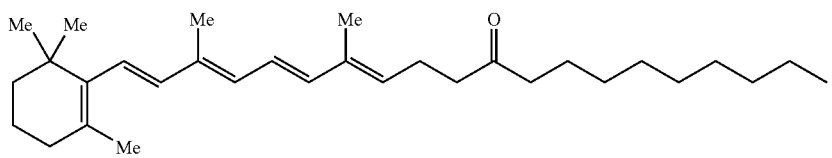

In one embodiment, an antagonist of retinal pigment epithelium (RPE65) is the following compound ($K_D$=3,786 nM):

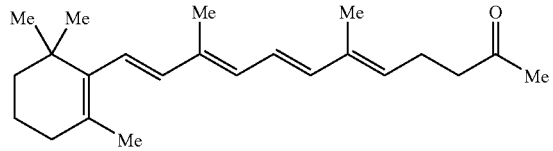

In one embodiment, an antagonist of retinal pigment epithelium (RPE65) is:

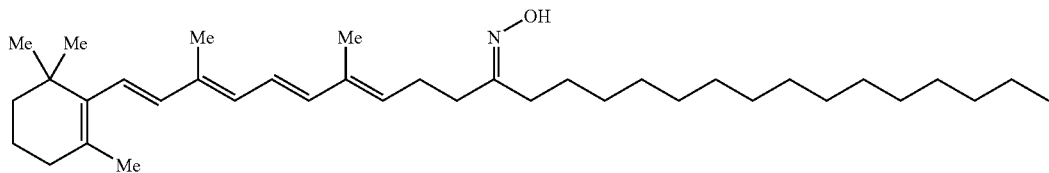

In one embodiment, an antagonist of retinal pigment epithelium (RPE65) is:

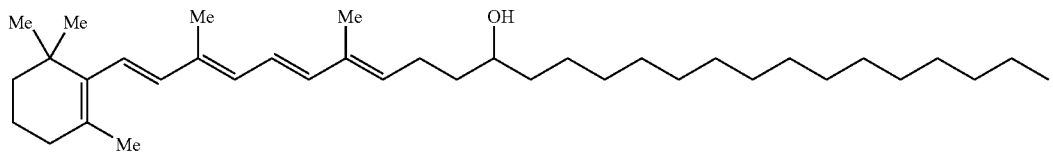

In one embodiment, an antagonist of retinal pigment epithelium (RPE65) is:

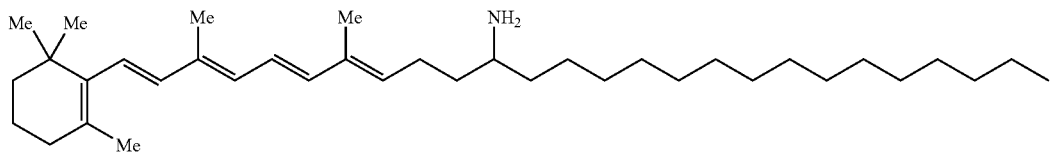

The above-described RPE65 antagonist compounds and general formulas of compounds, with their various substituent definitions and further embodiments, are also LRAT inhibitors, and are incorporated herein by reference as LRAT inhibitors.

Other antagonists of RPE65 and inhibitors of LRAT include agents that inhibit palmitoylation. For example, 2-bromopalmitate inhibits palmitoylation. In some embodiments, a racemic mixture of 2-bromopalmitate may be applied to inhibit LRAT and/or antagonize RPE65. In other embodiments, purified (R)-2-bromopalmitic acid may be applied to inhibit LRAT and/or antagonize RPE65. In yet other embodiments, purified (S)-2-bromopalmitic acid may be applied to inhibit LRAT and/or antagonize RPE65.

In certain embodiments, an inhibitor of 11-cis-retinol dehydrogenase has a structure represented by formula VI:

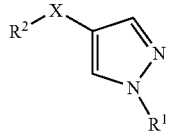

wherein, independently for each occurrence, $R^1$ is hydrogen, alkyl, aryl or aralkyl;

X is alkyl, alkenyl, —C($R_b$)$_2$—, —C(=O)—, —C(=N$R_a$)—, —C(OH)$R_b$ or —C(N($R_a$)$_2$)$R_b$—;

$R^2$ is hydrogen, alkyl, cycloalkyl, alkenyl, cycloalkenyl, alkynyl, aryl, or aralkyl;

$R_a$ is hydrogen, alkyl, aryl or aralkyl; and
$R_b$ is hydrogen or alkyl.

In further embodiments, an inhibitor of 11-cis-retinol dehydrogenase has a structure represented by formula VI, wherein $R^1$ is hydrogen.

In further embodiments, an inhibitor of 11-cis-retinol dehydrogenase has a structure represented by formula VI, wherein X is —C($R_b$)$_2$—.

In further embodiments, an inhibitor of 11-cis-retinol dehydrogenase has a structure represented by formula VI, wherein X is —C(=O)—.

In certain embodiments, an inhibitor of 11-cis-retinol dehydrogenase has a structure represented by formula VIa or VIb:

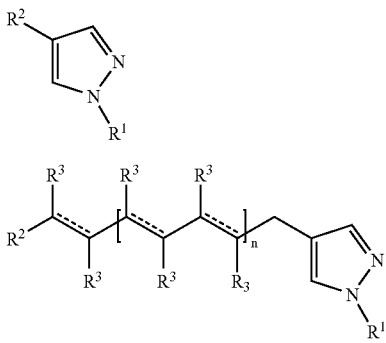

wherein, independently for each occurrence,
R¹ is hydrogen, alkyl, aryl or aralkyl;
R² is hydrogen, alkyl, cycloalkyl, alkenyl, cycloalkenyl, alkynyl, aryl, or aralkyl;
R³ is hydrogen or alkyl;
$R_a$ is hydrogen, alkyl, aryl or aralkyl;
$R_b$ is hydrogen or alkyl; and
----denotes a single bond, a cis double bond, or a trans double bond.

In further embodiments, an inhibitor of 11-cis-retinol dehydrogenase has a structure represented by formula VIa or VIb, wherein R¹ is hydrogen.

In further embodiments, an inhibitor of 11-cis-retinol dehydrogenase has a structure represented by formula VIa or VIb, wherein R² is alkyl.

In further embodiments, an inhibitor of 11-cis-retinol dehydrogenase has a structure represented by formula VIa or VIb, wherein R³ is hydrogen or methyl.

In certain embodiments, an inhibitor of 11-cis-retinol dehydrogenase has a structure represented by formula VIc, VId or VIe:

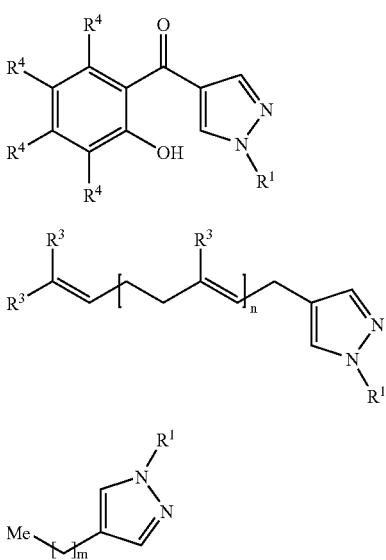

wherein, independently for each occurrence,
n is 1 to 5 inclusive;
m is 0 to 30 inclusive;
R¹ is hydrogen, alkyl, aryl or aralkyl;
R² is hydrogen, alkyl, cycloalkyl, alkenyl, cycloalkenyl, alkynyl, aryl, or aralkyl;
R³ is hydrogen or alkyl;
R⁴ is hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, and sulfoxido;
$R_a$ is hydrogen, alkyl, aryl or aralkyl; and
$R_b$ is hydrogen or alkyl.

In further embodiments, an inhibitor of 11-cis-retinol dehydrogenase has a structure represented by formula VIc, wherein R¹ is hydrogen.

In further embodiments, an inhibitor of 11-cis-retinol dehydrogenase has a structure represented by formula VIc, wherein R⁴ is hydrogen.

In further embodiments, an inhibitor of 11-cis-retinol dehydrogenase has a structure represented by formula VIc, wherein R¹ is hydrogen; and R⁴ is hydrogen.

In further embodiments, an inhibitor of 11-cis-retinol dehydrogenase has a structure represented by formula VId, wherein n is 1, 2 or 3.

In further embodiments, an inhibitor of 11-cis-retinol dehydrogenase has a structure represented by formula VId, wherein R³ is methyl.

In further embodiments, an inhibitor of 11-cis-retinol dehydrogenase has a structure represented by formula VId, wherein R¹ is hydrogen.

In further embodiments, an inhibitor of 11-cis-retinol dehydrogenase has a structure represented by formula VId, wherein n is 1, 2 or 3; R³ is methyl.

In further embodiments, an inhibitor of 11-cis-retinol dehydrogenase has a structure represented by formula VId, wherein n is 1, 2 or 3; R³ is methyl; and R¹ is hydrogen.

In further embodiments, an inhibitor of 11-cis-retinol dehydrogenase has a structure represented by formula VIe, wherein R¹ is hydrogen.

In further embodiments, an inhibitor of 11-cis-retinol dehydrogenase has a structure represented by formula VIe, wherein m is 1 to 10 inclusive.

In further embodiments, an inhibitor of 11-cis-retinol dehydrogenase has a structure represented by formula VIe, wherein m is 11 to 20 inclusive.

In further embodiments, an inhibitor of 11-cis-retinol dehydrogenase has a structure represented by formula VIe, wherein m is 11 to 20 inclusive; and R¹ is hydrogen.

11-cis-retinol dehydrogenase inhibitors having structures represented by formular VIe may be generated according to a diversity library approach as shown in Scheme 1, among other ways:

Scheme 1

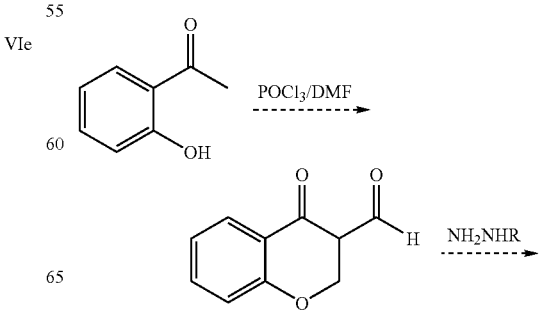

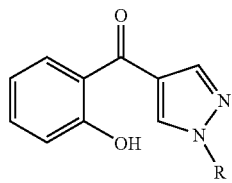

In one embodiment, an inhibitor of 11-cis-retinol dehydrogenas is 13-cis-retinoic acid (isoretinoin, ACCUTANE®):

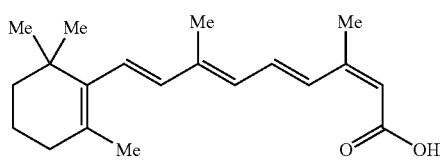

Also included are pharmaceutically acceptable addition salts and complexes of the compounds of the formulas given above. In cases wherein the compounds may have one or more chiral centers, unless specified, the compounds contemplated herein may be a single stereoisomer or racemic mixtures of stereoisomers. Further included are prodrugs, analogs, and derivatives thereof.

In some embodiments, two or more enzyme inhibitors and/or RPE65 binding inhibitors may be combined. In some embodiments, an enzyme inhibitor and/or RPE65 binding inhibitor may be combined with a short-circuiting compound. Combinations may be selected to inhibit sequential steps in the visual cycle (that is, two steps that occur one immediately after the other).

In certain embodiments, an inhibitor of isomerohydrolase (IMH) may be a compound having a structure represented by general structure 1:

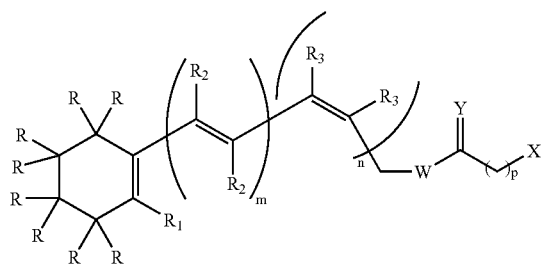

wherein, independently for each occurrence:
R, $R_1$, $R_2$, and $R_3$ are H, alkyl, alkenyl, alkynyl, aryl, aralkyl, heteroaryl, or heteroaralkyl;
W and Y are O, NR, R, or S;
X is H, alkyl, haloalkyl, aryl, or halide;
m and n are integers from 1 to 6 inclusive; and
p is an integer from 0 to 6 inclusive.

In a further embodiment, the inhibitor of IMH has the structure of formula 1 and the attendant definitions, wherein $R_2$ and $R_3$ is H or Me.

In a further embodiment, the inhibitor of IMH has the structure of formula 1 and the attendant definitions, wherein m is 2.

In a further embodiment, the inhibitor of IMH has the structure of formula 1 and the attendant definitions, wherein n is 2.

In a further embodiment, the inhibitor of IMH has the structure of formula 1 and the attendant definitions, wherein W is O.

In a further embodiment, the inhibitor of IMH has the structure of formula 1 and the attendant definitions, wherein W is C.

In a further embodiment, the inhibitor of IMH has the structure of formula 1 and the attendant definitions, wherein Y is O.

In a further embodiment, the inhibitor of IMH has the structure of formula 1 and the attendant definitions, wherein p is 1.

In a further embodiment, the inhibitor of IMH has the structure of formula 1 and the attendant definitions, wherein X is Br.

In a further embodiment, the inhibitor of IMH has the structure of formula 1 and the attendant definitions, wherein $R_2$ and $R_3$ is H or Me, and m is 2.

In a further embodiment, the inhibitor of IMH has the structure of formula 1 and the attendant definitions, wherein $R_2$ and $R_3$ is H or Me, m is 2, and n is 2.

In a further embodiment, the inhibitor of IMH has the structure of formula 1 and the attendant definitions, wherein $R_2$ and $R_3$ is H or Me, m is 2, n is 2, and W is O.

In a further embodiment, the inhibitor of IMF has the structure of formula 1 and the attendant definitions, wherein $R_2$ and $R_3$ is H or Me, m is 2, n is 2, W is O, and Y is O.

In a further embodiment, the inhibitor of IMH has the structure of formula 1 and the attendant definitions, wherein $R_2$ and $R_3$ is H or Me, m is 2, n is 2, W is O, Y is O, and p is 1.

In a further embodiment, the inhibitor of IMH has the structure of formula 1 and the attendant definitions, wherein $R_2$ and $R_3$ is H or Me, m is 2, n is 2, W is O, Y is O, p is 1, and X is Br.

In one embodiment, an isomerohydrolase inhibitor is 11-cis-retinyl bromoacetate (cRBA):

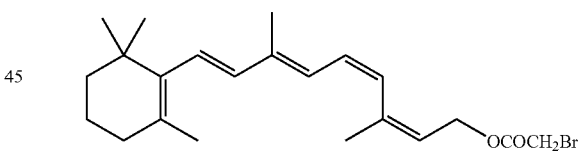

In certain embodiments, an inhibitor of IMH may be a compound of formula 8a:

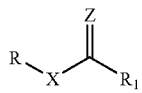

8a
wherein, independently for each occurrence:
X is O, S, NR', $CH_2$, or NHNR';
Z is O or NOH;
$R_1$ is —$CH_2F$, —$CHF_2$, —$CF_3$, —$CH_2N_2$, —$CH_2C(O)$OR, —OR', —C(O)CHR', —C(NH)CHR', or —CH=CHR';
R' is H, alkyl, heteroalkyl, aryl, heteroaryl, aralkyl, or heteroaralkyl;

R is

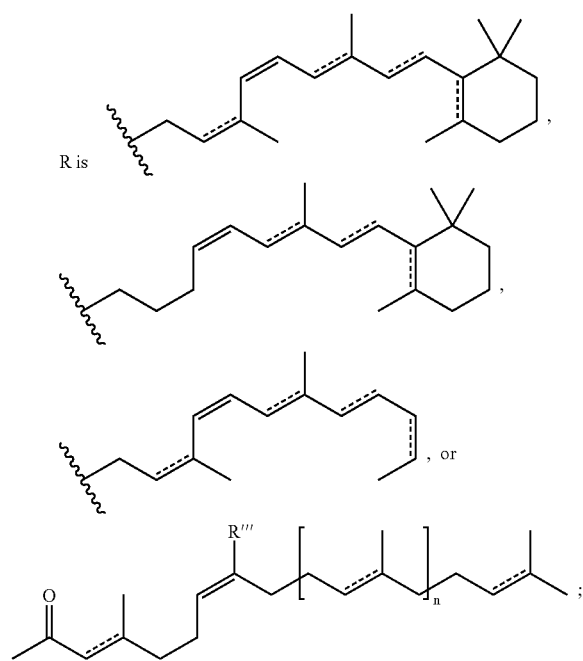

R''' is CH$_3$ or H; and
n is 0, 1 or 2;
wherein ----denotes a single bond, a cis double bond or a trans double bond.

Compounds of formula 8a may be considered irreversible inhibitors of IMH because they can covalently bind IMH, permanently disabling it.

In certain embodiments, an inhibitor of IMH may be a compound of formula 8a wherein Z is O.

In certain embodiments, an inhibitor of IMH may be a compound of formula 8b:

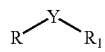

8b wherein, independently for each occurrence:
Y is C=O, C=S, C=NR', or CH$_2$;
R$_1$ is R', —OR', or —CN;
R' is H, alkyl, heteroalkyl, aryl, heteroaryl, aralkyl, or heteroaralkyl;

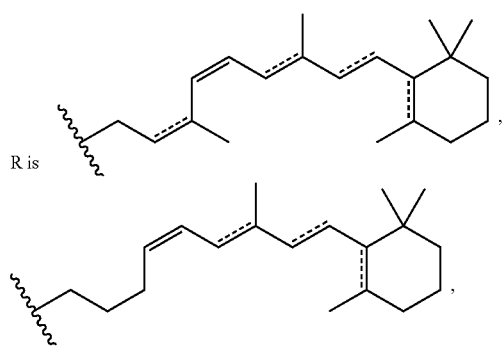

-continued

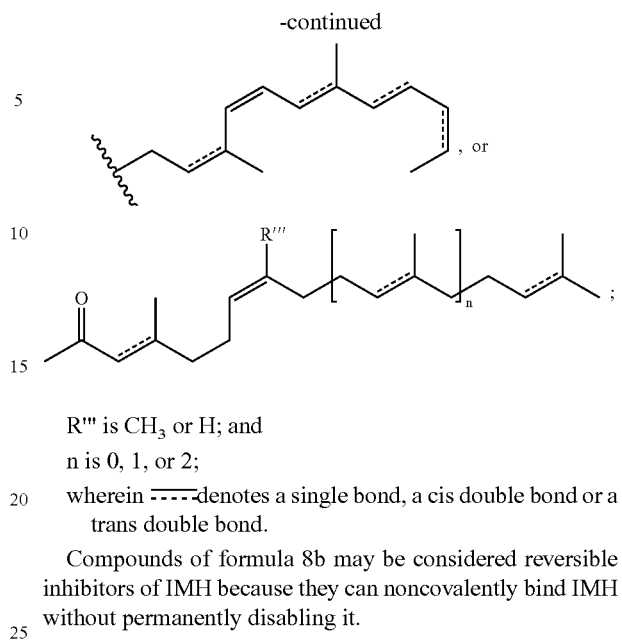

R''' is CH$_3$ or H; and
n is 0, 1, or 2;
wherein ----denotes a single bond, a cis double bond or a trans double bond.

Compounds of formula 8b may be considered reversible inhibitors of IMH because they can noncovalently bind IMH without permanently disabling it.

In certain embodiments, an inhibitor of IMH may be a compound of formula 8c:

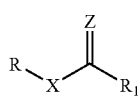

8c wherein, independently for each occurrence:
X is O, S, NR', CH$_2$, or NHNR';
Z is O or NOH;
R$_1$ is —CH$_2$F, —CHF$_2$, —CF$_3$, —CH$_2$N$_2$, —CH$_2$C(O)OR, —OR', —C(O)CHR', —C(NH)CHR', or —CH=CHR';
R' is H, alkyl, heteroalkyl, aryl, heteroaryl, aralkyl, or heteroaralkyl;

R is

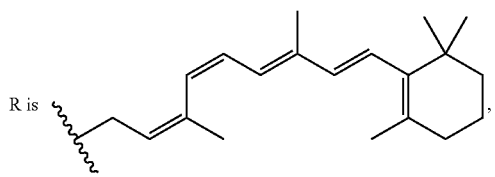

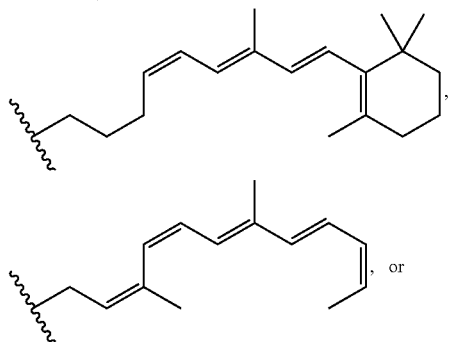

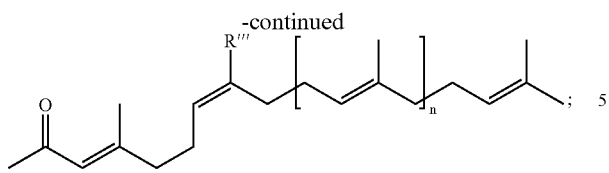

R''' is CH$_3$ or H; and
n is 0, 1 or 2.

Compounds of formula 8c may be considered irreversible inhibitors of IMH because they can covalently bind IMH, permanently disabling it.

In certain embodiments, an inhibitor of IMH may be a compound of formula 8c wherein Z is O.

In certain embodiments, an inhibitor of IMH may be a compound of formula 8d:

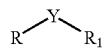

8d wherein, independently for each occurrence:
Y is C=O, C=S, C=NR', or CH$_2$;
R$_1$ is R', —OR', or —CN;
R' is H, alkyl, heteroalkyl, aryl, heteroaryl, aralkyl, or heteroaralkyl;

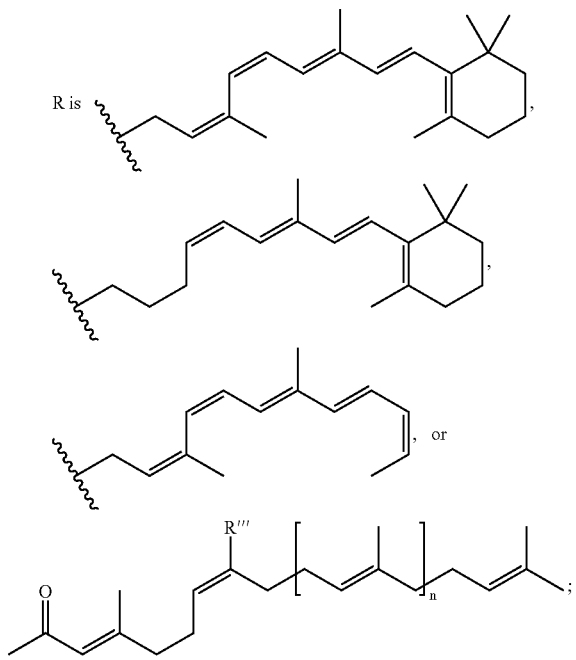

R''' is CH$_3$ or H; and
n is 0, 1 or 2.

Compounds of formula 8d may be considered reversible inhibitors of IMH because they can noncovalently bind IMH without permanently disabling it.

In certain embodiments, an inhibitor of LRAT may be a compound having a structure represented by general structure 2:

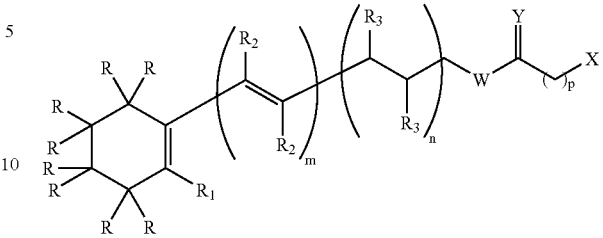

2 wherein, independently for each occurrence:
R, R$_1$, R$_2$, and R$_3$ are H, alkyl, alkenyl, alkynyl, aryl, aralkyl, heteroaryl, or heteroaralkyl;
W and Y are O, NR, R, or S;
X is H, alkyl, haloalkyl, or aryl;
m and n are integers from 1 to 6 inclusive; and
p is an integer from 0 to 6 inclusive.

In a further embodiment, the inhibitor of LRAT has the structure of formula 2 and the attendant definitions, wherein R$_2$ and R$_3$ is H or Me.

In a further embodiment, the inhibitor of LRAT has the structure of formula 2 and the attendant definitions, wherein m is 3.

In a further embodiment, the inhibitor of LRAT has the structure of formula 2 and the attendant definitions, wherein n is 1.

In a further embodiment, the inhibitor of LRAT has the structure of formula 2 and the attendant definitions, wherein W is O.

In a further embodiment, the inhibitor of LRAT has the structure of formula 2 and the attendant definitions, wherein W is C.

In a further embodiment, the inhibitor of LRAT has the structure of formula 2 and the attendant definitions, wherein Y is O.

In a further embodiment, the inhibitor of LRAT has the structure of formula 2 and the attendant definitions, wherein p is 0.

In a further embodiment, the inhibitor of LRAT has the structure of formula 2 and the attendant definitions, wherein X is OCF$_3$.

In a further embodiment, the inhibitor of LRAT has the structure of formula 2 and the attendant definitions, wherein R$_2$ and R$_3$ is H or Me, and m is 3.

In a further embodiment, the inhibitor of LRAT has the structure of formula 2 and the attendant definitions, wherein R$_2$ and R$_3$ is H or Me, m is 3, and n is 1.

In a further embodiment, the inhibitor of LRAT has the structure of formula 2 and the attendant definitions, wherein R$_2$ and R$_3$ is H or Me, m is 3, n is 1, and W is O.

In a further embodiment, the inhibitor of LRAT has the structure of formula 2 and the attendant definitions, wherein R$_2$ and R$_3$ is H or Me, m is 3, n is 1, W is O, and Y is O.

In a further embodiment, the inhibitor of LRAT has the structure of formula 2 and the attendant definitions, wherein R$_2$ and R$_3$ is H or Me, m is 3, n is 1, W is O, Y is O, and p is 0.

In a further embodiment, the inhibitor of LRAT has the structure of formula 2 and the attendant definitions, wherein R$_2$ and R$_3$ is H or Me, m is 3, n is 1, W is O, Y is O, p is 0, and X is OCF$_3$.

An exemplary inhibitor of LRAT is all-trans-retinyl α-bromoacetate. Another exemplary inhibitor of LRAT is 13-desmethyl-13,14-dihydro-all-trans-retinyl trifluoroacetate (RFA):

In certain embodiments, a compound that interferes with RPE65 binding may be a compound having a structure represented by general structure 3:

wherein, independently for each occurrence:

R and $R_1$ are H, alkyl, alkenyl, alkynyl, aryl, aralkyl, heteroaryl, or heteroaralkyl;

$R_2$ is H, alkyl, alkenyl, alkynyl, aryl, aralkyl, heteroaryl, heteroaralkyl, or —$CO_2R$;

$R_3$ is H, alkyl, alkenyl, alkynyl, aryl, aralkyl, heteroaryl, heteroaralkyl, or —$CH_2OR_4$;

$R_4$ is H, alkyl, alkenyl, alkynyl, aryl, aralkyl, heteroaryl, heteroaralkyl, heterocyclyl; and m is an integer from 1 to 6 inclusive.

In a further embodiment, the inhibitor of LRAT has the structure of formula 3 and the attendant definitions, wherein $R_2$ is H, Me, or —$CO_2H$.

In a further embodiment, the inhibitor of LRAT has the structure of formula 3 and the attendant definitions, wherein m is 4.

In a further embodiment, the inhibitor of LRAT has the structure of formula 3 and the attendant definitions, wherein $R_3$ is H.

In a further embodiment, the inhibitor of LRAT has the structure of formula 3 and the attendant definitions, wherein $R_2$ is H, Me, or —$CO_2H$ and m is 4.

In a further embodiment, the inhibitor of LRAT has the structure of formula 3 and the attendant definitions, wherein $R_2$ is H, Me, or —$CO_2H$, m is 4, and $R_3$ is H.

In certain embodiments, an inhibitor of LRAT may be a compound of formula 6a:

wherein, independently for each occurrence:
X is O, S, NR', $CH_2$, or NHNR';
Z is O or NOH;
$R_1$ is —$CH_2F$, —$CHF_2$, —$CF_3$, —$CH_2N_2$, —$CH_2C(O)OR$, —OR', —C(O)CHR', —C(NH)CHR', or —CH=CHR';
R' is H, alkyl, heteroalkyl, aryl, heteroaryl, aralkyl, or heteroaralkyl;

R is n is 1, 2, or 3;

wherein -----denotes a single bond, a cis double bond or a trans double bond.

Compounds of formula 6a may be considered irreversible inhibitors of LRAT because they can covalently bind LRAT, permanently disabling it.

In certain embodiments, an inhibitor of LRAT may be a compound of formula 6a wherein Z is O.

In certain embodiments, an inhibitor of LRAT may be a compound of formula 6b:

wherein, independently for each occurrence:
Y is C=O, C=S, C=NR', or $CH_2$;
$R_1$ is R', —OR', or —CN;
R' is H, alkyl, heteroalkyl, aryl, heteroaryl, aralkyl, or heteroaralkyl;

R is

-continued

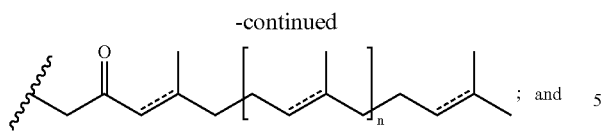
; and n is 1, 2, or 3;

wherein ----- denotes a single bond, a cis double bond or a trans double bond.

Compounds of formula 6c may be considered reversible inhibitors of LRAT because they can noncovalently bind LRAT without permanently disabling it.

In certain embodiments, an inhibitor of LRAT may be a compound of formula 6c:

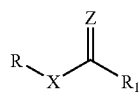
6c wherein independently for each occurrence:

X is O, S, NR', CH$_2$, or NHNR';

Z is O or NOH;

R$_1$ is —CH$_2$F, —CHF$_2$, —CF$_3$, —CH$_2$N$_2$, —CH$_2$C(O)OR, —OR', —C(O)CHR', —C(NH)CHR', or —CH=CHR';

R' is H, alkyl, heteroalkyl, aryl, heteroaryl, aralkyl, or heteroaralkyl;

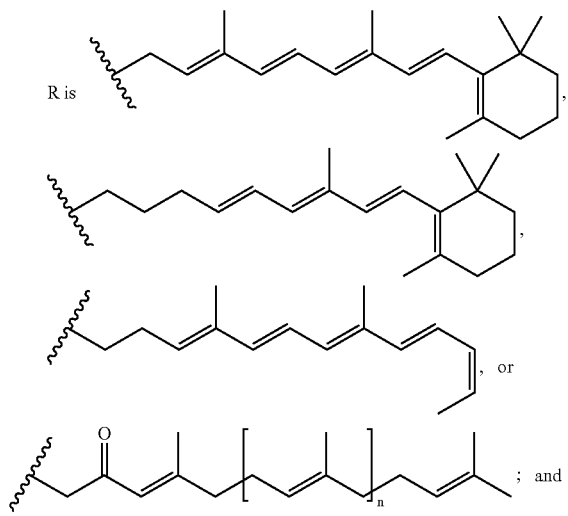

n is 1, 2, or 3.

Compounds of formula 6c may be considered irreversible inhibitors of LRAT because they can covalently bind LRAT, permanently disabling it.

In certain embodiments, an inhibitor of LRAT may be a compound of formula 6c wherein Z is O.

In certain embodiments, an inhibitor of LRAT may be a compound of formula 6d:

6d wherein, independently for each occurrence:

Y is C=O, C=S, C=NR', or CH$_2$;

R$_1$ is R', —OR', or —CN;

R' is H, alkyl, heteroalkyl, aryl, heteroaryl, aralkyl, or heteroaralkyl;

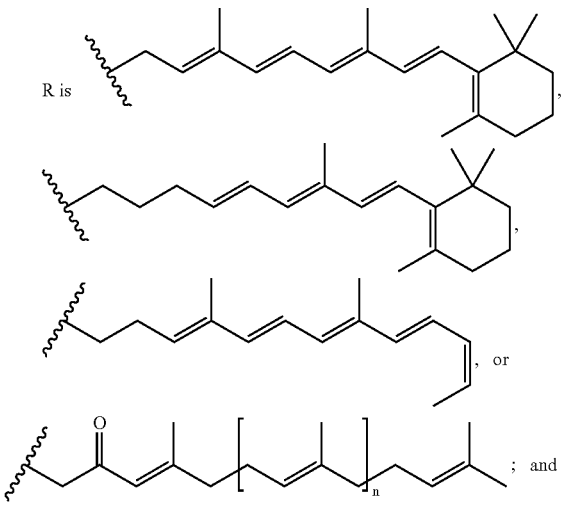

n is 1, 2, or 3.

Compounds of formula 6d may be considered reversible inhibitors of LRAT because they can noncovalently bind LRAT without permanently disabling it.

One exemplary embodiment of a compound that interferes with RPE65 binding is 13-cis-retinoic acid (isotretinoin, ACCUTANE®):

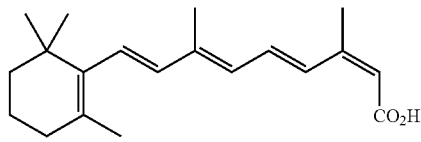

13-cis-retinoic acid is converted in vivo to all-trans-retinoic acid, which is a powerful inhibitor of RPE65 function.

In certain embodiments, an antagonist of RPE65 is a compound having a structure represented by general structure 4:

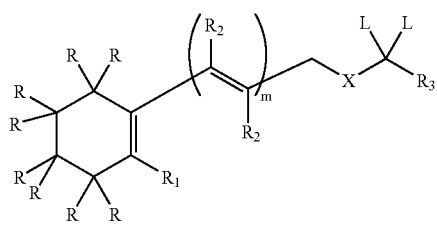
4 wherein, independently for each occurrence:

R, R$_1$, R$_2$ are H, alkyl, alkenyl, alkynyl, aryl, aralkyl, heteroaryl, heteroaralkyl, alkoxy, aryloxy, amino, halo, hydroxy, or carboxyl;

R$_3$ is alkyl, alkenyl, alkynyl, aryl, aralkyl, heteroaryl, heteroaralkyl, or ether;

L is H, OH, NH$_2$, N(R)$_2$, alkoxy, aryloxy, halo, hydroxy, carboxyl, or two L taken together represent O, S, or NR;

X is C(R)$_2$, O, S, or NR; and m is an integer from 1 to 6 inclusive.

In a further embodiment, an RPE65 antagonist has the structure of formula 4 and the attendant definitions, wherein X is O.

In a further embodiment, an RPE65 antagonist has the structure of formula 4 and the attendant definitions, wherein X is CH$_2$.

In a further embodiment, an RPE65 antagonist has the structure of formula 4 and the attendant definitions, wherein X is NH.

In a further embodiment, an RPE65 antagonist has the structure of formula 4 and the attendant definitions, wherein two Ls taken together represent O.

In a further embodiment, an RPE65 antagonist has the structure of formula 4 and the attendant definitions, wherein two Ls taken together represent NOH.

In a further embodiment, an RPE65 antagonist has the structure of formula 4 and the attendant definitions, wherein L is H, OH, or NH$_2$.

In a further embodiment, an RPE65 antagonist has the structure of formula 4 and the attendant definitions, wherein each L is H.

In a further embodiment, an RPE65 antagonist has the structure of formula 4 and the attendant definitions, wherein m is 4.

In a further embodiment, an RPE65 antagonist has the structure of formula 4 and the attendant definitions, wherein m is 3.

In a further embodiment, an RPE65 antagonist has the structure of formula 4 and the attendant definitions, wherein R$_2$ is H or methyl.

In a further embodiment, an RPE65 antagonist has the structure of formula 4 and the attendant definitions, wherein R$_3$ is alkyl.

In a further embodiment, an RPE65 antagonist has the structure of formula 4 and the attendant definitions, wherein R$_3$ is ether.

In a further embodiment, an RPE65 antagonist has the structure of formula 4 and the attendant definitions, wherein X is O and two L taken together represents O.

In a further embodiment, an RPE65 antagonist has the structure of formula 4 and the attendant definitions, wherein X is O and each L is H.

In a further embodiment, an RPE65 antagonist has the structure of formula 4 and the attendant definitions, wherein X is NH and two L taken together represents O.

In a further embodiment, an RPE65 antagonist has the structure of formula 4 and the attendant definitions, wherein X is CH$_2$ and two L taken together represents O.

In a further embodiment, an RPE65 antagonist has the structure of formula 4 and the attendant definitions, wherein X is CH$_2$ and two L taken together represents NOH.

In a further embodiment, an RPE65 antagonist has the structure of formula 4 and the attendant definitions, wherein X is O, two L taken together represent O, R$_2$ is H or methyl, m is 4, and R$_3$ is a C15 alkyl.

In a further embodiment, an RPE65 antagonist has the structure of formula 4 and the attendant definitions, wherein X is O, two L taken together represent O, R$_2$ is H or methyl, m is 4, and R$_3$ is a C5 alkyl.

In a further embodiment, an RPE65 antagonist has the structure of formula 4 and the attendant definitions, wherein X is O, two L taken together represent O, R$_2$ is H or methyl, m is 4, and R$_3$ is methyl.

In a further embodiment, an RPE65 antagonist has the structure of formula 4 and the attendant definitions, wherein X is O, each L is H, R$_2$ is H or methyl, m is 4, and R$_3$ is a C15 alkyl.

In a further embodiment, an RPE65 antagonist has the structure of formula 4 and the attendant definitions, wherein X is NH, two L taken together represents O, R$_2$ is H or methyl, m is 4, and R$_3$ is a C15 alkyl.

In a further embodiment, an RPE65 antagonist has the structure of formula 4 and the attendant definitions, wherein X is CH$_2$, two L taken together represents O, R$_2$ is H or methyl, m is 4, and R$_3$ is a C15 alkyl.

In a further embodiment, an RPE65 antagonist has the structure of formula 4 and the attendant definitions, wherein X is O, each L is H, R$_2$ is H or methyl, m is 4, and R$_3$ is an ether.

In a further embodiment, an RPE65 antagonist has the structure of formula 4 and the attendant definitions, wherein X is O, each L is H, R$_2$ is H or methyl, m is 4, and R$_3$ is —CH$_2$OCH$_2$CH$_2$OCH$_2$CH$_2$OC$_7$H$_{15}$.

In a further embodiment, an RPE65 antagonist has the structure of formula 4 and the attendant definitions, wherein X is CH$_2$, two L taken together represent NOH, R$_2$ is H or methyl, m is 4, and R$_3$ is a C15 alkyl.

In a further embodiment, an RPE65 antagonist has the structure of formula 4 and the attendant definitions, wherein X is CH$_2$, L is H, OH, or NH$_2$, R$_2$ is H or methyl, m is 4, and R$_3$ is a C15 alkyl.

In certain embodiments, an inhibitor of RPE65 may be a compound of formula 7a:

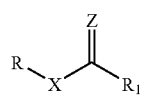

7a wherein, independently for each occurrence:

X is O, S, NR', CH$_2$, or NHNR';

Z is O or NOH;

R$_1$ is —CH$_2$F, —CHF$_2$, —CF$_3$, —CH$_2$N$_2$, —CH$_2$C(O)OR, —OR', —C(O)CHR', —C(NH)CHR', or —CH═CHR';

R' is H, alkyl, heteroalkyl, aryl, heteroaryl, aralkyl, or heteroaralkyl;

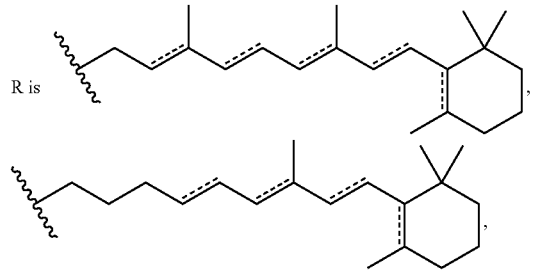

R is

-continued

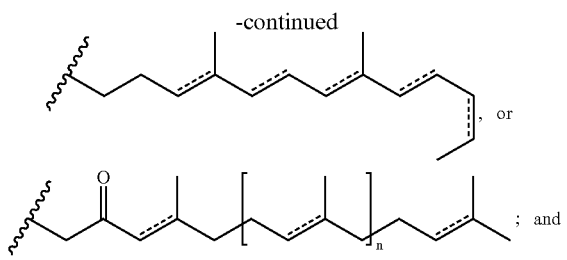

n is 1, 2, or 3;
wherein ----- denotes a single bond, a cis double bond or a trans double bond.

Compounds of formula 7a may be considered irreversible antagonists of RPE65 because they can covalently bind RPE65, permanently disabling it.

In certain embodiments, an inhibitor of RPE65 may be a compound of formula 7a wherein Z is O.

In certain embodiments, an inhibitor of RPE65 may be a compound of formula 7b:

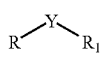
7b wherein, independently for each occurrence:
Y is O, S, NR', $CH_2$=O, C=S, C=NR', CHOR', CHNR'R", CHSR', or $CH_2$;
$R_1$ is R', —OR', —CN or $(CH_2CH_2O)_m R'$;
R' is H, alkyl, heteroalkyl, aryl, heteroaryl, aralkyl, or heteroaralkyl;
R" is H, alkyl, heteroalkyl, aryl, heteroaryl, aralkyl, or heteroaralkyl;

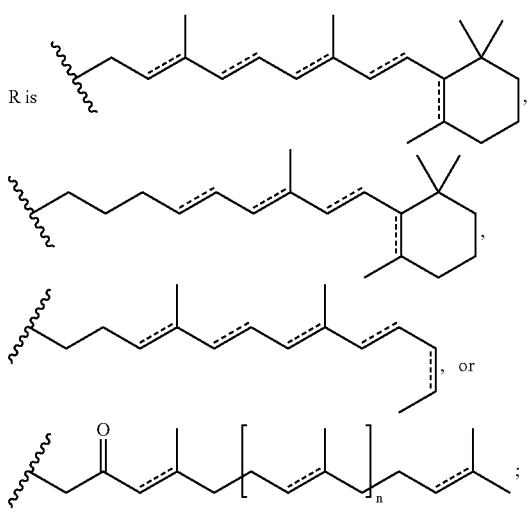

m is 1, 2 or 3; and
n is 1, 2, or 3;
wherein ----- denotes a single bond, a cis double bond or a trans double bond.

Compounds of formula 7b may be considered reversible antagonists of RPE65 because they can noncovalently bind RPE65 without permanently disabling it.

In certain embodiments, an inhibitor of RPE65 may be a compound of formula 7c:

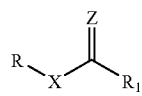
7c wherein, independently for each occurrence:
X is O, S, NR', $CH_2$, or NHNR';
Z is O or NOH;
$R_1$ is —$CH_2F$, —$CHF_2$, —$CF_3$, —$CH_2N_2$, —$CH_2C(O)$OR, —OR', —C(O)CHR', —C(NH)CHR', or —CH=CHR';
R' is H, alkyl, heteroalkyl, aryl, heteroaryl, aralkyl, or heteroaralkyl;

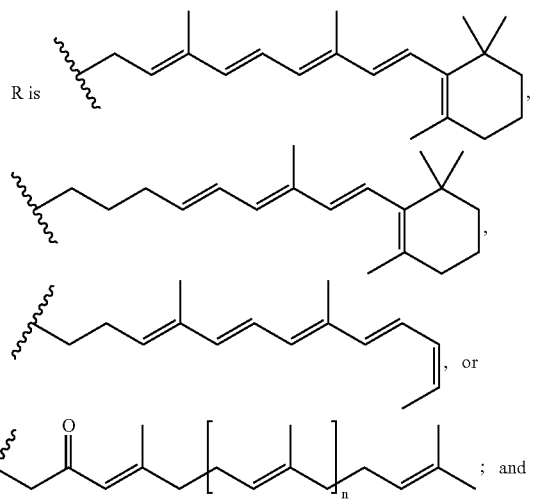

n is 1, 2, or 3.

Compounds of formula 7c may be considered irreversible antagonists of RPE65 because they can covalently bind RPE65, permanently disabling it.

In certain embodiments, an inhibitor of RPE65 may be a compound of formula 7c wherein Z is O.

In certain embodiments, an inhibitor of RPE65 may be a compound of formula 7d:

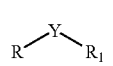
7d wherein, independently for each occurrence:
Y is C=O, C=S, C=NR', CHOH, CHOR', $NH_2$, NHR', NR'R", SH, SR', or $CH_2$;
$R_1$ is R', —OR', —CN or —$(CH_2CH_2O)_m R'$;
R' is H, alkyl, heteroalkyl, aryl, heteroaryl, aralkyl, or heteroaralkyl;
R" is H, alkyl, heteroalkyl, aryl, heteroaryl, aralkyl, or heteroaralkyl;

R is

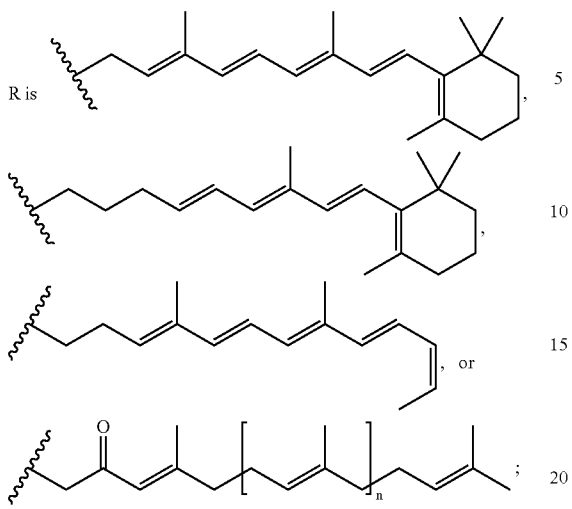

m is 1, 2 or 3; and
n is 1, 2, or 3.

B. Compositions for Short-Circuiting

Short-circuiting the visual cycle can be achieved by catalyzing the thermodynamically downhill isomerization of 11-cis-retinal to all-trans-retinal in the RPE, before the 11-cis-retinal leaves the RPE. FIG. 3 depicts one contemplated intervention. A very wide variety of substances are envisioned as appropriate for this use. Broadly speaking, appropriate drugs include aniline derivates, i.e., a benzene ring with an amine side chain.

Short circuiting molecules operate by first forming a Schiff base with a retinal. When a Schiff base is formed with 11-cis-retinal, isomerization occurs. This is the short circuit.

Short-circuit compounds may also trap retinals so that they are not available to form $A_2E$, its precursors or analogs. With all-trans-retinal, a relatively stable Schiff base can be formed with the drugs which traps the all-trans-retinal and prevents it from forming $A_2E$ and like compounds. The short-circuit drug competes with phosphatidylethanolamine for binding all-trans-retinal. The trapped compounds may then be broken down in lysozomes to non-toxic metabolites. A short-circuit drug may disrupt the visual cycle in one or both ways, i.e., by short-circuiting 11-cis-retinals and/or by trapping all-trans-retinals. ($A_2E$ is the best characterized of the lipofuscins. There may be other adducts between all-trans-retinal and amines—or even proteins—whose formation is initiated by Schiff base formation between a reactive retinal and an amine.)

While it is not expected that an aromatic amine/all-trans-retinal Schiff base will go on to form $A_2E$-like molecules (because it will be degraded first), this can be more reliably prevented by using a short-circuiting drug that is a secondary amine. This is because the mechanism of $A_2E$ formation requires a primary amine (two free Hs) because two new N-alkyl bonds are made (one with each all-trans-retinal molecule) and this cannot happen starting with a secondary or tertiary amine. If the short-circuit drug is a secondary amine, then it can bind only one molecule of all-trans-retinal and has no remaining site to bind a second all-trans-retinal, thereby preventing the formation of compounds analogous to $A_2E$ akin to the process shown in FIG. 2.

Short-circuit drugs may also provide a long-term effect, so that their administration can be infrequent. In some cases, administration may be required monthly. In other cases, administration may be required weekly. The short-circuit drugs effectively deplete vitamin A stores locally in the eye by trapping all-trans-retinal. Once the store of vitamin is diminished by the drug, the visual cycle is impaired, and lipofuscin formation is retarded, which is the goal of therapy. Vitamin A stores are replenished only very slowly in the eye, so that a single administration of short-circuit drug may have a prolonged effect. In addition, the short-circuit drugs may be cleared slowly from the eye, so that they may be available for binding over extended periods.

In certain embodiments, a short-circuiting compound has the structure represented by formula VII:

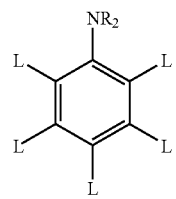

VII wherein, independently for each occurrence:

R is H, alkyl, alkenyl, alkynyl, aryl, aralkyl, heteroaryl, heteroaralkyl, or carbonyl;

L is a hydrophobic moiety, or any two adjacent L taken together form a fused aromatic or heteroaromatic ring (e.g. a naphthalene, an anthracene, an indole, a quinoline, etc.).

In certain embodiments, independently for each occurrence, L is alkyl, alkenyl, alkynyl, aryl, aralkyl, heteroaryl, heteroaralkyl, carbonyl, ether, or polycyclic. In certain embodiments, L has the formula VIIa:

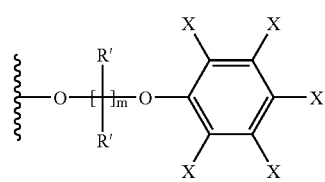

VIIa wherein, independently for each occurrence:

R' and X are hydrogen, alkyl, alkenyl, alkynyl, aryl, aralkyl, heteroaryl, heteroaralkyl, carbonyl, alkoxy, hydroxy, thiol, thioalkyl, or amino; and m is an integer from 1 to 6 inclusive.

In some embodiments, a short circuit drug may be represented by the following generic formula VIIb:

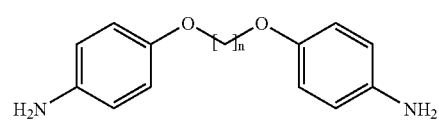

VIIb wherein n is an integer from 1 to 8 inclusive.

In some embodiments, a short circuit drug may be represented by the following generic formula VIIc:

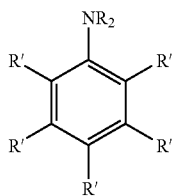

wherein, independently for each occurrence,
R is H, alkyl, or acyl; and
R' is alkyl or ether.

In a further embodiment, a short circuit drug has the structure of formula VIIc and the attendant definitions, wherein R is H for both occurrences.

In a further embodiment, a short circuit drug has the structure of formula VIIc and the attendant definitions, wherein at least one R is alkyl.

In a further embodiment, a short circuit drug has the structure of formula VIIc and the attendant definitions, wherein at least one R is methyl.

In some embodiments, a short circuit drug may be represented by the following generic formula VIId:

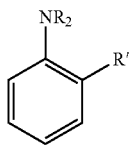

wherein, independently for each occurrence:
R is H, alkyl, or acyl; and
R' is alkyl or ether.

In a further embodiment, a short circuit drug has the structure of formula VIId and the attendant definitions, wherein R is H for both occurrences.

In a further embodiment, a short circuit drug has the structure of formula VIId and the attendant definitions, wherein at least one R is alkyl.

In a further embodiment, a short circuit drug has the structure of formula VIId and the attendant definitions, wherein at least one R is methyl.

In some embodiments, a short circuit drug may be represented by the following generic formula VIIe:

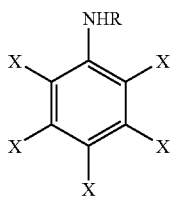

wherein, independently for each occurrence:
X is hydrogen or —C(=O)OR';
R is H, alkyl, or acyl; and
R' is alkyl.

In a further embodiment, a short circuit drug has the structure of formula VIIe and the attendant definitions, wherein R is H.

In a further embodiment, a short circuit drug has the structure of formula VIIe and the attendant definitions, wherein at least one R is alkyl.

In a further embodiment, a short circuit drug has the structure of formula VIIe and the attendant definitions, wherein R is methyl.

In some embodiments, a short circuit drug may be represented by the following generic formula VIIf:

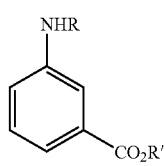

wherein, independently for each occurrence
R is H, alkyl, or acyl; and
R' is alkyl.

In a further embodiment, a short circuit drug has the structure of formula VIIf and the attendant definitions, wherein R is H.

In a further embodiment, a short circuit drug has the structure of formula VIIf and the attendant definitions, wherein at least one R is alkyl.

In a further embodiment, a short circuit drug has the structure of formula VIIf and the attendant definitions, wherein R is methyl.

In one embodiment, a short circuiting drug is diaminophenoxypentane:

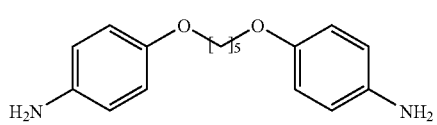

In one embodiment, a short circuiting drug is phenetidine:

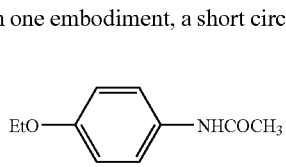

In one embodiment, a short circuiting drug is and tricaine:

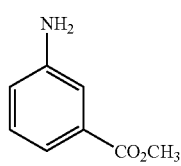

In one embodiment, a short circuiting drug is 4-butylanaline:

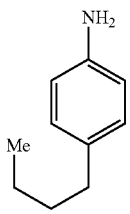

In one embodiment, a short circuiting drug is N-methyl-4-butylanaline:

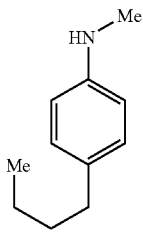

In one embodiment, a short circuiting drug is ethyl 3-aminobenzoate:

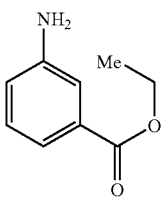

In one embodiment, a short circuiting drug is ethyl N-methyl-3-aminobenzoate:

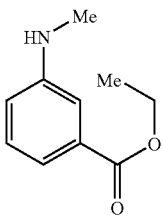

In one embodiment, a short circuiting drug is ethyl 2-aminobenzoate:

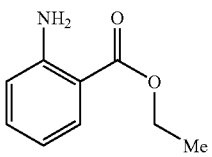

In one embodiment, a short circuiting drug is ethyl N-methyl-2-aminobenzoate:

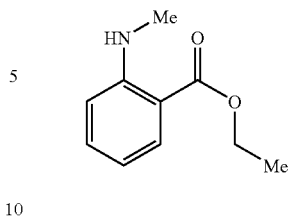

In some embodiments, a short circuit drug may be represented by the following generic formula VIII:

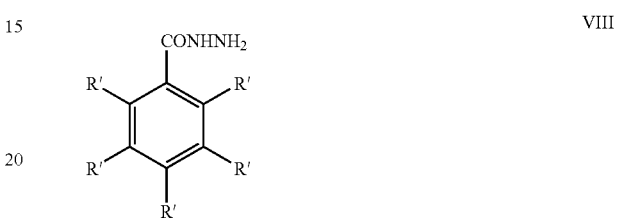

VIII wherein R' is hydrogen, alkyl or ether; or any two adjacent L taken together form a fused aromatic or heteroaromatic ring (e.g. a naphthalene, an anthracene, etc.).

In certain embodiments, a short-circuiting compound has the structure represented by formula IX:

ANR$_2$  IX wherein, independently for each occurrence:

R is H, alkyl, alkenyl, alkynyl, aryl, aralkyl, heteroaryl, heteroaralkyl, or carbonyl; and A is optionally substituted aryl or heteroaryl.

In some embodiments, a short circuit drug may be represented by the following generic formula X:

AC(=O)NHNH$_2$  X wherein independently for each occurrence:

R' is hydrogen, alkyl or ether; and

A is optionally substituted aryl or heteroaryl.

In certain embodiments, a short-circuiting compound may have a structure represented by general structure 5:

5 wherein, independently for each occurrence:

R is H, alkyl, alkenyl, alkynyl, aryl, aralkyl, heteroaryl, heteroaralkyl, or carbonyl;

L is a hydrophobic moiety, or any two adjacent L taken together form a fused aromatic ring; and n is an integer from 0 to 5 inclusive.

In certain embodiments, independently for each occurrence, L is alkyl, alkenyl, alkynyl, aryl, aralkyl, heteroaryl, heteroaralkyl, carbonyl, ether, or polycyclic. In certain embodiments, L has the formula 5a:

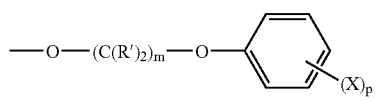

wherein, independently for each occurrence:
R' and X are H, alkyl, alkenyl, alkynyl, aryl, aralkyl, heteroaryl, heteroaralkyl, carbonyl, alkoxy, hydroxy, thiol, thioalkyl, or amino;
m is an integer from 1 to 6 inclusive; and
p is an integer from 0 to 5 inclusive.

Selected specific examples of short circuit drugs include diaminophenoxypentane:

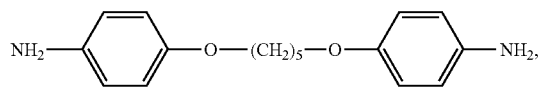

phenetidine:

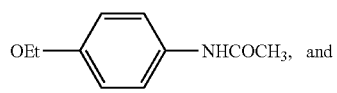

tricaine:

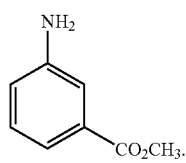

In some embodiments, a short circuit drug may be represented by the following generic formula 5b:

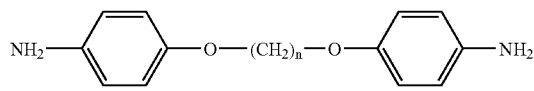

wherein n is an integer from 1 to 8 inclusive.

In some embodiments, a short circuit drug may be represented by the following generic formula 5c:

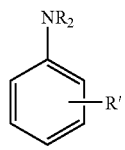

wherein, independently for each occurrence:
R is H, alkyl, or acyl; and
R' is alkyl or ether.

In a further embodiment, a short circuit drug has the structure of formula 5c and the attendant definitions, wherein R is H for both occurrences.

In a further embodiment, a short circuit drug has the structure of formula 5c and the attendant definitions, wherein at least one R is alkyl.

In a further embodiment, a short circuit drug has the structure of formula 5c and the attendant definitions, wherein at least one R is methyl.

In some embodiments, a short circuit drug may be represented by the following generic formula 5c1:

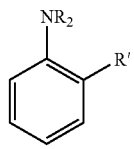

wherein, independently for each occurrence:
R is H, alkyl, or acyl; and
R' is alkyl or ether.

In a further embodiment, a short circuit drug has the structure of formula 5c1 and the attendant definitions, wherein R is H for both occurrences.

In a further embodiment, a short circuit drug has the structure of formula 5c1 and the attendant definitions, wherein at least one R is alkyl.

In a further embodiment, a short circuit drug has the structure of formula 5c1 and the attendant definitions, wherein at least one R is methyl.

In some embodiments, a short circuit drug may be represented by the following generic formula 5d:

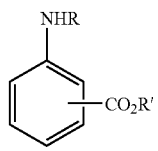

wherein, independently for each occurrence:
R is H, alkyl, or acyl; and
R' is alkyl.

In a further embodiment, a short circuit drug has the structure of formula 5d1 and the attendant definitions, wherein R is H.

In a further embodiment, a short circuit drug has the structure of formula 5d and the attendant definitions, wherein at least one R is alkyl.

In a further embodiment, a short circuit drug has the structure of formula 5d and the attendant definitions, wherein R is methyl.

In some embodiments, a short circuit drug may be represented by the following generic formula 5d1:

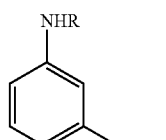

wherein, independently for each occurrence:
R is H, alkyl, or acyl; and
R' is alkyl.

In a further embodiment, a short circuit drug has the structure of formula 5d1 and the attendant definitions, wherein R is H.

In a further embodiment, a short circuit drug has the structure of formula 5d1 and is the attendant definitions, wherein at least one R is alkyl.

In a further embodiment, a short circuit drug has the structure of formula 5d1 and the attendant definitions, wherein R is methyl.

In some embodiments, a short circuit drug may be represented by the following generic formula 5e:

5e wherein R' is alkyl or ether.

Diseases associated with lipofuscin accumulation may also be treated or prevented with agents or drugs that prevent vitamin A import into the eye. Exemplary agents are those that prevent vitamin A delivery by retinol binding protein (RBP). Agents may thus be RBP inhibitors or blocking agents. RBP may be a CRBP protein (Ong et al. (1994)Nutr. Rev. 52:524 and Cowan et al. (1993) J. Mol. Biol. 230:1225) or a serum RBP (Blomhoff et al. (1990) Science 250:399 and Newcomer et al. (1984) EMBO J. 3, 1451). A preferred RBP to inhibit is CRBP-1. In an illustrative embodiment, the RBP blocking agent is fenretinide, a non-retinoid fenretinide analog or a non-retinoid fenretinide isoprenoid. Exemplary compounds have the structure depicted in formula XI:

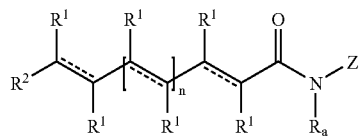

XI wherein, independently for each occurrence, n is 0 to 10 inclusive;

$R^1$ is hydrogen or alkyl;

$R^2$ is hydrogen, alkyl, cycloalkyl, alkenyl, cycloalkenyl, alkynyl, aryl, or aralkyl;

Z is hydrogen, alkyl, cycloalkyl, alkenyl, cycloalkenyl, alkynyl, aryl, aralkyl, —C(=O)$R_b$, or —(CH$_2$)$_p$$R_b$;

p is 0 to 20 inclusive;

$R_a$ is hydrogen, alkyl, cycloalkyl, alkenyl, cycloalkenyl, alkynyl, aryl, or aralkyl;

$R_b$ is hydrogen, alkyl, cycloalkyl, alkenyl, cycloalkenyl, alkynyl, aryl, or aralkyl; and ----denotes a single bond or a trans double bond.

In a further embodiment a RBP blocking agent has the structure of XI, wherein $R^1$ is hydrogen or methyl.

In a further embodiment a RBP blocking agent has the structure of XI, wherein Z is aryl.

In a further embodiment a RBP blocking agent has the structure of XI, wherein $R_a$ is hydrogen.

In a further embodiment a RBP blocking agent has the structure of XI, wherein $R^1$ is hydrogen or methyl; Z is aryl; and $R_a$ is hydrogen.

In a another embodiment a RBP blocking agent of the invention has the structure of formula XIa:

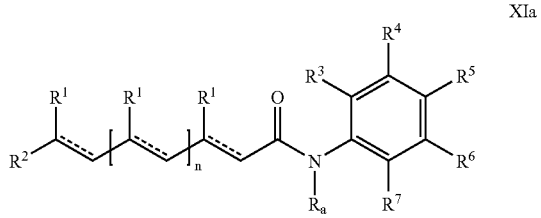

XIa wherein, independently for each occurrence, n is 0 to 10 inclusive;

$R^1$ is hydrogen or alkyl;

$R^2$ is hydrogen, alkyl, cycloalkyl, alkenyl, cycloalkenyl, alkynyl, aryl, or aralkyl;

$R^3$, $R^4$, $R^5$, $R^6$ and $R^7$ are hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, or sulfoxido;

$R_a$ is hydrogen, alkyl, cycloalkyl, alkenyl, cycloalkenyl, alkynyl, aryl, or aralkyl; and ----denotes a single bond or a trans double bond.

In a further embodiment a RBP blocking agent has the structure of XIa, wherein $R^1$ is hydrogen or methyl.

In a further embodiment a RBP blocking agent has the structure of XIa, wherein $R_a$ is hydrogen.

In a further embodiment a RBP blocking agent has the structure of XIa, wherein $R^1$ is hydrogen or methyl; and $R_a$ is hydrogen.

In a further embodiment a RBP blocking agent has the structure of XIa, wherein $R^3$, $R^4$, $R^6$ and $R^7$ are hydrogen.

In a further embodiment a RBP blocking agent has the structure of XIa, wherein $R^5$ is hydroxyl.

In a further embodiment a RBP blocking agent has the structure of XIa, wherein $R^3$, $R^4$, $R^6$ and $R^7$ are hydrogen; and $R^5$ is hydroxyl.

In a further embodiment a RBP blocking agent has the structure of XIa, wherein $R^1$ is hydrogen or methyl; $R_a$ is hydrogen; $R^3$, $R^4$, $R^6$ and $R^7$ are hydrogen; and $R^5$ is hydroxyl.

In a another embodiment a RBP blocking agent of the invention has the structure of formula XIb:

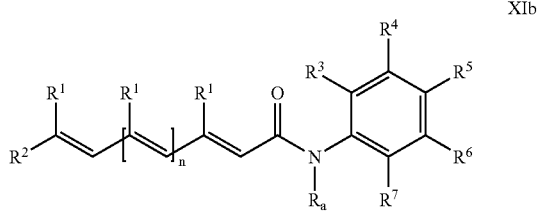

XIb wherein, independently for each occurrence, n is 0 to 5 inclusive;

$R^1$ is hydrogen or methyl;

$R^2$ is hydrogen, alkyl, alkenyl, alkynyl, aryl,

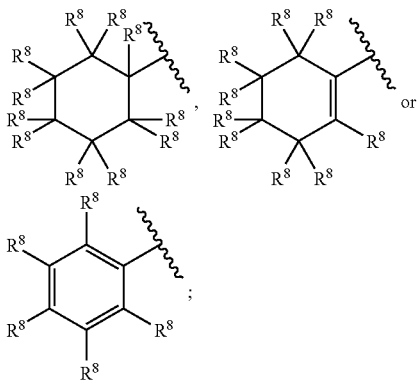

$R^3$, $R^4$, $R^5$, $R^6$, $R^7$ and $R^8$ are hydrogen, halogen, alkyl, alkenyl, alkynyl, aryl, heteroaryl, aralkyl, aralkyenyl, aralkynyl, heteroaralkyl, heteroaralkyenyl, heteroaralkynyl, cyano, nitro, sulfhydryl, hydroxyl, sulfonyl, amino, acylamino, amido, alkylthio, carboxyl, carbamoyl, alkoxyl, sulfonate, sulfate, sulfonamido, sulfamoyl, sulfonyl, or sulfoxido;

any two geminal $R^8$ and the carbon to which they are bound may represent C(=O); and $R_a$ is hydrogen, alkyl, cycloalkyl, alkenyl, cycloalkenyl, alkynyl, aryl, or aralkyl.

In a further embodiment a RBP blocking agent has the structure of XIb, wherein $R^1$ is hydrogen or methyl.

In a further embodiment a RBP blocking agent has the structure of XIb, wherein $R_a$ is hydrogen.

In a further embodiment a RBP blocking agent has the structure of XIb, wherein $R^1$ is hydrogen or methyl; and $R_a$ is hydrogen.

In a further embodiment a RBP blocking agent has the structure of XIb, wherein $R^3$, $R^4$, $R^6$ and $R^7$ are hydrogen.

In a further embodiment a RBP blocking agent has the structure of XIb, wherein $R^5$ is hydroxyl.

In a further embodiment a RBP blocking agent has the structure of XIb, wherein $R^3$, $R^4$, $R^6$ and $R^7$ are hydrogen; and $R^5$ is hydroxyl.

In a further embodiment a RBP blocking agent has the structure of XIb, wherein $R^1$ is hydrogen or methyl; $R_a$ is hydrogen; $R^3$, $R^4$, $R^6$ and $R^7$ are hydrogen; and $R^5$ is hydroxyl.

In a further embodiment a RBP blocking agent has the structure of XIb, wherein n is 1 to 3 inclusive.

In a further embodiment a RBP blocking agent has the structure of XIb, wherein

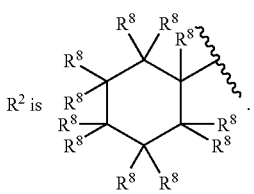

In a further embodiment a RBP blocking agent has the structure of XIb, wherein

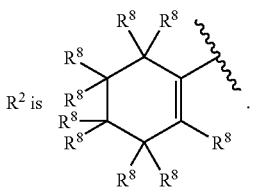

In a further embodiment a RBP blocking agent has the structure of XIb, wherein

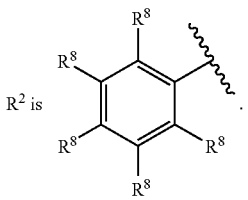

An RBP inhibitory compound may be a non-retinoid fenretinide analog, such as those set forth above, wherein the analog is not fenretinide.

Vitamin A delivery to the eye may also be inhibited by interfering with the membrane receptor for holo-RBP, which have been reported to be present in the RBP (Vogel et al. (1999) cited in Quadro et al. (1999) EMBO J. 18:4633). Alternatively, the interaction between RBP and its receptor may be inhibited.

In yet other embodiments, inhibitors of retinyl-ester isomerase (e.g., 11-cis-retinyl bromoacetate) and/or inhibitors of cellular retinaldehyde binding protein (CRALBP) (e.g., cis-isoprenoids) and/or inhibitors of 11-cis-retinol dehydrogenase (e.g., pyrazoles) may be used.

Also included are pharmaceutically acceptable addition salts and complexes of the compounds of the formulas given above. In cases wherein the compounds may have one or more chiral centers, unless specified, the compounds contemplated herein may be a single stereoisomer or racemic mixtures of stereoisomers. Further included are prodrugs, analogs, and derivatives thereof.

In some embodiments, a combination of one or more compounds described herein is administered to a subject. Two or more short-circuiting compounds may be combined. In some embodiments, an enzyme inhibitor and/or RPE65 binding inhibitor may be combined with a short-circuiting compound. An enzyme inhibitor and/or short-circuiting compound may also be combined with one or more agents that prevent the delivery of vitamin A to the eye, such as fenretinide, a non-retinoid fenretinide analog and a non-retinoid isoprenoid. For example, a compound of formula XI may be administered to a subject who is also receiving a compound of formula I, II, III, IV, V, VI, VII, VIII, IX, or X. Any other combination of compounds affecting different target proteins may also be used.

In combination therapies, the compounds may be administered simultaneously, e.g., in the form of one composition, or consecutively. When consecutively administered, the time between the two administrations may be one or more minutes, one or more hours, one or more days, or one or more weeks.

Therapeutic or prophylactic treatments with one or more of the compounds described herein may be combined with other treatments known in the art. For example, they may be used in conjunction with surgery and/or supplements, and/or radiation, and/or other therapeutic methods. Treatment of the wet form of AMD may be combined a treatment that removes or destroys the new blood vessels that grow in or around the macula. A laser, such as a thermal laser may be used for that purpose. Transpupillary thermotherapy is an alternative treatment, in which an infrared laser is used. Another method is photodynamic therapy, in which a substance that sensitizes the blood vessels in the eye to laser light is given intravenously, and then a beam of laser light is used to destroy the abnormal blood vessels. Photocoagulation therapy may also be used.

Treatments may also be combined with administration of an anti-oxidant, e.g., high doses of antioxidants, such as (vitamin C, vitamin E, and beta-carotene), zinc and copper ("supplementation therapy"). The antioxidant formulation may contain a combination of vitamin C, vitamin E, and beta-carotene. The specific daily amounts of antioxidants and zinc may be about 500 milligrams of vitamin C; 400 international units of vitamin E; 15 milligrams of beta-carotene; 80 milligrams of zinc as zinc oxide; and two milligrams of copper as cupric oxide (used in the Age-Related Eye Disease (ARED) study). A number of new drugs have promise for the prevention or delay of photoreceptor cell death and retinal degeneration. These drugs include PKC 412 (which blocks chemicals in the body that foster new blood vessel growth, or angiogenesis), Glial Derived Neurotrophic Factor (a survival factor which has slowed degeneration in a rodent model), and diatazem (a calcium-channel blocker which addresses a rare retinal gene defect called beta PDE).

Where a treatment of macular degeneration described herein is combined with radiotherapy, preferred forms of radiation for use in the treatment include: proton beam, strontium-90, palladium-103, radiosurgery, and EBRT (external beam radiation therapy). Radiation therapy for "wet" macular degeneration is used to destroy blood vessels and prevent neovascularization. Radiation therapy is useful after surgery to prevent or reduce scarring by killing or effecting the cells which make up newly formed blood vessels, inflammatory cells which promote scarring and cells which help create fibrous tissues.

The two therapies may be provided simultaneously or consecutively. For example, a surgical method may be applied first, followed by administration of one or more compounds described herein. Alternatively, a surgical method may be used after administration of one or more compounds described herein. The second therapeutic method, such as surgery, may also be preceded by and followed by administration of one or more compounds described herein.

The other therapy may precede or follow the therapeutic agent-based therapy by intervals ranging from minutes to days to weeks. In embodiments where the other macular or retinal degeneration therapy and the therapeutic agent-based therapy are administered together, one may prefer to avoid that a significant period of time did not expire between the time of each delivery. In such instances, it is contemplated that one would administer to a patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the other macular or retinal degeneration therapy and the therapeutic agent-based therapy will be required to prevent blindness or a decrease in vision. Various combinations may be employed, where the other macular or retinal degeneration therapy is "A" and the therapeutic agent-based therapy treatment is "B", as exemplified below: A/B/A B/A/B B/B/A A/A/B B/A/A A/B/B B/B/B/A B/B/A/B A/A/B/B A/B/A/B A/B/B/A B/B/A/A B/A/B/A B/A/A/B B/B/B/A A/A/A/B B/A/A/A A/B/A/A A/A/B/A A/B/B/B B/A/B/B B/B/A/B.

Pharmaceutical compositions for use in accordance with the present methods may be formulated in conventional manner using one or more physiologically acceptable carriers or excipients. Thus, activating compounds and their physiologically acceptable salts and solvates may be formulated for administration by, for example, injection, inhalation or insufflation (either through the mouth or the nose) or oral, buccal, parenteral or rectal administration. In one embodiment, the compound is administered locally, at the site where the target cells, e.g., diseased cells, are present, i.e., in the eye or the retina.

Compounds can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions (including cosmetic preparations) may comprise from about 0.00001 to 100% such as from 0.001 to 10% or from 0.1% to 5% by weight of one or more compounds described herein.

In one embodiment, a compound described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, cited in the preceding section, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight; again, reference may be had to Remington's, supra, for further information.

Compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor® from Beiersdorf, Inc. (Norwalk, Conn.).

Compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Compounds may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{10}$ MSO) and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol®) and diethylene glycol monoethyl ether oleate (available commercially as Softcutol®); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol®); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition as herein defined.

In an alternative embodiment, a pharmaceutical formulation is provided for oral or parenteral administration, in which case the formulation may comprises an activating compound-containing microemulsion as described above, but may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Cells, e.g., treated ex vivo with a compound described herein, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Also provided herein are kits, e.g., kits for therapeutic and/or diagnostic purposes. A kit may include one or more compounds described herein, and optionally devices for contacting tissue or cells with the compounds. Devices include needles, syringes, stents, resuspension liquid, and other devices for introducing a compound into a subject.

In any of the forgoing embodiments 1,5-bis(p-aminophenoxy)pentane may be specifically excluded.

In any of the forgoing embodiments 11-cis-retinol may be specifically excluded.

In any of the forgoing embodiments 11-cis-retional palmitate may be specifically excluded.

In any of the forgoing embodiments 13-cis-retinoic acid (accutane) may be specifically excluded.

In any of the forgoing embodiments 2-bromopalmitic acid may be specifically excluded.

In any of the forgoing embodiments 3-aminobenzoic acid ethyl ester methane sulfonate may be specifically excluded.

In any of the forgoing embodiments acetaminophen may be specifically excluded.

In any of the forgoing embodiments adamantylamine may be specifically excluded.

In any of the forgoing embodiments all-trans-retinaldehyde may be specifically excluded.

In any of the forgoing embodiments all-trans-retinoic acid may be specifically excluded.

In any of the forgoing embodiments all-trans-retinol (vitamin A) may be specifically excluded.

In any of the forgoing embodiments all-trans-retinyl plamitate may be specifically excluded.

In any of the forgoing embodiments analine may be specifically excluded.

In any of the forgoing embodiments cyclohexylamine may be specifically excluded.

In any of the forgoing embodiments dapson may be specifically excluded.

In any of the forgoing embodiments diaminophenoxypentane may be specifically excluded.

In any of the forgoing embodiments ethyl m-aminobenzoate may be specifically excluded.

In any of the forgoing embodiments m-aminobenzoic acid may be specifically excluded.

In any of the forgoing embodiments m-phenetidine may be specifically excluded.

In any of the forgoing embodiments N-(4-hydroxyphenyl)retinamide(fenretinide) may be specifically excluded.

In any of the forgoing embodiments N,N-dimethylaniline may be specifically excluded.

In any of the forgoing embodiments N,N-dimethyl-p-phenetidine may be specifically excluded.

In any of the forgoing embodiments N-methylaniline may be specifically excluded.

In any of the forgoing embodiments N-methyl-p-phenetidine may be specifically excluded.

In any of the forgoing embodiments o-phenetidine may be specifically excluded.

In any of the forgoing embodiments p-(n-hexyloxy)aniline may be specifically excluded.

In any of the forgoing embodiments p-(n-hexyloxy)benzamide may be specifically excluded.

In any of the forgoing embodiments p-(n-hexyloxy)benzoic acid hydrazide may be specifically excluded.

In any of the forgoing embodiments p-anisidine may be specifically excluded.

In any of the forgoing embodiments p-ethylanaline may be specifically excluded.

In any of the forgoing embodiments p-ethyoxybenzylamine may be specifically excluded.

In any of the forgoing embodiments p-ethyoxyphenol may be specifically excluded.

In any of the forgoing embodiments phenetidine may be specifically excluded.

In any of the forgoing embodiments piperidine may be specifically excluded.

In any of the forgoing embodiments p-n-boutoxyaniline may be specifically excluded.

In any of the forgoing embodiments p-n-butylaniline may be specifically excluded.

In any of the forgoing embodiments p-n-dodecylaniline may be specifically excluded.

In any of the forgoing embodiments p-nitroaniline may be specifically excluded.

In any of the forgoing embodiments sulfabenzamide may be specifically excluded.

In any of the forgoing embodiments sulfamoxaole may be specifically excluded.

In any of the forgoing embodiments sulfanilamide may be specifically excluded.

In any of the forgoing embodiments tricaine may be specifically excluded.

In addition, any compound cited in the references incorporated herein may also be specifically excluded from any of the forgoing embodiments.

4. Methods

Disclosed herein are methods for treating or preventing an ophtalmologic disorder. An exemplary method comprises administering to a subject, e.g. a subject in need thereof, a therapeutically effective amount of a composition, e.g., a pharmaceutical composition, described herein. A subject in need thereof may be a subject who knows that he has or is likely to develop an opthalmologic disorder.

As discussed above, a disclosed composition may be administered to a subject in order to treat or prevent macular degeneration. Other diseases, disorders, or conditions characterized by the accumulation of retinotoxic compounds, e.g., lipofuscin, in the RPE may be similarly treated (e.g., lipofuscin-based retinopathies).

The methods described herein may be used for the treatment or prevention of any form of retinal or macular degeneration associated with lipofuscin accumulation, such as hereditary or degenerative diseases of the macula as e.g. age-related macular degeneration (AMD). There are two forms of age-related macular degeneration, dry (atrophic) and wet (neovascular or exudative) macular degeneration.

As discussed above, macular degeneration (also referred to as retinal degeneration) is a disease of the eye that involves deterioration of the macula, the central portion of the retina. Approximately 85% to 90% of the cases of macular degeneration are the "dry" (atrophic or non-neovascular) type.

In "dry" macular degeneration, the deterioration of the retina is associated with the formation of small yellow deposits, known as drusen, under the macula. This phenomena leads to a thinning and drying out of the macula. The location and amount of thinning in the retinal caused by the drusen directly correlates to the amount of central vision loss. Degeneration of the pigmented layer of the retina and photoreceptors overlying drusen become atrophic and cause a slow of central vision. This often occurs over a decade or more. Vision loss can occur very rapidly in subjects having strong geographic atrophy. Such subjects may be treated as described herein.

Most people who lose vision from age related macular degeneration have "wet" macular degeneration. In "wet" (neovascular) macular degeneration, abnormal blood vessels from the choroidal layer of the eye, known as subretinal neovascularization grow under the retina and macula. These blood vessels tend to proliferate with fibrous tissue, and bleed and leak fluid under the macula, causing the macula to bulge or move and distort the central vision. Acute vision loss occurs as transudate or hemorrhage accumulates in and beneath the retina. Permanent vision loss occurs as the outer retina becomes atrophic or replaced by fibrous tissues.

Stargardt's disease (STGD) is a recessive form of macular degeneration with an onset during childhood. STGD is characterized clinically by progressive loss of central vision and progressive atrophy of the retinal pigment epithelium (RPE) overlying the macula. Mutations in the human ABCR gene for RmP are responsible for STGD. Early in the disease course, patients show delayed dark adaptation but otherwise normal rod function. Histologically, STGD is associated with deposition of lipofuscin pigment granules in RPE cells, presumably arising from impaired digestion after phagocytosis of shed distal outer-segments. Degeneration of the RPE occurs subsequently, with photoreceptor degeneration appearing late in the disease. This pathological picture has lead to the conclusion that STGD is primarily a defect of the RPE. However, the pattern of early RPE degeneration and preservation of photoreceptors must be reconciled with the observation that RmP is present exclusively in outer segments and not expressed in RPE cells.

Some AMDs are caused by mutations in a gene, such as the genes ABCA4, ELOVL4, PROML1, VMD2, Peripherin/RDS, EFEMP1, TIMP3, and XLRS1. One mutation of the ABC4A gene is G1961E. Macular dystrophies also include the following diseases: Stargardt disease/fundus flavimaculatus (OMIM 248200), which is an autosomal recessive disease characterized by a mutation at chromosome locus 1p21-p22 (STGD1); Stargardt-like macular dystrophy (OMIM 600110), which is an autosomal dominant disease characterized by a mutation at chromosome locus 6q14 (STGD3); Stargardt-like macular dystrophy (OMIM 603786), which is an autosomal dominant disease characterized by a mutation at chromosome locus 4p (STGD4); autosomal dominant "bulll's eye" macular dystrophy, which is an autosomal dominant disease characterized by a mutation at chromosome locus 4p (MCDR2); Bestmacular dystrophy (OMIM 153700), which is an autosomal dominant disease characterized by a mutation at chromosome locus 11q13; adult vitelliform dystrophy (OMIM 179605), which is an autosomal dominant disease characterized by a mutation at chromosome locus 6p21.2-cen; pattern dystrophy (OMIM 169150), which is an autosomal dominant disease characterized by a mutation at chromosome locus 6p21.2-cen; Doyne honeycomb retinal dystrophy (OMIM 126600), which is an autosomal dominant disease characterized by a mutation at chromosome locus 2p16; North Carolina macular dystrophy (OMIM 136550), which is an autosomal dominant disease characterized by a mutation at chromosome locus 6q14-q16.2 (MCDR1); autosomal dominant macular dystrophy resembling MCDR1, which is an autosomal dominant disease characterized by a mutation at chromosome locus 5p15.33-p13.1 (MCDR3); North Carolina-like macular dystrophy associated with deafness, which is an autosomal dominant disease characterized by a mutation at chromosome locus 14p (MCDR4); progressive biforcal chorioretinal atrophy (OMIM 600790), which is an autosomal dominant disease characterized by a mutation at chromosome locus 6q14-q16.2; Sorby's fundus dystrophy (OMIM 136900), which is an autosomal dominant disease characterized by a mutation at chromosome locus 22q12.1-q13.2; central areolar choroidal dystrophy (OMIM 215500), which is an autosomal dominant disease characterized by a mutation at chromosome locus 6p21.2-cen17p13; dominant cystoid macular dystrophy (OMIM 153880), which is an autosomal dominant disease characterized by a mutation at chromosome locus 7p15-p21; and juvenile reitnoschisis (OMIM 312700), which is an X-linked disease characterized by a mutation at chromosome locus Xp22.2 (Michaelides et al. (2003) J. Med. Geneet. 40:641). The methods described herein may be used to treat or prevent any of these genetically inhereted macular dystrophies, provided that they are associated with abnormal lipofuscin accumulation similar to AMD and Stargardt disease.

Other diseases that may be treated or prevented include cone-rod dystrophy, certain types of retinitis pigmentosa, and fundus flavimaculatus.

In one embodiment, a drug is administered to a subject that short-circuits the visual cycle at a step of the visual cycle that occurs outside a disc of a rod photoreceptor cell. For example, as shown in FIG. 3, the drug may react with 11-cis-retinal in the RPE and shunt it to all-trans-retinal while it remains in the RPE. More specifically, the therapeutic may react with 11-cis-retinal to form an intermediate that isomerizes to the all-trans configuration. The all-trans intermediate may then release the therapeutic to form all-trans-retinal. The all-trans-retinal could then be re-processed through the remainder of the visual cycle as normal in the RPE. Thus, the visual cycle would be reduced to a futile cycle, in which all-trans-retinal has little or no opportunity to accumulate in the disc.

In one embodiment, a subject may be diagnosed as having macular degeneration, and then a disclosed drug or combination therapy may be administered. In another embodiment, a subject may be identified as being at risk for developing macular degeneration (risk factors include a history of smoking, age, female gender, and family history). In yet another embodiment, a subject may be diagnosed as having Stargardt's disease, a familial form of macular degeneration. In some embodiments, a drug may be administered prophylactically. In some embodiments, a subject may be diagnosed as having the disease before retinal damage is apparent. For example, a subject may be found to carry a gene mutation for abcr, elovl4, and/or another gene, and thus be diagnosed as having Stargardt's disease before any ophthalmologic signs are manifest, or a subject may be found to have early macular changes indicative of macular degeneration before the subject is aware of any effect on vision. In some embodiments, a human subject may know that he or she is in need of the macular generation treatment or prevention.

Doctors can usually diagnose macular degeneration by examining the eyes with an ophthalmoscope or a slit lamp. Sometimes fluorescein angiography—a procedure in which a doctor injects dye into a vein and photographs the retina—is used to determine the diagnosis. Lipofuscin accumulation may be detected by autofluorescence imaging optionally with confocal scanning laser ophthalmoscope.

In some embodiments, a subject may be monitored for the extent of macular degeneration. A subject may be monitored in a variety of ways, such as by eye examination, dilated eye examination, fundoscopic examination, visual acuity test, angiography, fluorescein angiography, and/or biopsy. Monitoring can be performed at a variety of times. For example, a subject may be monitored after a drug is administered. The monitoring can occur one day, one week, two weeks, one month, two months, six months, one year, two years, and/or five years after the first administration of a drug. A subject can be repeatedly monitored. In some embodiments, the dose of a drug may be altered in response to monitoring.

In some embodiments, the disclosed methods may be combined with other methods for treating or preventing macular degeneration, such as photodynamic therapy. Other methods are further described herein.

In some embodiments, a drug for treating or preventing macular degeneration may be administered chronically. The drug may be administered daily, more than once daily, twice a week, three times a week, weekly, biweekly, monthly, bimonthly, semiannually, annually, and/or biannually.

The therapeutics may be administered by a wide variety routes, described above. In some embodiments, a drug may be administered orally, in the form of a tablet, a capsule, a liquid, a paste, and/or a powder. In some embodiments, a drug may be administered locally, as by intraocular injection. In some embodiments, a drug may be administered systemically in a caged, masked, or otherwise inactive form and activated in the eye (such as by photodynamic therapy). In some embodiments, a drug may be administered in a depo form, so sustained release of the drug is provided over a period of time, such as hours, days, weeks, and/or months.

The therapeutic agents are used in amounts that are therapeutically effective, which varies widely depending largely on the particular agent being used. The amount of agent incorporated into the composition also depends upon the desired release profile, the concentration of the agent required for a biological effect, and the length of time that the biologically active substance has to be released for treatment. In certain embodiments, the biologically active substance may be blended with a compound matrix at different loading levels, in one embodiment at room temperature and without the need for an organic solvent. In other embodiments, the compositions may be formulated as microspheres. In some embodiments, the drug may be formulated for sustained release.

It is noted that disruption of the visual cycle to prevent accumulation of $A_2E$ may impair a subject's night (low-light) vision and might cause night-blindness. Indeed, some of the therapeutics noted herein as appropriate for preventing $A_2E$ accumulation have been used sparingly in humans or withheld from use entirely because of their propensity to cause night-blindness. However, with the recognition that this very cause of night blindness might be turned to the therapeutic and/or preventative treatment of macular degeneration, it is likely that patients in need of such treatment would readily accept some night-blindness in return for sparing of normal vision. This is because the visual cycle described above operates in rod photoreceptors, which operate only at low levels of illumination and do not operate during the day. Therefore, macular function would be little affected by decreases in visual cycle function, while there might be some effect on low light vision at night. At least some patients, and probably most, might readily sacrifice a decrement in night vision for a lessening of the probability that they would eventually lose their cone day vision.

Palmitoylation

In some embodiments, inhibitors of LRAT can be used to modulate palmitoylation of RPE65. RPE65 occurs in at least two forms, membrane-associated (mRPE65) and soluble (sRPE65). As discussed in greater detail below, mRPE65 is a palmitoylated form of RPE65, and sRPE65 is a depalmitoylated form.

The flux of retinoids in the visual cycle can be regulated by the reversible palmitoylation of RPE65 by LRAT. mRPE65 specifically binds long chain all-trans-retinyl esters and mobilizes them for further processing in the visual cycle. The all-trans-retinyl esters are the substrates for the IMH, which converts them into 11-cis-retinol. An all-trans-retinyl ester chaperone role for mRPE65 is required for mobilization of these esters. Regulation is not implicit here because there is no molecular alteration of mRPE65 implied during the operation of the cycle. Several observations reported here, however, bear on this issue and make it exceedingly likely that regulation is imposed on the visual cycle at the RPE65 stage.

The salient facts with respect to invoking regulation at the level of RPE65 can be summarized as follows: (1) mRPE65 and sRPE65 show different and complementary retinoid binding profiles. mRPE65 specifically binds all-trans-retinyl esters and makes them available for IMH processing, while sRPE65 specifically binds vitamin A, making it available for LRAT. (2) the predominant form of RPE65 as isolated is sRPE65, and not mRPE65. (3) mRPE65 and sRPE65 differ in their states of palmitoylation. (4) the reversible sRPE65 to mRPE65 interconversion is cooperative and catalyzed by LRAT, so that small changes in the levels of mRPE65 will have a magnified effect on isomerization. (5) mRPE65 acts as a palmitoyl donor for 11-cis-retinol in the presence of LRAT, revealing a dual role for mRPE65, as a retinoid binding protein and an acyl donor which limits isomerization by decreasing the levels of mRPE65, and (6) all-trans-retinyl esters have the opposite effect, because they drive sRPE65 to mRPE65.

A simple working model can be generated to synthesize the experimental observations made here into an important regulatory element in the control of the visual cycle. FIGS. 13A-B show how the regulatory elements described might direct the flow of retinoids in vision. In the dark, when formation of the visual chromophore 11-cis-retinal is not required, sRPE65-is expected to be the predominant form of RPE65. The sRPE65 is generated by the palmitoylation of 11-cis-retinol by mRPE65, and perhaps also by the hydrolysis of mR-PE65 by palmitoyl esterases activated in the dark. It is quite conceivable that G-protein coupled events are involved here. Light flips the switch (FIG. 13A), because the photoisomerization of rhodopsin in the photoreceptors results in a flux of vitamin A to the RPE. The RPE is primed to chaperone vitamin A to LRAT to generate all-trans-retinyl esters, the substrates for IMH. The all-trans-retinyl esters have a second role, as shown here, to drive the sRPE65 to mRPE65 conversion. This process is cooperative, so that small changes in the concentration of mRPE65 will have large effects on the rate of processing of all-trans-retinyl esters and isomerization. The mRPE65 directs the flow of all-trans-retinyl esters to IMH, where it is processed to form 11-cis-retinol. Once the 11-cis-retinol is formed, it can be partitioned directly into 11-cis-retinal, the chromophore of rhodopsin, by binding to cRALBP, with subsequent oxidation by 11-cis-retinol dehydrogenase. This flow of chromophore occurs to the photoreceptors when opsin is made available as a consequence of the bleaching of rhodopsin in the light. The exothermic binding of opsin with 11-cis-retinal to form rhodopsin drives this process.

The switch would be turned back off in the dark because 11-cis-retinol is palmitoylated, using mRPE65 as the acyl donor to form 11-cis-retinyl palmitate, the storage form of the chromophore, and sRPE65. This shuts the system down, because the latter is a chaperone for vitamin A, not all-trans-retinyl esters, and is unable to facilitate IMH processing. Again, because of the cooperativity of the process, a small shift in concentration of mRPE65 will have a large effect on the rate of 11-cis-retinol synthesis. The palmitoylation of 11-cis-retinol by mRPE65 also would explain the putative turnover of mRPE65 during the operation of the visual cycle, although as suggested above, additional factors may also enhance mRPE65 hydrolysis. Thus, the proposed switch would operate very simply: the rise in all-trans-retinyl ester levels facilitates chromophore biosynthesis because mRPE65 is regenerated to direct retinoid flow to the IMH. The rise in 11-cis-retinol formation switches off the system because it drives the mRPE65 to sRPE65 conversion. It is already known that added 11-cis-retinol is a powerful inhibitor of chromophore biosynthesis in vivo, and it is shown here in FIG. 12A that this inhibition is at least in part due to the switch effect. Finally, the existence of this switch-based regulatory element is also consistent with the observation that 11-cis-retinoid regeneration in the dark is a very sluggish affair.

The studies described here are of general interest beyond their impact on visual processing. Certainly, palmitoyl switch mechanisms could operate in a variety of signal transduction contexts, in addition to the one explored here. On a biochemical level the molecular basis of the differences in ligand binding selectivity between mRPE65 and sRPE65 are related only to differences in their extents of palmitoylation. Protein palmitoylation represents a well-known post-translational modification, whose principle roles are to enhance the hydrophobicity of proteins, targeting them to membranes, and also to enhance protein-protein interactions in certain cases. There is no doubt that in the case of RPE65 palmitoylation-mediated transition of sRPE65 to mRPE65, membrane targeting is an outcome. However, the studies reported here reveal two other roles for palmitoylation. First, as mentioned above, palmitoylation alters the ligand binding specificity of the modified protein. Whether the palmitoyl group(s) of mRPE65 directly interacts with the all-trans-retinyl esters, thus enhancing binding for these molecules through hydrophobic interactions, or whether palmitoylation causes a conformational change in the protein is currently unknown. Second, we also show that a palmitoylated protein (mRPE65) can function as a palmitoyl donor. Reversible palmitoylation has been described and this reversibility may be of regulatory significance (Houslay 1996; Mumby 1997; Bijlmakers and Marsh 2003; Qanbar and Bouvier 2003). This is especially interesting in signal transduction processes where small G proteins are palmitoylated (Milligan 1995; Morello 1996; Mumby 1997; Resh 1999; Chen and Manning 2001; El-Husseini and Bredt 2002; Bijlmakers and Marsh 2003; Qanbar and Bouvier 2003). In these cases, removal of a palmitoyl moiety is thought to occur by means of an esterase, but an acyl carrier role for the small G-proteins may not have been addressed (Mumby 1997; Resh 1999; Linder and Deschenes 2003).

LRAT catalyzes the interconversion of mRPE65 and sRPE65, and hence this enzyme is bi-functional because it is also responsible for the bulk synthesis of all-trans-retinyl esters in the visual cycle. In the studies reported here, mRPE65 acts as the palmitoyl donor, rather than lecithin. This result is surprising because hitherto LRAT had been considered a rather narrowly specific enzyme that used lecithin (i.e. DPPC) as an acyl donor and a retinol as the acyl acceptor (Cañada et al., 1990; Barry et al., 1989; Saari 2000). With respect to acyl donor function, neither the phosphatidylethanolamines nor the phosphatidylserines substitute for lecithin (Cañada et al., 1990).

LRAT is the founder member of an expanding group of proteins, many of which are of unknown function (Jahng et al., 2003b). The proteins of unknown function include class II tumor suppressors and EGL-26, a putative enzyme that mediates morphogenesis in *C. elegans* (Hanna-Rose 2002; Anantharaman and Arvind 2003). These proteins should be considered as possible palmitoyl transferase candidates. Along these lines, it is interesting to note that the identification of dedicated palmitoyl transferase enzymes has not been forthcoming, and the possibility of chemical, rather than enzymatic palmitoylation, is a considered alternative (Mumby 1997; Resh 1999; Linder and Deschenes 2003; Bijlmakers and Marsh 2003). Accordingly, compounds identified herein as modulators or inhibitors of LRAT may be considered prototypical palmitoyl transferase modulators or inhibitors, and may be used to modulate other palmitoyl transferases in the expanding LRAT class.

5. Screening Methods

Suitable drugs may be identified by a variety of screening methods. For example, a candidate drug may be administered to a subject that has or is at risk for having macular degeneration, e.g., an animal that is an animal model for macular degeneration, and the accumulation of a retinotoxic compound, such as $A_2E$, can be measured. A drug that results in reduced accumulation of a retinotoxic compound compared to a control (absence of the drug) would thus be identified as a suitable drug. Alternatively, photoreceptor disks may be analyzed for the presence of all-trans-retinal, N-retinylidene-PE, and/or $A_2E$. Animal models that have rapid development of macular degeneration are of considerable interest because naturally-occurring macular degeneration typically takes years to develop. A number of animal models are accepted models for macular degeneration. For example, the abcr –/– knockout mouse has been described as a model for macular degeneration and/or lipofuscin accumulation, as has been the elovl4 –/– knockout mouse. In addition, knockout mice deficient in monocyte chemoattractant protein-1 (Ccl-2; also known as MCP-1) or it cognate receptor, C-C chemokine receptor-2 (Ccr-2), have also been described as accelerated models for macular degeneration.

In addition, in vitro models of the visual system may facilitate screening studies for drugs that inhibit or short circuit the visual cycle. In vitro models can be created by placing selected intermediates in solution with appropriate enzymes and other necessary cofactors. Alternatively, an in vitro RPE culture system may be employed. For example, LRAT inhibition can be tested by adding a candidate drug to a solution containing LRAT and a substrate for LRAT, and measuring accumulation of an expected product. Analogous systems are envisioned for the other potential inhibition targets described herein.

Agents, such as small molecules, that inhibits one of the enzymes of the visual cycle or shortcircuits the visual cycle may also be identified. For example, agents that bind to one of these enzymes may be identified. Screening assays may comprise contacting an enzyme with a test agent and determining whether the agent binds to the enzyme. An enzyme of biologically active fragment thereof may be used. The enzyme or fragment may be labeled, such as with a fluorophore. Screening assays may also comprise contacting an enzyme with its substrate in the presence of a test agent and determine whether the test agent prevents binding of the enzyme to the substrate. These assays may be adapted to highthroughput screening assays.

Agents, such as small molecules, that inhibit vitamin A delivery to the eye may be identified in screening methods. A method may comprise contacting an RBP with a test agent in the presence of vitamin A and measuring the amount of vitamin A bound to RBP in the presence relative to the absence of the test agent. Another method may comprise contacting an RBP with a test agent in an vitro eye model, adding vitamin A, and determining the amount of vitamin A that is imported into the eye model in the presence relative to the absence of the test agent. Other screening assays may comprise contacting an RBP and an RBP receptor optionally in the presence of vitamin A and determining the amount of RBP bound to the RBP receptor in the presence relative to the absence of the test agent.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

The present description is further illustrated by the following examples, which should not be construed as limiting in any way. The contents of all cited references (including literature references, issued patents, published patent applications as cited throughout this application) are hereby expressly incorporated by reference.

Example 1 in vitro

Materials: Frozen bovine eyecups devoid of retinas were purchased from W. L. Lawson Co., Lincoln, Nebr. Ammonium bicarbonate, BSA, ethylenediaminetetraacetic acid (EDTA), guanidine HCl, imidazole, DEAE-Sepharose, phenyl-Sepharose CL-4B, all-trans-retinol, all-trans-retinyl palmitate, α-Cyano-4-hydroxycinnamic acid and Trizma® base were from Sigma-Aldrich. Dithiothreitol was from ICN Biomedicals Inc. 11-cis-Retinol and 11-cis-retinyl palmitate were synthesized by following the procedure described elsewhere (Shi et al., 1993). Anagrade™ CHAPS and dodecyl maltoside were from Anatrace. HPLC grade solvents were from Sigma-Aldrich Chemicals. Anti RPE65 (NFITKVN-PETLETIK) antibody was obtained from Genmed Inc and anti-LRAT antibody was provided by Prof. Dean Bok (University of California at Los Angeles). rHRPE65 baculovirus was provided by Prof. Jian-Xin Ma (University of South Carolina). Hank's TNM-FH Insect medium was obtained from JRH Biosciences. sf21 cells were laboratory stock from Prof. Steven Harrison's laboratory (Harvard Medical School). Broad spectrum EDTA-free protease inhibitor cocktail was obtained from Roche Biosciences. Nickel-NTA resin and Nickel-NTA spin column were purchased from Qiagen Inc. The precast gels (4-20%) for sodium dodecylsulfate-polyacrlyamide gel electrophoresis, BenchMark prestained and Magic molecular weight markers were from Invitrogen. DEAE Sepharose was from Amersham Biosciences. Buffers were changed by dialysis in the request buffer overnight in a slide-a-lyser™ cassette from Pierce (10 KDa MWCO). RPE65 solutions were concentrated with an Amicon Ultra™ centrifugal filtration device (30 KDa-cutoff) from Millipore Corp. All reagents were analytical grade unless specified otherwise.

Methods

Purification of mRPE65, sRPE65 and rHRPE65: Purification was performed as described before (Ma et al., 2001). The purities of these proteins were verified by silver staining or Coomassie staining and Western blot (1:4000 primary antibody—1 h at room temperature and 1:4000 secondary antibody—0.5 h at room temperature).

Purification of rCRALBP: Purification was performed as previously described (25). The purities of these proteins were verified by silver staining or Coomassie staining and Western blot analysis (1:4000 primary antibody—1 h at room temperature and 1:4000 secondary antibody—0.5 h at room temperature).

Fluorescence binding assays: RPE65 in PBS, 1% CHAPS, pH 7.4 was used in the fluorometric titration studies. Protein concentrations were measured by a modified Lowry method (Lowry et al., 1951). All titrations were performed at 25° C. The samples in PBS buffer were excited at 280 nm and the fluorescence was scanned from 300 to 500 nm. Fluorescence measurements, using 450 µL quartz cuvettes with a 0.5 cm path length, were made at 25° C. on a Jobin Yvon Instruments, Fluoromax 2 employing the right-angle detection method.

The fluorescence of the protein solution was measured after equilibrating it at 25° C. for 10 min. The sample was then titrated with a solution of retinoid dissolved in dimethyl sulfoxide. In each titration, to a 250 µL solution of the protein an equal amount of retinoid, typically 0.2 µL. was added and thoroughly mixed before allowing it to equilibrate for 10 min prior to recording the fluorescence intensity. The addition of dimethyl sulfoxide (0.1% per addition) did not have any effect on the fluorescence intensity. The binding constant ($K_D$) was calculated from the fluorescence intensity by using the following equation (Gollapalli et al., 2003).

$$P_0 \alpha = \frac{R_0 \alpha}{n(1-\alpha)} - \frac{K_D}{n}$$

where $P_0$=Total protein concentration, $$\alpha = \frac{F_{max} - F}{F_{max} - F_0},$$

n=number of independent binding sites, $R_0$=Total retinoid concentration at each addition, $K_D$=dissociation constant, $F_{max}$=Fluorescence intensity at saturation, and $F_0$=Initial fluorescence intensity.

Competitive binding of retinoic acid (all-trans and 13-cis) and all-trans-retinyl palmitate to RPE65: Buffer exchange experiments were performed to investigate the abilities of the retinoic acids (all-trans and 13-cis) to displace all-trans-retinyl palmitate binding from RPE65. To RPE65 (0.5 µM) (PBS, 1% CHAPS, pH 7.4), was added 6 µM of retinoic acid (all-trans and 13-cis) and incubated at 4° C. for 30 min. A control sample of RPE65 was incubated minus retinoic acids at 4° C. for 30 min. At the end of this incubation, the samples were incubated for 30 min with $^3$H-all-trans-retinyl palmitate (0.65 µM, 20.31 Ci/mmol). At the end of this incubation period the buffer (PBS-1% CHAPS) was exchanged $10^4$ fold with a Centricon 30K MWCO filter. The sample retained and the buffer flow through were counted on a liquid scintillation counter, to measure the amount of $^3$H-all-trans-retinyl palmitate retained.

Effect of all-trans Retinoic acid (atRA), 13-cis-Retinoic acid (13cRA) and N-(4-hydroxyphenyl)retinamide (4-HPR) on IMH: To 1 mL of buffered suspension of RPE membranes (100 mM Tris pH 8.0, 76.7 µg of protein) was added 60 µM or 6 µM of atRA, 13cRA or 4-HPR and incubated at room temp. for 15 min. A control reaction mixture without any inhibitor was also incubated at room temperature for 15 min. At the end of the 15 min incubation, all-trans-retinol [11-12-$^3$H$_2$] (0.2 µM) was added to the reaction mixtures (100 mM Tris pH 8.0, 76.7 µg of RPE protein, 0.2% BSA 100 µM of DPPC, 1 mM of DTT and 0.2 µM all-trans-retinol [11-12-$^3$H$_2$]) and incubated at room temperature for 30 min. At the end of this 30 minutes of incubation, an aliquot of the reactions were quenched to verify the equal addition of all-trans-retinol [11, 12-$^3$H$_2$] and the effect of these inhibitors on LRAT. After this the control reaction mixture was incubated with atRA (60 & 6 µM), 13cRA (60 & 6 µM) or 4-HPR (60 & 6 µM) for 15 min. Now all the reaction mixtures were incubated with 30 µM of apo-rCRALBP (100 mM Tris pH 8.0, 7.7 µg of RPE protein, 0.2% BSA 100 µm of DPPC, 1 mM of DTT 30 µM aporCRALBP and 0.2 µM all-trans-retinol [11-12-$^3$H$_2$]) at 37° C. for 30 minutes. At the end of this incubation period the 200 µL reaction mixture was quenched by the addition of 750 µL ice cold methanol after which 100 µL of 1M sodium chloride solution was added, and 500 µl hexane (containing butylated hydroxy toluene at 1 mg/mL) was added to effect extraction of the retinoids. The retinoids were analyzed as previously described (27). The amount of 11-cis-retinol formed was used as a measurement of IMH activity. All experiments were performed in triplicate and the average values of these measurements were used for analysis.

$^3$H$_2$ Palmitoylation of rHmRPE65: 6×His-recombinant human membrane associated RPE65 was expressed in recombinant baculovirus in sf21 insect cells. The sf21 cells were transfected with recombinant baculovirus followed by incubation for 8 hrs at 25° C., followed by addition of (0.09 µM) of $^3$H$_2$ palmitic acid (0.5 mCi/mL). The culture was incubated at 25° C. for 48 h. A similar culture with non-radioactive palmitic acid (0.09 µM) was grown as control. At the end of the expression, the cells were harvested at 500×g. The cells were lysed in 100 mM phosphate buffer with 500 mM NaCl-pH8.0, 5 mM imidazole and 6 M guanidine HCl. The lysis buffer contained the appropriate amount of protease inhibitor cocktail as per the manufacture's instructions. The lysed cells were then centrifuged at 100,000×g to pellet the cell debris, and purified on a Nickel-NTA column following the manufactures instructions. The purified protein solution was divided into two parts: (1) was treated for 16 h with 0.5 M Tris pH 8.0 and (2) was treated for 16 h with 0.5 M hydroxyl amine pH 8.0. The protein samples were then analyzed by sodium dodecylsulfate-polyacrlyamide gel electrophoresis, Western blot analysis, and autoradiography.

MALDI-TOF analysis of purified bovine mRPE65 and sRPE65: MALDI-TOF mass analysis was performed using a Voyager-DE STR from Applied Biosystems. mRPE65 and sRPE65 were purified as described above. The gel band containing pure mRPE65 and sRPE65 was dehydrated in acetonitrile for 10 min. Gel pieces were covered with dithiothreitol (10 mM) in ammonium bicarbonate (100 mM) to reduce the proteins for 1 h at 56° C. After cooling to room temperature, the reducing buffer was removed. The gel washing/dehydration cycle was repeated 3 times with ammonium bicarbonate/acetonitrile before trypsin (12.5 ng/µL, 5 µL/mm$^2$ gel, overnight) digestion at 37° C. Gel slices were centrifuged and the supernatant was collected. Peptides were further extracted by one change of 20 mM ammonium bicarbonate and three changes 50% acetonitrile (20 minutes between changes) at 25° C. α-Cyano-4-hydroxycinnamic acid (0.5 µL, 10 mg/mL) was used as the matrix for each sample (0.5 µL). Samples were run in the reflector mode with 20000V of accelerating voltage and 200 nsec of extraction delay time. The laser intensity was 1900-2300 and 100-200 laser shots were collected for each spectrum. The acquisition mass range was 750-4500 Da with a 600 Da low mass gate.

Effect of sRPE65 on tLRAT mediated esterification: The activity of LRAT was determined by monitoring the formation of tLRAT catalyzed retinyl esters from added all-trans-retinol [11,12-$^3$H$_2$] sRPE65 and/or DPPC/dodecyl maltoside. In all of the studies reported here truncated LRAT (tLRAT) is used (Jahng et al., 2003b). This form of LRAT has the two N and C-terminal transmembrane domains of LRAT truncated, and is His-tagged which allows for the bacterial expression of LRAT and for its full purification (Bok et al., 2003). LRAT has never been purified and is not expressible in bacteria. Kinetic studies on LRAT and tLRAT show them to behave identically (Bok et al., 2003). In the current experiments, the reaction mixture (volume 0.1 mL) contains 100 mM Tris (pH 8.4), 5 µm of tLRAT, 200 µM DPPC/0.1% dodecyl maltoside and/or 0.04 µM sRPE65, 1 mM dithiothreitol and 0.2 µM of all-trans-retinol [11,12-$^3$H$_2$] and incubated for 10 min at room temperature. After 10 min the reaction was quenched with 500 µL methanol, 100 µL of water and 500 µL of hexane. The amount of all-trans-retinyl palmitate [11,12-$^3$H$_2$] formed as determined by normal phase HPLC and was used as a measure of activity. Each experiment was done in duplicate, and the data points used are an average of these two points.

mRPE65 concentration-dependent esterification of vitamin A: The effect of mRPE65 concentration on the rates of all-trans-retinyl palmitate formation was determined by monitoring the tLRAT catalyzed formation of all-trans-retinyl palmitate from added [11,12-$^3$H$_2$]-all-trans-retinol and mRPE65. It should be noted that all-trans-retinyl palmitate formed from mRPE65 and vitamin A was identified both by its mass spectroscopic and chromatographic properties. The reaction mixture (volume 0.1 mL) contains 100 mM Tris (pH 8.4), 5 µm of tLRAT 0.3% CHAPS, 1 mM dithiothreitol and 5 µM of all-trans-retinol [11,12-$^3$H$_2$] and mRPE65 (0, 0.008, 0.02, 0.028, 0.04, 0.052, 0.06 and 0.08 µM) incubated for 10 min at room temperature. After 10 min the reaction was quenched with 500 µL methanol, 100 µL of water and 500 µL of hexane. The amount of all-trans-retinyl palmitate [11, 12-$^3$H$_2$] formed as determined by normal phase-HPLC and was used as a measure of activity. The kinetic paramaters $K_M$ ($K_{app}$) and N were calculated as described before (Segal 1993). Each experiment was done in triplicate, and the data points used are an average of these three points. The standard errors are presented as error bars.

RPE65 mediated reversible palmitoylation of vitamin A: The reversibility of the palmitoylation of vitamin A, mediated by tLRAT in the presence of RPE65 was investigated. A reaction mixture consisting of 100 mM Tris pH 8.4, 0.06 µM of mRPE65, 1 mM dithiothreitol, 1 mM EDTA 5 µM of tLRAT and 5 µM of all-trans-retinol was incubated for 1 hr. This was followed by addition of 5 µM of all-trans-retinol [11,12-$^3$H$_2$] (4.05 Ci/mmol). Aliquots were removed from the reaction after 0, 2, 7, 10, 20 and 35 min and the reaction was quenched by the addition of 500 µL of methanol, 100 µL of H$_2$O and extracted with 500 µL of hexane. The all-trans-retinyl esters were separated from all-trans-retinol and the specific activities for each fraction was calculated as described before (Gollapalli and Rando 2003). Each time point was done in triplicates and the average value was used. The standard errors are presented as error bars.

In vitro conversion of mRPE65 to sRPE65: Purified mRPE65 (0.02 µM) was incubated with tLRAT (5 µM) and all-trans-retinol (0.2 µM) at room temperature for 2 h. At the end of the reaction the reaction mixture was irradiated with UV light (365 nm) for 15 min to destroy the endogenous retinoids. The solution was dialyzed against a dialysis buffer containing 100 mM phosphate buffer (pH 8.0), 500 mM NaCl, 5 mM imidazole and 1% CHAPS. The dialyzed reaction mixture was then concentrated and passed through a Nickel-NTA spin column to remove the 6×His tagged tLRAT. The flow through was concentrated and used in the fluorescence binding assay as described above. The removal of tLRAT was confirmed by Western blot (1:4000 primary antibody—1 hr analysis at room temperature and 1:4000 secondary antibody—0.5 hr at room temperature).

Isomeric preference of the mRPE65/tLRAT mediated esterification of retinols: The effect of mRPE65 on the processing of 11-cis-and all-trans-retinols was determined by monitoring the formation of tLRAT catalyzed retinyl esters from added all-trans-retinol [11,12-$^3$H$_2$], 11-cis-retinol [15-$^3$H] and mRPE65. The reaction mixture (volume 0.1 mL)

contains 100 mM Tris (pH 8.4), 5 μM of tLRAT 0.3% CHAPS, 1 mM dithiothreitol and 0.2 μm of all-trans-retinol [11,12-$^3$H$_2$] or 11-cis-retinol [15-$^3$H] and mRPE65 (0.02 μM) or 200 μM/0.4% DPPC/BSA was incubated for 10 min at room temperature. After 10 min the reaction was quenched with 500 μL methanol, 100 μL of water and 500 μL of hexane. The amount of retinyl palmitate formed, as determined by normal phase-HPLC, was used as a measure of activity. Each experiment was done in triplicate, and the data points used are an average of these three points. The standard error was presented as error bars.

Effect of 11-cis-retinol mediated depalmitoylation of mRPE65 on the generation of 11-cis-retinol: To 1 mL of buffered suspension of RPE membranes (100 mM Tris pH 8.0, 80 μg of protein) was added 10 μm of 11-cis-retinol and incubated at room temp. for 45 min. A control reaction mixture without 11-cis-retinol was also incubated at room temperature for 45 min. At the end of the 45 min incubation, the reaction mixtures were exposed to UV light (354 nm) for 10 min to destroy the 11-cis-retinoids. All-trans-retinol [11-12-$^3$H$_2$] (0.1 μM) was then added to the reaction mixtures (100 mM Tris pH 8.0, 80 μg of RPE protein 5% BSA and 0.1 μM all-trans-retinol [11-12-$^3$H$_2$], and incubated at 37° C. 100 μL aliquot of the reactions were quenched after 0, 5, 10, 15, 20, 30, 45, 60, 90, 120 and 150 min by the addition of 500 μL methanol after which 100 μL of H$_2$O was added, and 500 μl hexane (containing butylated hydroxy toluene at 1 mg/mL) was added to effect extraction of the retinoids. The retinoids were analyzed as previously described (Winston and Rando 1998). The amount of 11-cis-retinol formed was used as a measurement of IMH activity. All experiments were performed in triplicate and the average values of these measurements were used for analysis.

Blocking RPE65 Binding to Retinyl Esters

Effect of all-trans Retinoic acid (atRA), 13-cis-Retinoic acid (13cRA) and N-(4-hydroxyphenyl)retinamide (4-HPR) on IMH: To 1 mL of buffered suspension of RPE membranes (100 mM Tris pH 8.0, 76.7 μg of protein) was added 60 μM or 6 μm of atRA, 13cRA or 4-HPR and incubated at room temp. for 15 min. A control reaction mixture without any inhibitor was also incubated at room temperature for 15 min. At the end of the 15 min incubation, all-trans-retinol [11-12-$^3$H$_2$] (0.2 μM) was added to the reaction mixtures (100 mM Tris pH 8.0, 76.7 μg of RPE protein, 0.2% BSA 100 μM of DPPC, 1 mM of DTT and 0.2 μM all-trans-retinol [11-12-$^3$H$_2$]) and incubated at room temperature for 30 min. At the end of this 30 minutes of incubation, an aliquot of the reactions were quenched to verify the equal addition of all-trans-retinol [11, 12-$^3$H$_2$] and the effect of these inhibitors on LRAT. After this the control reaction mixture was incubated with atRA (60 & 6 μM), 13cRA (60 & 6 μM) or 4-HPR (60 & 6 μM) for 15 min. Now all the reaction mixtures were incubated with 30 μM of apo-rCRALBP (100 mM Tris pH 8.0, 7.7 μg of RPE protein, 0.2% BSA 100 μM of DPPC, 1 mM of DTT 30 μM apo-rCRALBP and 0.2 μM all-trans-retinol [11-12-$^3$H$_2$]) at 37° C. for 30 minutes. At the end of this incubation period the 200 μL reaction mixture was quenched by the addition of 750 μL ice cold methanol after which 100 μL of 1M sodium chloride solution was added, and 500 μl hexane (containing butylated hydroxy toluene at 1 mg/mL) was added to effect extraction of the retinoids. The retinoids were analyzed as previously described (27). The amount of 11-cis-retinol formed was used as a measurement of IMH activity. All experiments were performed in triplicate and the average values of these measurements were used for analysis.

FIG. 4A, B, C shows data for the specific binding of all-trans-retinoic acid to purified RPE65. As shown in FIG. 4A, the binding of all-trans-retinoic acid to RPE65 led to an exponential decay in protein fluorescence. This decay follows a saturable binding isotherm (FIG. 4B), and yields an average $K_D$ for binding of approximately 109 nM (SD=10 nM, N=4) (FIG. 4C). Similar data are shown in FIG. 5A, B, C for 13-cis-retinoic acid, yielding an average $K_D$ for binding of approximately 195 nM (SD=20 nM, N=4) (FIG. 5C). These experiments show that both retinoic acids specifically bind to RPE65 with high affinities. By way of comparison, under the same binding conditions, all-trans-retinyl palmitate binds to RPE65 with a $K_D$=47 nM (data not shown). To further assess specificity of binding, the binding interactions of an additional retinoid, N-(4-hydroxyphenyl)retinamide (Fenretinide):

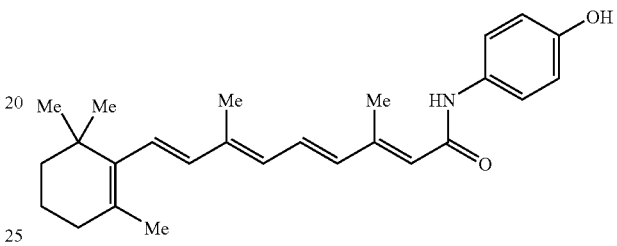

with RPE65 was studied. The binding of N-(4-hydroxyphenyl)retinamide to RPE65 is expected to be considerably weaker than for the retinoic acids, because analogs in the retinamide series only weakly induce night blindness. In fact, N-(4-hydroxyphenyl)retinamide binds rather weakly to RPE65. Data shown in FIG. 6A, B, C, yield an average $K_D$ for binding of approximately 3547 nM (SD=280 nM N=4) (FIG. 6C). Thus the observed weak binding for N-(4-hydroxyphenyl)retinamide is what is predicted for the hypothesis that RPE65 is the night blindness target.

B. Retinoic Acid Displaces all-trans-retinyl palmitate from RPE65.

Competitive binding of retinoic acid (all-trans and 13-cis) and all-trans-retinyl palmitate to RPE65: Buffer exchange experiments were performed to investigate the abilities of the retinoic acids (all-trans and 13-cis) to displace all-trans-retinyl palmitate binding from RPE65. To RPE65 (0.5 μM) (PBS, 1% CHAPS, pH 7.4), was added 6 μM of retinoic acid (all-trans and 13-cis) and incubated at 4° C. for 30 min. A control sample of RPE65 was incubated minus retinoic acids at 4° C. for 30 min. At the end of this incubation, the samples were incubated for 30 min with $^3$H-all-trans-retinyl palmitate (0.65 μM, 20.31 Ci/mmol). At the end of this incubation period the buffer (PBS-1% CHAPS) was exchanged 10$^4$ fold with a Centricon 30K MWCO filter. The sample retained and the buffer flow through were counted on a liquid scintillation counter, to measure the amount of $^3$H-all-trans-retinyl palmitate retained.

Figure 7:
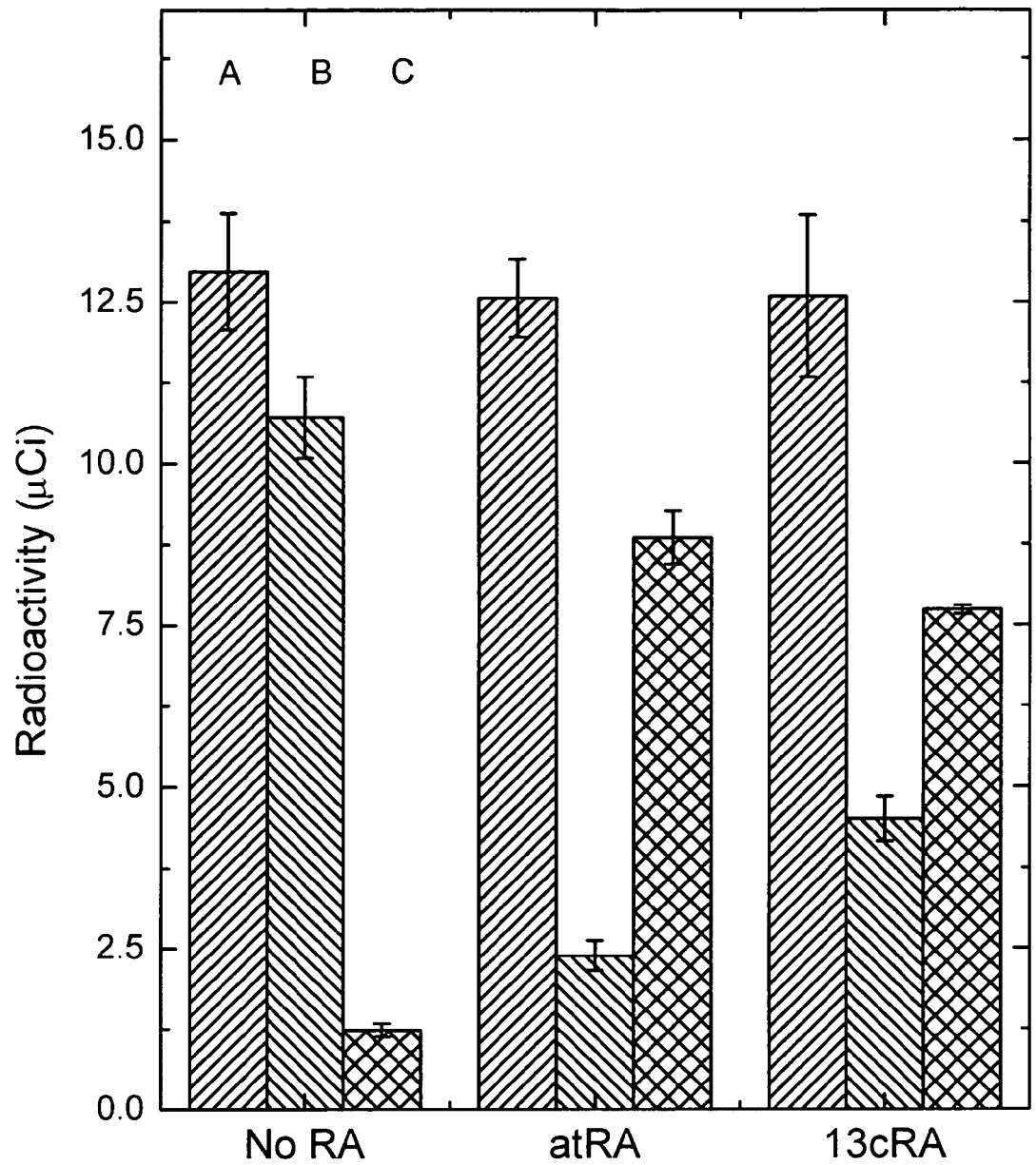
FIG. 7 depicts data concerning competitive binding between all-trans-retinoic acid and all-trans-retinyl palmitate to RPE65.

The direct binding studies reported above for the retinoic acids are not determinative as to whether these molecules are competitive with the binding of all-trans-retinyl esters, the physiologically relevant ligands of RPE65. This can readily be shown by pre-binding $^3$H-all-trans-retinyl palmitate to RPE65 and showing that all-trans-retinoic acid competes with the binding (FIG. 7). This experiment was performed by first incubating RPE65 with all-trans-retinoic acid or 13-cis-retinoic acid and (−) retinoic acid (control), following which the protein was incubated for 30 min with $^3$H-all-trans-retinyl palmitate. Excess retinoids were removed by buffer exchange and the flow through and retained solutions were counted using a liquid scintillation counter. The data show that the retinoic acids and all-trans-retinyl esters apparently compete for the same binding-site on RPE65.

C. Retinoic Acids Inhibit RPE65 Function

Figure 8:
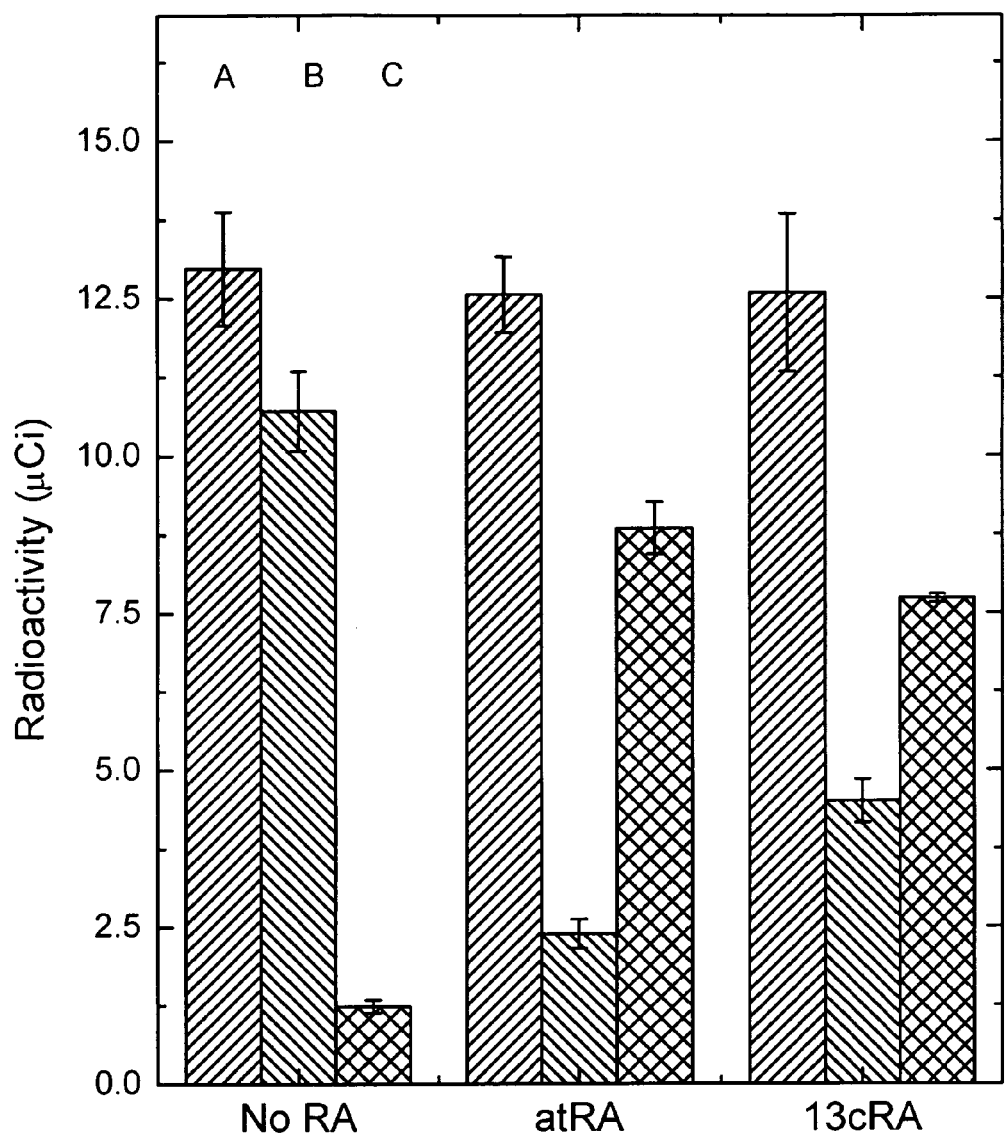
FIG. 8 depicts data concerning the effect of all-trans Retinoic acid (atRA), 13-cis-Retinoic acid (13cRA) and N-(4-hydroxyphenyl)retinamide (4-HPR) on 11-cis-retinol biosynthesis.

RPE65 is the chaperone for all-trans-retinyl esters and, as such, is essential for the mobilization of these hydrophobic molecules for isomerization. In the current studies, a bovine retinal pigment epithelial membrane system is used to process added all-trans-retinol (vitamin A) to form 11-cis-retinol. Since RPE65 is essential for the biosynthesis of 11-cis-retinol (4,8,11), inhibitors of it could block this synthesis. In the experiments shown in FIG. 7 the off-rate for the binding of all-trans-retinyl esters to RPE65 is sufficiently slow to allow the complex to survive centrifugation on Centricon spin columns. The same is true for all-trans-retinoic acid (data not shown). This suggests that the order of incubation of inhibitors of RPE65 would be expected to be important to reveal effective inhibition. Pre-incubation of these membranes with vitamin A rapidly produces all-trans-retinyl esters through rapid esterification mediated by LRAT. The synthesized all-trans-retinyl esters are tightly bound to RPE65, and then processed into 11-cis-retinol by IMH. This system is not susceptible to inhibition by all-trans or 13-cis-retinoic acids incubated at 60 µM (data not shown). This is the expected result because the retinoic acids are known not to directly inhibit IMH. However, pre-incubation with the retinoic acids produced a markedly different result, as shown in FIG. 8. In this case, substantial inhibition of 11-cis-retinol formation occurs in the presence of the retinoic acids because they have access to RPE65. Interestingly, the inhibition observed with N-(4-hydroxyphenyl)retinamide proved to be substantially weaker (FIG. 8). This is the expected result, given its relatively weak affinity for RPE65.

D. The Steroselective Binding of Vitamin A by sRPE65

Figure 2:
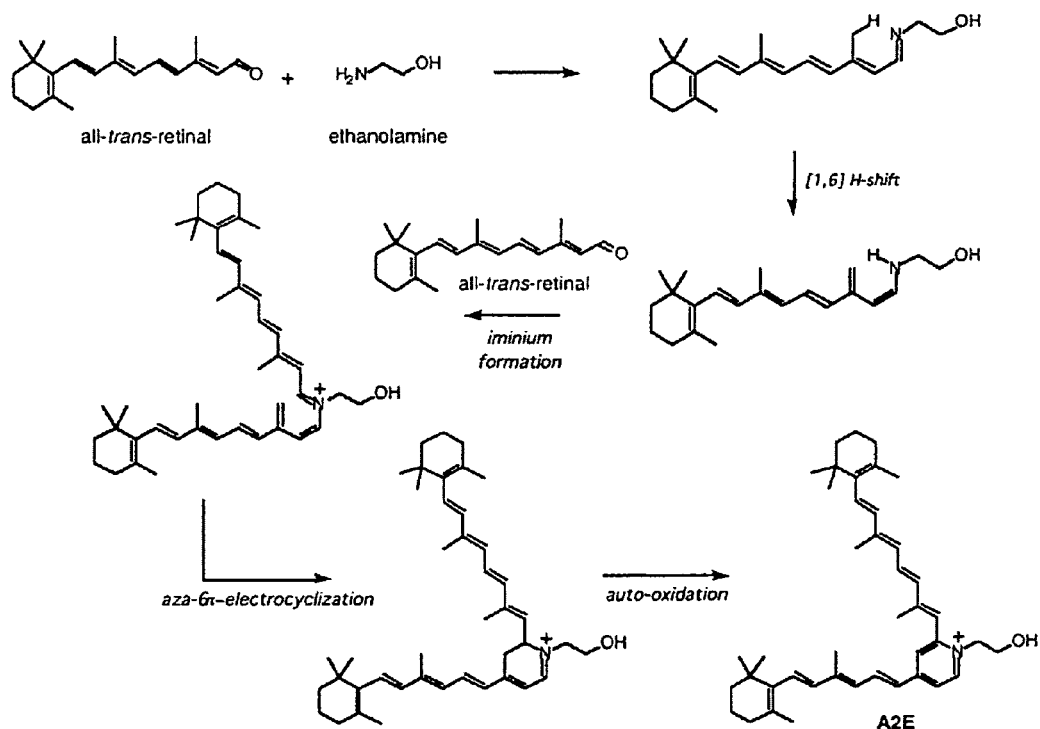
FIG. 2 depicts the synthesis of $A_2E$.

As mentioned above, membrane associated RPE65 (mRPE65) stereoselectively binds all-trans-retinyl palmitate. In this example, the binding of retinoids to sRPE65 is measured by the fluorescence methodology already described (Gollapalli, D. R., Maiti, P., Rando, R. R. (2003) RPE65 operates in the vertebrate visual cycle by stereospecifically binding all-trans-retinyl esters. Biochemistry 42, 11824-30.). The excitation wavelength was at 280 nm and the emission was observed through 0.5 cm layer of solution. The titration solution consisted of 0.37 µM of sRPE65 in 100 mM phosphate buffered saline (150 mM) pH 7.4 and 1% CHAPS. In FIGS. 9A1-2 and B1-2 are shown data for the binding of all-trans-retinol (tROL) and all-trans-retinyl palmitate to purified sRPE65. FIG. 9A1 shows the emission spectra of sRPE65 with increasing concentrations of tROL. FIG. 9A2 shows the linear squarefit plots for the titration of sRPE65 vs. tROL. As shown in FIGS. 9A1-2, the binding of all-trans-retinol to sRPE65 led to an exponential decay in protein fluorescence which followed a saturable binding isotherm and yielded an average $K_D$ (FIG. 9D) for binding of approximately 65 nM (FIG. 9A2). In FIG. 9B are shown data for the binding of all-trans-retinyl palmitate (tRP) to sRPE65 with a similar exponential decay in protein fluorescence. FIG. 9B1 shows the emission spectra of sRPE65 with increasing concentrations of tRP. FIG. 9B2 shows the linear squarefit plots for the titration of sRPE65 vs. tRP. This decay followed a saturable binding isotherm, and yielded an average $K_D$ (FIG. 9D) for binding of approximately 1.2 µM (FIG. 9B2). The Binding Constants of tROL and rRP with mRPE65 and sRPE65 with 1% CHAPS in 100 mM phosphate buffer with 150 mM sodium chloridebinding data are compiled in FIG. 9D.

E. sRPE65 as a Vitamin A Chaperone in the Formation of all-trans-retinyl esters.

Vitamin A bound to sRPE65 is shown to be metabolically active by demonstrating its ability to be processed by LRAT, an enzyme which represents the only known metabolic route for vitamin A processing in the RPE. As shown in FIG. 9C, vitamin A bound to sRPE65 is an excellent substrate for truncated LRAT (tLRAT), a readily expressed form of LRAT, which is mechanistically indistinguishable from LRAT. These studies demonstrate that sRPE65 can indeed direct vitamin A to LRAT, and thus the binding of vitamin A to sRPE65 may have functional significance. In the absence of sRPE65 very little synthesis of all-trans-retinyl palmitate occurs (FIG. 9C). As reported in FIG. 9C, tRP was produced in the presence of (1) sRPE65 (0.04 µM), dodecyl maltoside (0.1%) and DPPC (200 µM), but not (2) dodecyl maltoside (0.1%) and DPPC (200 µM) or (3) sRPE65 (0.04 µM) alone. All reaction mixtures contain 100 mM Tris pH 8.4, 1 mM dithiothreitol, 1 mM EDTA, 5 µM tLRAT and 0.2 µM tROL.

F. Palmitoylation of sRPE65

The biochemical relationship between mRPE65 and sRPE65 was studied with respect to their hydrophobic post-translational modification states. S-palmitoylation seemed the most likely possibility given that the process is reversible. This can be directly tested in a standard way by growing insect cells (sf21) transfected with rHRPE65 baculovirus (Ma, J., Zhang, J., Othersen, K. L., Moiseyev, G., Ablonczy, Z., Redmond, T. M., Chen, Y., Crouch, R. K. (2001) Expression, purification, and MALDI analysis of RPE65. Invest Ophthalmol Vis Sci. 42, 1429-35) in $^3H_2$-palmitic acid and determining whether the expressed mRPE65 is labeled. FIG. 10A shows the in vivo palmitoylation of rHmRPE65, expressed in sf21 cells in the presence of $^3H_2$ palmitic acid and separately in the presence of unlabeled palmitic acid. L1-4 shows the Coomassie stained gel, L5-6 shows the autoradiogram of L1-4 and L8 shows the Western blot of rHm-RPE65. In panel A, (L1) shows the $^{14}C$ molecular weight markers; (L2) shows the control with purified rHmRPE65 expressed in sf21 cells grown in the presence of unlabeled palmitic acid (0.09 µM); (L3) shows where purified rHm-RPE65 expressed in sf21 cells in the presence of $^3H_2$ palmitic acid (0.09 µM-0.5 mCi/mL) and treated for 16 hrs with 0.5 M Tris pH 8.0; (L4) shows purified rHmRPE65 expressed in sf21cells in the presence of $^3H_2$ palmitic acid (0.09 µM-0.5 mCi/mL) and then treated for 16 h with 0.5 M hydroxyl amine pH 8.0; (L5, L6 and L7) show the autoradiograms of L2, L3 and L4. L7 shows the Western blot for purified rHmRPE65 detected with anti-RPE65 primary antibody (1:4000—1 hrs room temperature).

As shown in FIG. 10A, purified mRPE65, expressed in insect cells, is indeed labeled by added $^3H$-palmitic acid. As expected, treatment of the labeled mRPE65 with hydroxylamine, which cleaves thioesters, releases the label. In order to define the sites of in vivo modification of mRPE65, mass spectroscopic experiments were performed on purified bovine mRPE65 and sRPE65. These samples were digested with trypsin and subjected to mass spectroscopic analysis (FIGS. 10B and C). The results show that mRPE65 is triply palmitoylated at positions C231, C329, and C330. By comparison, the data also show that sRPE65 appears not to be palmitoylated.

FIGS. 10B and C show the mass spectrometry analysis of two different peptides from mRPE65 and sRPE65. Trypsin digested RPE65 peptides were analyzed by MALDI-TOF. Peak annotations are as follows: FIG. 10B, 1378.9 Da (amino acid sequence 223-234, SEIVVQFPCSDR), 1429.4 Da (1-14, N-Acetyl-SSQVEHPAGGYKK), 1477.4 Da (34-44, IPLWLTGSLLR), 1483.0 Da (114-124, NIFSRFFSYFR), 1616.6 Da (223-234, SEIVVQFPC*SDR), 1700.1 Da (83-96, FIRTDAYVRAMTEK), 1701.7 (367-381, RYVLPLNID), 1718.7 (83-96, FIRTDAYVRAM#TEK). FIG. 10C, 2770.3 (333-354, GFEFVYNYSYLANLRENWEEVK), 3321.6 (306-332, TSPFNLFHHINTYEDHEFLIVDLCCWK), 3797.8 (306-332, TSPFNLFHHINTYEDHEFLIVDLC*C*WK). C* denotes palmitoylated cysteine and M# for oxidized methionine.

G. The Interconversion of mRPE65 and sRPE65 by LRAT

Since mRPE65 and sRPE65 exhibit complementary retinoid binding specificities, it is essential to understand how these two molecules are inter-converted. Most interestingly, LRAT is able to utilize mRPE65 as a palmitoyl donor (FIG. 11A) and transfers this moiety to vitamin A to generate all-trans-retinyl palmate (FIGS. 11B, C, D). FIG. 11B shows the mRPE65 alone (-■-) and DPPC alone (-●-) dependent esterification of all-trans-retinol. In these experiments, pure mRPE65 and vitamin A are incubated with LRAT and the resultant all-trans-retinyl palmitate is isolated by HPLC. Mass spectroscopic analysis of the isolated all-trans-retinyl palmitate show it to be authentic and hence a palmitoyl moiety was transferred from mRPE65 to vitamin A. These data also reveal that mRPE65 is a much more efficient palmitoyl donor than dipalamitoyl phosphatidylcholine (DPPC), the standard acyl donor in the LRAT reaction. Under the same conditions, no observable turnover of DPPC is measured (FIG. 11B). The kinetic plot shown in FIG. 11B reveals sigmoidal kinetics with a calculated $K_M$ ($K_{app}$) of 0.03 µM for mRPE65 (compared to a value of 1.4 µM for DPPC). The Hill plot (FIG. 11C) yields a value of 2.54 for N, suggesting that more than one molecule of mRPE65 is involved in the transfer of the palmitoyl group. The observed sigmoidal kinetics suggests a regulatory role for this process, allowing it to respond to slight changes in mRPE65 concentrations.

Reversibility in the reaction is readily established. In these experiments (FIG. 11D) excess all-trans-retinol is incubated with mRPE65 and tLRAT until no further all-trans-retinyl palmitate is generated. This is followed by treatment with $^3$H-trans-retinol. The subsequent rise of the specific activities of all-trans-retinyl palmitate and the fall in specific activities of all-trans-retinol at constant all-trans-retinyl palmitate levels reveals the equilibration of substrates (FIG. 11D). FIG. 11D shows the change in specific activities (left y-axis) of tRP (-■-) and tROL (-●-) as a function of time. The total retinyl ester (-▲-) formed (right y-axis) shows the saturation of the ester synthesizing reaction. Each reaction contains 100 mM Tris pH 8.4, 0.06 µM mRPE65, 5 µM tLRAT, 1 mM dithiothreitol, 1 mM EDTA and 10 µM tROL.

The depalmitoylated RPE65 formed when mRPE65 is treated with tLRAT and vitamin A shows retinoid binding behavior similar to sRPE65. mRPE65 was incubated with excess vitamin A and tLRAT. After the removal of the retinoids and tLRAT, the sRPE65 was then studied with respect to its ability to bind vitamin A and all-trans-retinyl palmitate. As shown in FIG. 2D, the treatment of mRPE65 with LRAT and vitamin A, converts mRPE65 to a functional binding form of RPE65 indistinguishable from that of isolated sRPE65.

H. 11-cis-retinol is Palmitoylated by mRPE65 and LRAT 11-cis-retinol, the direct product of IMH action, is also esterified (FIG. 12A). As FIG. 12B shows, 11-cis-retinol is actually a superior substrate during the tLRAT/mRPE65 mediated esterification (palmitoylation) of the retinoids compared to vitamin A. (1) 11-cis-retinol (2 µM) and mRPE65 (0.02 µM). (2) all-trans-retinol (2 µM) and mRPE65 (0.02 µM). (3) 11-cis-retinol (2 µM) and DPPC/BSA (250 µM/0.4%). (4) all-trans-retinol (2 µM) and DPPC/BSA (250 µM/0.4%). All reaction mixtures contain 100 mM Tris pH 8.4, 1 mM dithiothreitol, 1 mM EDTA and 5 µM tLRAT.

The palmitoylation of 11-cis-retinol by mRPE65 provides a natural mechanism through which mRPE65 is turned over and control is exerted during the operation of the visual cycle because 11-cis-retinol drives mRPE65 to sRPE65, effectively shutting down the pathway to chromophore biosynthesis. This is directly demonstrated in FIG. 12C in which RPE membranes are treated with 10 µM 11-cis-retinol to drive the mRPE65 to sRPE65 transition. This figure shows the time dependent generation of [11-12-$^3$H$_2$] 11-cis-retinol in the presence of 11-cis-retinol mediated depalmitoylation (-●-) and in the absence of 11-cis-retinol mediated depalmitoylation (-■-). The inset shows the full time interval. Irradiation of the sample with ultraviolet light destroys the 11-cis-retinoids. Control and treated samples are then incubated with vitamin A, and the rates of 11-cis-retinol, the product of IMH, are measured. The sample pretreated with 11-cis-retinol shows a distinct lag period before product synthesis occurs.

Exemplary RPE65 Antagonists

The constants of affinity ($K_d$s) of several compounds for bovine RPE65 were determined. It was found that the compounds described above as 4a, 4b and 4c have a Kd of 47 nM, 235 nM and 1300 nM, respectively. Thus, the potency of binding is a function of the ester chain length, i.e., the longer the chain length, the stronger the affinity for RPE65 is and the stronger the antagonist is.

Compounds listed above as 4d, 4e and 4f are also potent RPE65 antagonists, having a $K_d$ of 21 nM, 40 nM and 64 nM, respectively.

REFERENCES CITED

Anantharaman, V., Aravind, L. (2003). Evolutionary history, structural features and biochemical diversity of the NIpC/P60 superfamily of enzymes. Gen. Biol. 4, R11.

Arshavsky, V. Y., Lamb, T. D., and Pugh E N Jr. (2002) G proteins and phototransduction. Annu. Rev. Physiol. 64, 153-187.

Barry, R. J., Cañada, F. J., and Rando, R. R. (1989) Solubilization and partial purification of retinyl ester synthetase and retinoid isomerase from bovine ocular pigment epithelium. J. Biol. Chem. 264, 9231-9238.

Bavik, C. O., Levy, F., Hellman, U., Wernstedt, C., and Eriksson, U. (1993). The retinal pigment epithelial membrane receptor for plasma retinol-binding protein. Isolation and cDNA cloning of the 63-kDa protein. J. Biol. Chem. 268, 20540-20546.

Bernstein, P. S., Law, W. C., and Rando, R. R. (1987). Isomerization of all-trans-retinoids to 11-cis-retinoids in vitro. Proc. Natl. Acad. Sci. (USA) 84, 1849-1853.

Bijlmakers, M. J., Marsh, M., (2003). The on-off story of protein palmitoylation. Trends. Cell. Biol. 13, 32-42.

Bok, D. (1993). The retinal pigment epithelium: a versatile partner in vision. J. Cell. Sci. Suppl. 17, 189-195.

Bok, D., Ruiz, A., Yaron, O., Jahng, W. J., Ray, A., Xue, L., Rando, R. R. (2003). Purification and characterization of a transmembrane domain-deleted form of lecithin retinol acyltransferase. Biochemistry 42, 6090-8.

Bridges, C. D. B. (1976) Vitamin A and the role of the pigment epithelium during bleaching and regeneration of rhodopsin in the frog eye. Exp. Eye. Res. 22, 435-455.

Cañada, F. J., Law, W. C. and Rando, R. R. (1990). Substrate specificities and mechanism in the enzymatic processing of vitamin A into 11-cis-retinol. Biochemistry 29, 9690-9697.

Chen, C. A. and Manning D. R. (2001). Regulation of G proteins by covalent modification. Oncogene 20, 1643-1652.

Deigner, P. S., Law, W. C., Cañada, F. J., and Rando, R. R. (1989). Membranes as the energy source in the endergonic transformation of vitamin A to 11-cis-retinol. Science 244, 968-971.

Dunphy, J. T. and Linder, M. E. (1998). Signaling functions of protein palmitoylation. Biochim Biophys Acta. 1436, 245-261.

El-Husseini, A. E. and Bredt D. S. (2002) Protein Palmitoylation: A regulator of neuronal developmental and function. Nat. Rev. 3, 791-802.

Gollapalli, D. R., Rando R. R. (2003). All-trans-Retinyl Esters are the Substrates for Isomerization in the Vertebrate Visual Cycle. Biochemistry 42, 5809-18.

Gollapalli, D. R., Maiti, P., Rando, R. R. (2003) RPE65 operates in the vertebrate visual cycle by stereospecifically binding all-trans-retinyl esters. Biochemistry 42, 11824-30.

Gonzalez-Fernandez, F. (2002). Evolution of the visual cycle: the role of retinoid-binding proteins. J. Endocrinol. 175, 75-88.

Hamel, C. P., Tsilou, E., Pfeffer, B. A., Hooks, J. J., Detrick, B., and Redmond, T. M. (1993). Molecular cloning and expression of RPE65, a novel retinal pigment epithelium-specific microsomal protein that is post-transcriptionally regulated in vitro. J. Biol. Chem. 268, 15751-15757.

Hanna-Rose, W. and Han, M. (2002) The Caenorhabditis elegans EGL-26 protein mediates vulval cell morphogenesis. Dev. Biol. 241, 247-258.

Houslay, M. D, (1996) Regulation of cellular signaling by fatty acid acylation and prenylation of signal transduction proteins. Cell. Signal. 8, 403-412.

Jahng, W. J., David, C., Nesnas, N., Nakanishi, K., and Rando, R. R. (2003). A cleavable affinity biotinylating agent reveals a retinoid binding role for RPE65. Biochemistry 42, 6159-6168.

Jahng, W. J., Xue, L., Rando, R. R. (2003). Lecithin retinol acyltransferase is a founder member of a novel family of enzymes. Biochemistry 42, 12805-12.

Kammer, B., Schmidt, M. F. G., Veit, M. (2003) Functional characterization of palmitoylation and nonacylated SNAP-25 purified from insect cells infected with recombinant baculovirus. Mol. Cell. Neuroscience. 23, 333-340.

Linder, M. E. and Deschenes, R. J. (2003). New insights into the mechanisms of protein palmitoylation. Biochemistry 42, 4311-4320.

Lowry, O. H., Rosebrough, N. J., Farr, A. L. and Randall, R. J. (1951). Protein measurement with the Folin phenol reagent. J. Biol. Chem. 193, 265-275.

Ma, J., Zhang, J., Othersen, K. L., Moiseyev, G., Ablonczy, Z., Redmond, T. M., Chen, Y., Crouch, R. K. (2001) Expression, purification, and MALDI analysis of RPE65. Invest Ophthalmol Vis Sci. 42, 1429-35.

Mata, N. L., Moghrabi, W. N., Lee, J. S., Bui, T. V., Radu, R. A., Horwitz, J., Travis, G. H. (2004). Rpe65 is a retinyl-ester binding protein that presents insoluble substrate to the isomerase in retinal pigment epithelial cells. J Biol. Chem. 279, 635-43.

Milligan, G. Parenti, M. and Magee, A. I. (1995). The Dynamic role of palmitoylation in signal transduction. Trends Biochem. Sci. 20, 181-187.

Morello J P, Bouvier M. (1996). Palmitoylation: a post-translational modification that regulates signaling from G-protein coupled receptors. Biochem. Cell Biol. 74, 449-457.

Mumby, S. M., (1997). Reversible palmitoylation of signaling proteins. Curr. Opin. Cell Biol. 9, 148-154.

Patterson, P. L. (2002). Posttranslational protein S-palmitoylation and the compartmentalization of signaling molecules in neurons. Biol Res. 35, 139-50.

Qanbar, R, Bouvier, M. (2003). Role of palmitoylation/depalmitoylation reactions in G-protein-coupled receptor function. Pharmacol. Ther. 97, 1-33.

Rando, R. R. and Bangerter, F. W. (1982) The rapid intermembraneous transfer of retinoids. Biochem. Biophys. Res. Commun. 104, 430-436.

Rando, R. R. (1990) The chemistry of vitamin A and the visual process. Angew. Chemie (Int. Ed. Engl.) 29, 461-480.

Rando, R. R. (1991) Membrane phospholipids as an energy source in the operation of the visual cycle. Biochemistry 30, 595-602.

Rando, R. R. (2001) *The biochemistry of the visual cycle.* Chem. Rev. 101, 1881-1896.

Redmond, T. M., Yu, S., Lee, E., Bok, D., Hamasaki, D., Chen, N., Goletz, P., Ma, J. X., Crouch, R. K., and Pfeifer, K. (1998) Nat. Genet. 20, 344-351.

Resh, M. D. (1999). Fatty acylation of proteins: new insights into membrane targeting of myristoylated and palmitoylated proteins. Biochim. Biophys. Acta. 1451, 1-16.

Saari, J. C. (2000). Biochemistry of visual pigment regeneration: the Friedenwald lecture. Invest. Ophth. Vis. Sci. 41, 337-348.

Saari, J. C., Bredberg, L., and Farrell, D. F. (1993) Retinol esterification in bovine retinal pigment epithelium: reversibility of lecithin: retinol acyltransferase. Biochem. J. 291, 697-700.

Segal, I. H. (1993). Enzyme Kinetics. (New York; Wiley-Interscience).

Shi, Y.-Q., Furuyoshi, S., Hubacek, T., and Rando, R. R. (1993). Affinity labeling of lecithin retinol acyltransferase. Biochemistry 32, 3077-3080.

Stacie, R. L., Yuechueng L. (1997). Characterization of the Palmitoylation Domain of SNAP-25. J. Neurochem. 69, 1864-1869.

Stryer L. (1986) Cyclic GMP cascade of vision. Annu. Rev. Neurosci. 9, 87-119.

Thompson, D. A. and Gal A. (2003). Genetic defects in vitamin A metabolism of the retinal pigment epithelium. Dev. Ophthalmol. 37, 141-54.

Trehan, A., Cañada, F. J. and Rando, R. R. (1990). Inhibitors of retinyl ester formation also prevent the biosynthesis of 11-cis-retinol. Biochemistry 29, 309-312, von Lintig, J., Vogt, K. (2000). Filling the gap in vitamin A research. Molecular identification of an enzyme cleaving beta-carotene to retinal. J. Biol. Chem. 275, 11915-11920.

Wald, G. The biochemistry of vision (1953) Annu. Rev. Biochem. 22, 497-526.

West, K. A., Yan, L., Shadrach, K., Sun, J., Hasan, A., Miyagi, M., Crabb, J. S., Hollyfield, J. G., Marmorstein, A. D., Crabb, J. W. (2003). Protein database, human retinal pigment epithelium. Mol. Cell. Proteomics. 2, 37-49.

Winston, A. and Rando, R. R. (1998). Regulation of Isomerohydrolase Activity in the Visual Cycle. Biochemistry 37, 2044-2050.

Wolf, G. (1996). The regulation of retinoic acid formation. Nutr. Rev. 54, 182-184.

Example 2

Effect on Visual Cycle of Short-Circuiting Drugs in vivo

Mice were injected intraperitoneally (i.p.) with 50 mg/kg of the compounds listed prepared in 25 microliters DMSO. Positive control mice were injected with 13-cis-retinoic acid (ACCUTANE®) 50 mg/kg in 25 microliters DMSO. Negative control mice were injected with 25 microliters DMSO.

At predetermined times after administration, mice were exposed to sufficient light to cause complete bleaching of the visual cycle. Electroretinograms (ERG) were then performed in bright light or dim light, and the b-wave amplitude measured. The b-wave amplitude is assumed to be proportional to rhodopsin regeneration and thereby correlate with the functioning of the visual cycle (i.e., the higher the b-wave amplitude, the greater the functioning of the visual cycle).

A. 4-butyl-aniline and ethyl 3-aminobenzoate 4-butyl-aniline and ethyl 3-aminobenzoate, were prepared as solutions in DMSO. 7 months old wild type (wt; C57BL/6J×129/SV; Rpe65 Leu450Leu) mice were injected i.p. with 25 microliters (50 mg/kg) of each compound. Animals injected with ACCUTANE (13-cis-retinoic acid, 25 microliters, 50 mg/kg) and DMSO (labeled as wt; 25 microliters) were used as positive and negative controls, respectively. Two mice were injected in each group. ERG measurements were performed.

Figure 14A:
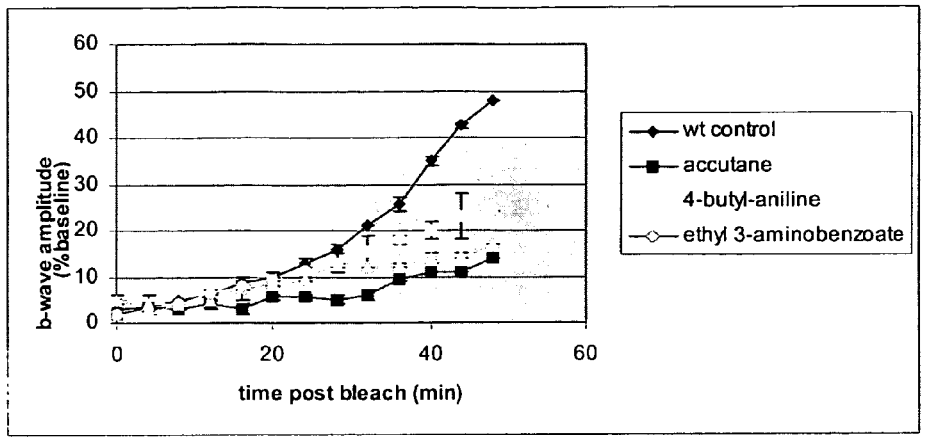
FIGS. 14A-18B present data regarding in vivo effects of short circuit drugs.

FIG. 14A shows effects of the compounds 1 hour after injection. The wild-type negative control showed a recovery to 50% of baseline b-wave amplitude (considered complete recovery), while the positive control and test compounds showed greater impairment of the visual cycle.

Figure 14B:
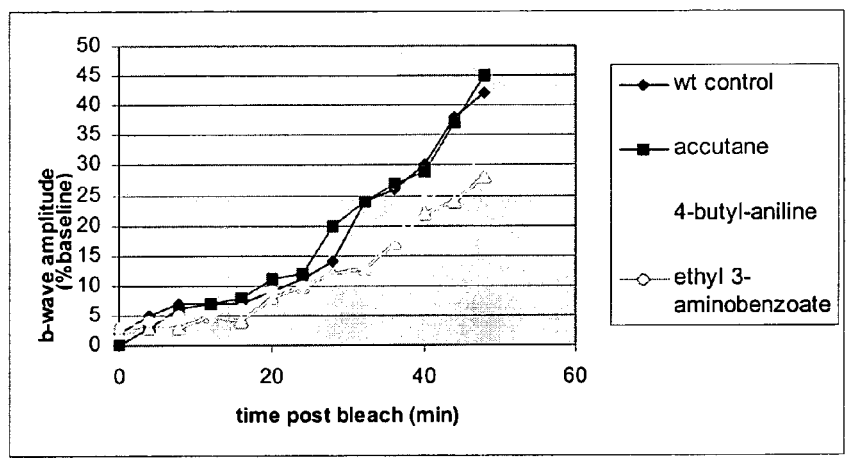

FIG. 14B shows effects of the compounds 1 week (7 days) after injection. The test compounds had a sustained effect, while the positive control returned to complete recovery.

Figure 14C:
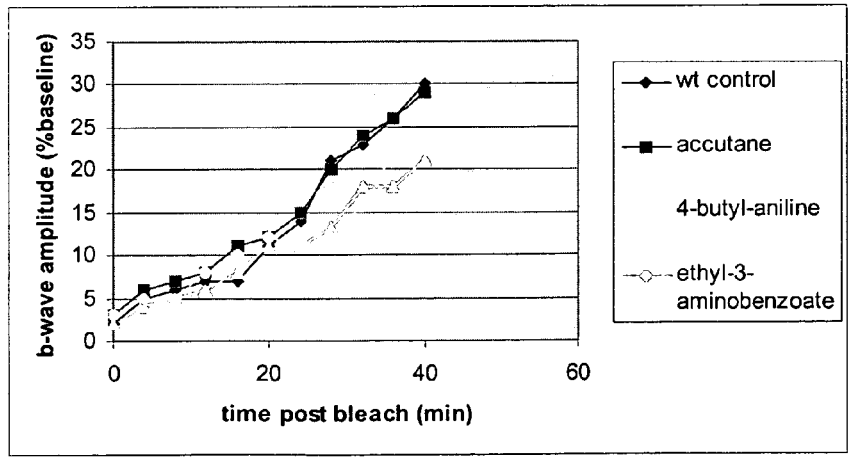
Figure 15A:
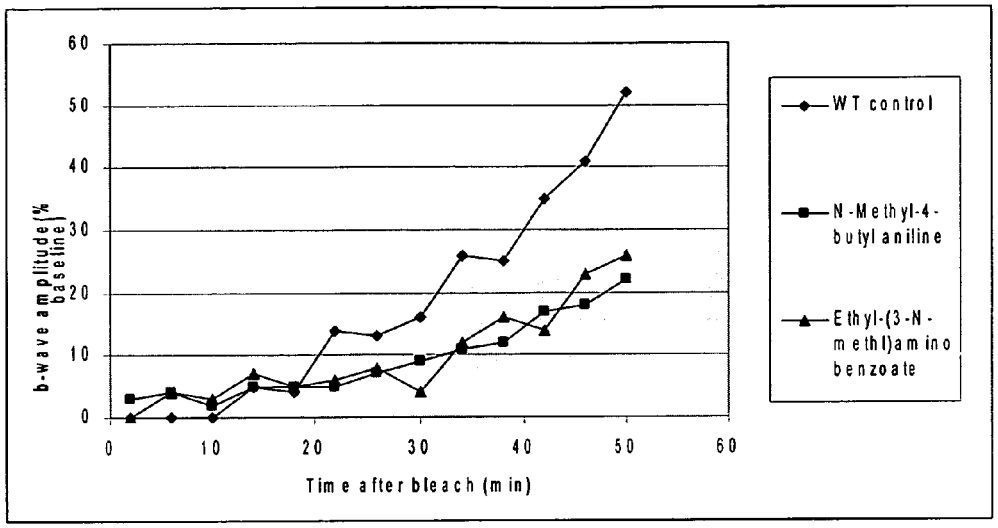
Figure 15B:
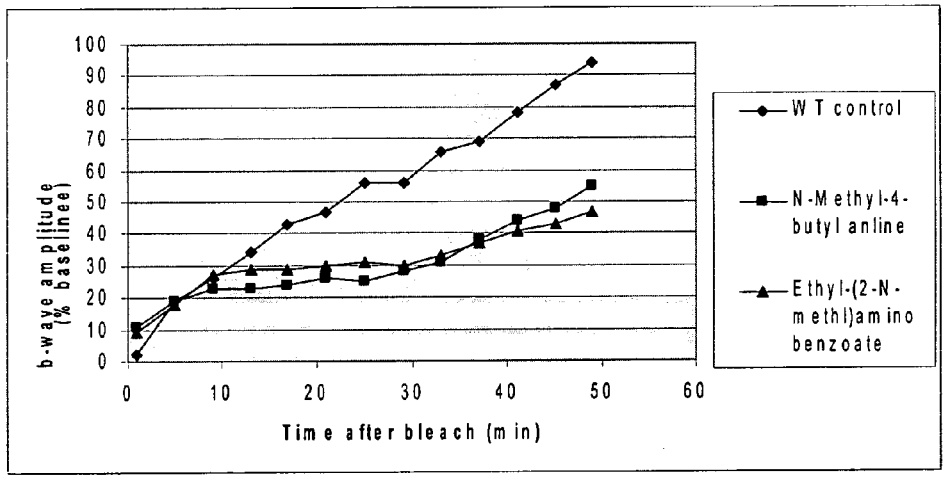
Figure 16A:
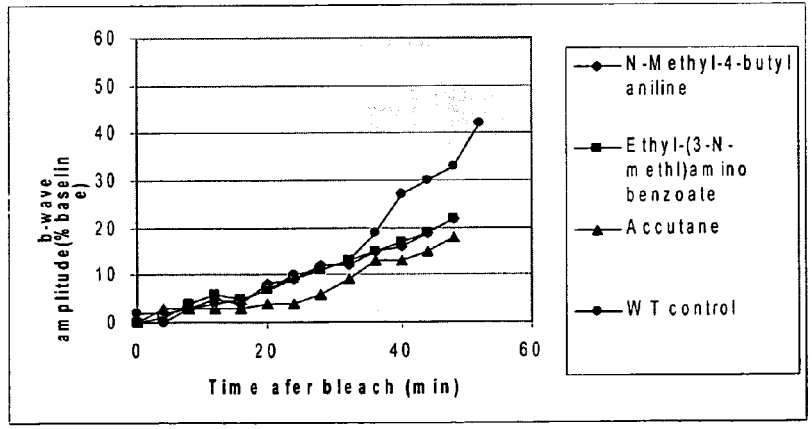
Figure 16B:
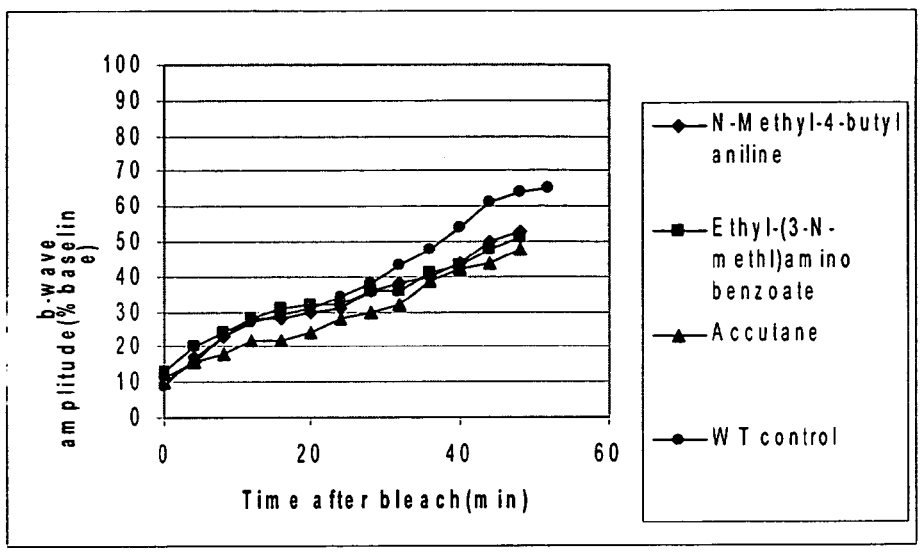
Figure 17A:
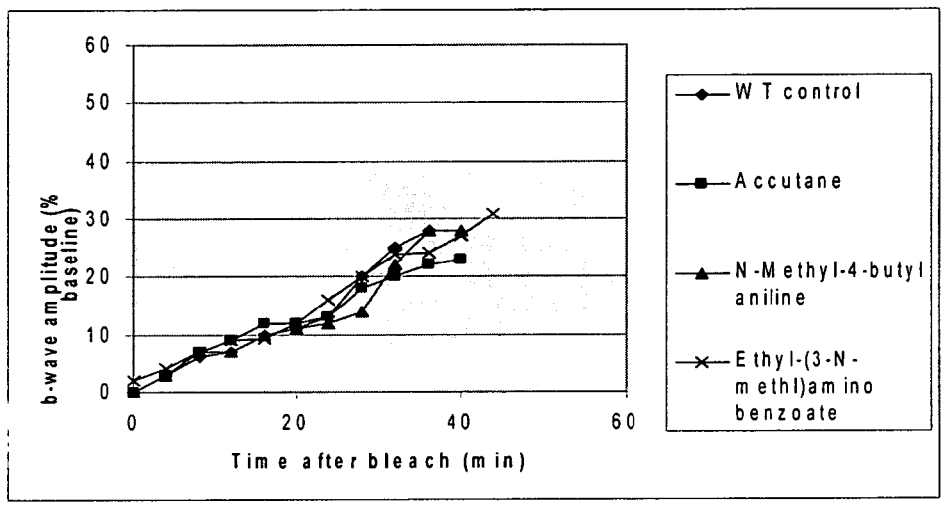
Figure 17B:
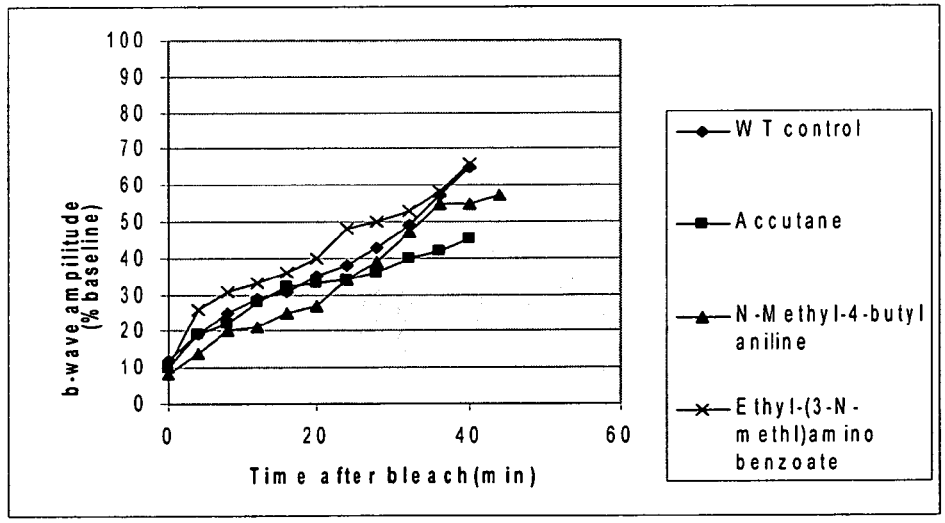

FIG. 14C shows effects 2 weeks (14) days after injection. The test compounds still had effect on the visual cycle.

B. Ethyl-(3-N-methl)amino benzoate, N-Methyl-4-butyl aniline

FIGS. 15A-B, 16A-B, and 17A-B show, respectively, three experiments with these compounds in dim (A) and bright (B) light.

C. Ethyl-(2-N-methl)amino benzoate, N-Methyl-4-butyl aniline

Figure 18A:
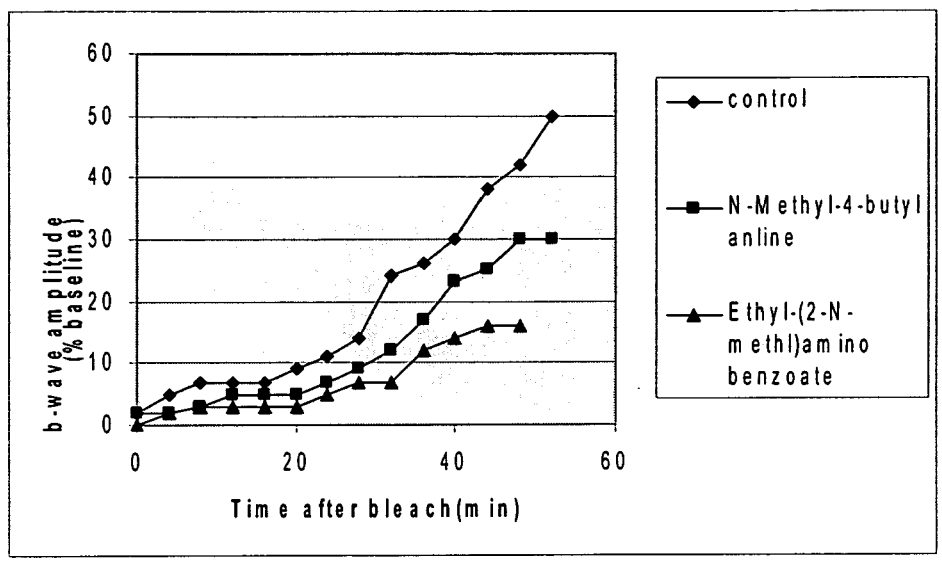
Figure 18B:
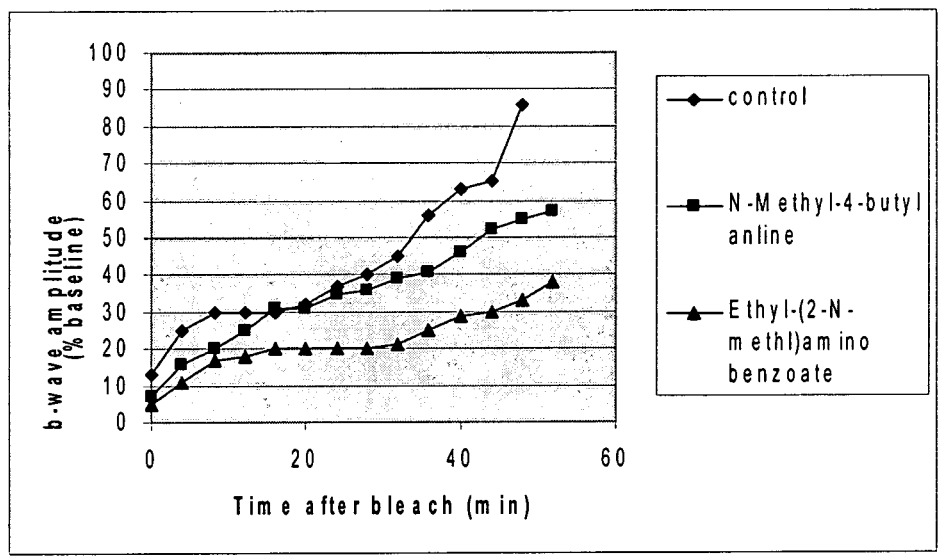

FIGS. 18A-B show experiments with these compounds in dim (A) and bright (B) light.

Example 3

Effect on Visual Cycle of Enzyme Inhibitors and RPE65 Antagonists in vivo

The experiments described in Example 2 were repeated additional compounds.

A. Retinyl palmityl ketone and retinyl decyl ketone

Figure 19:
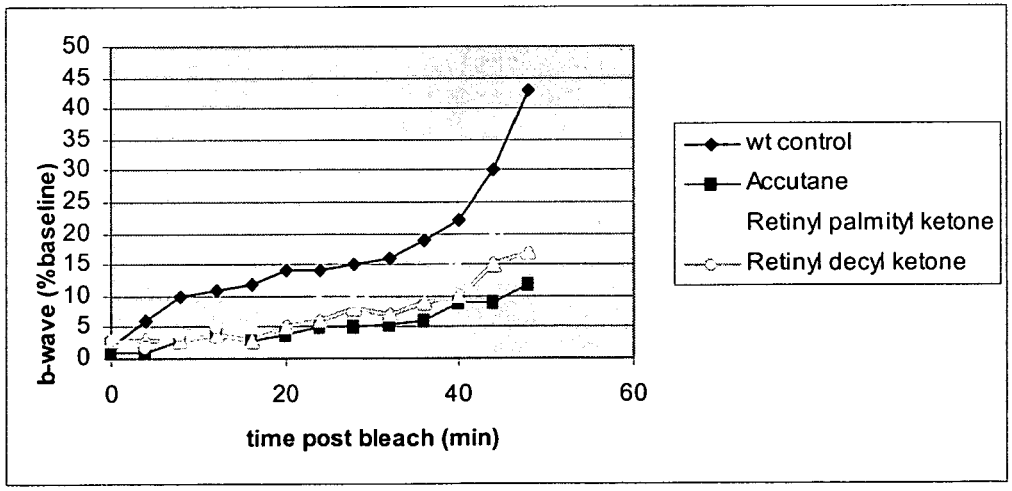
FIGS. 19-24 present data regarding in vivo effects of enzyme inhibitors and/or RPE65 antagonists.
Figure 20A:
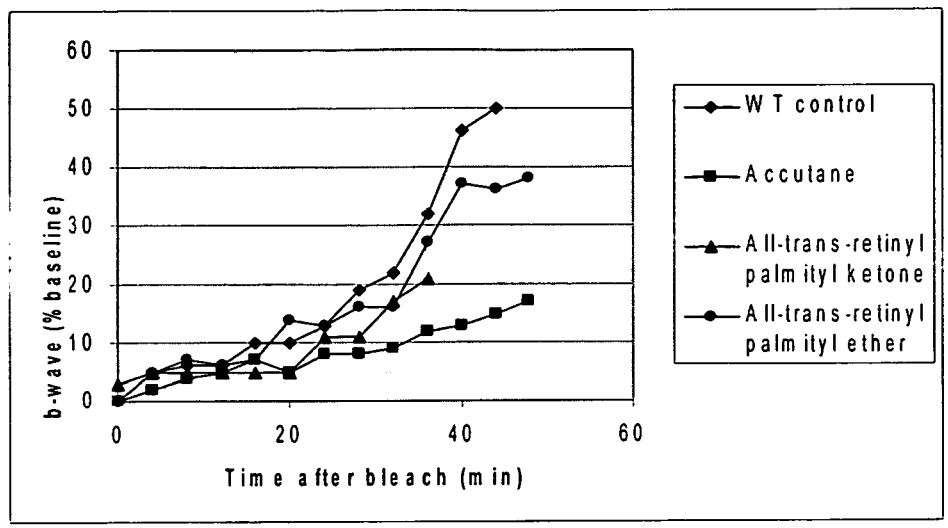
Figure 20B:
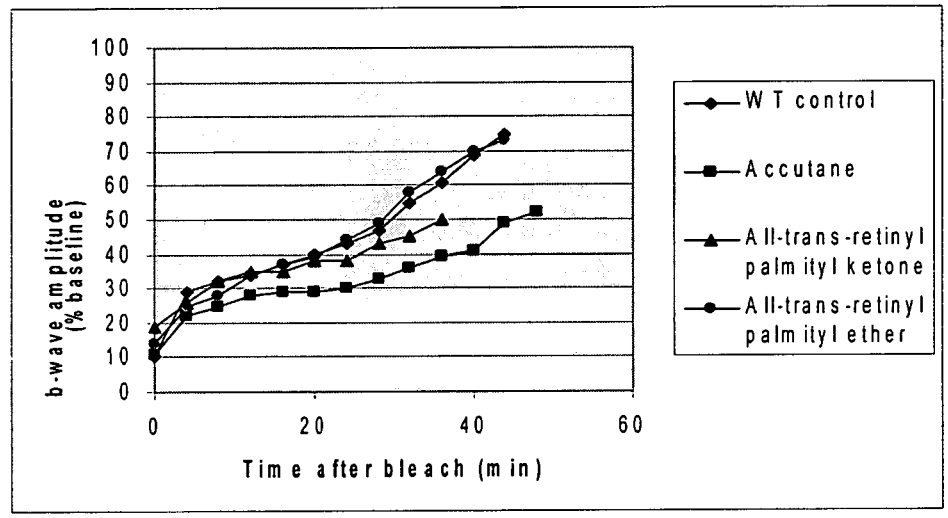
Figure 21A:
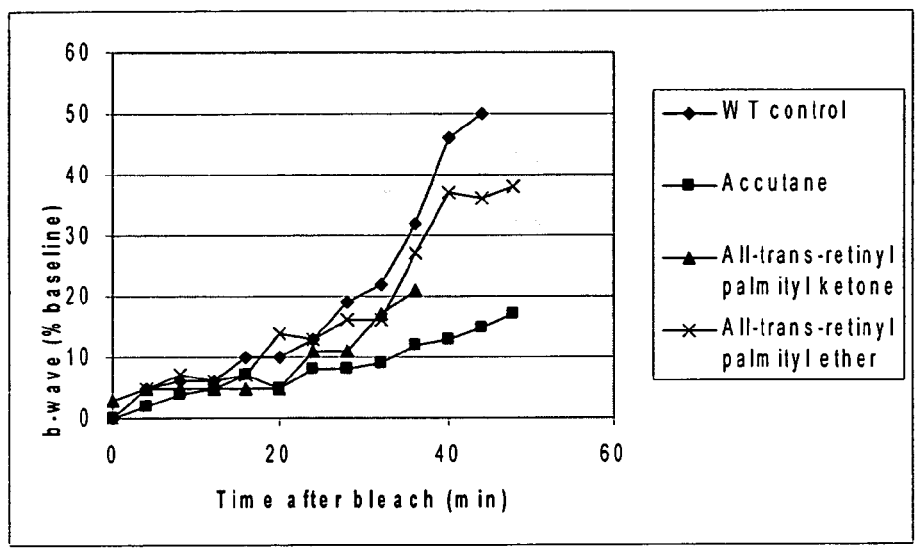
Figure 21B:
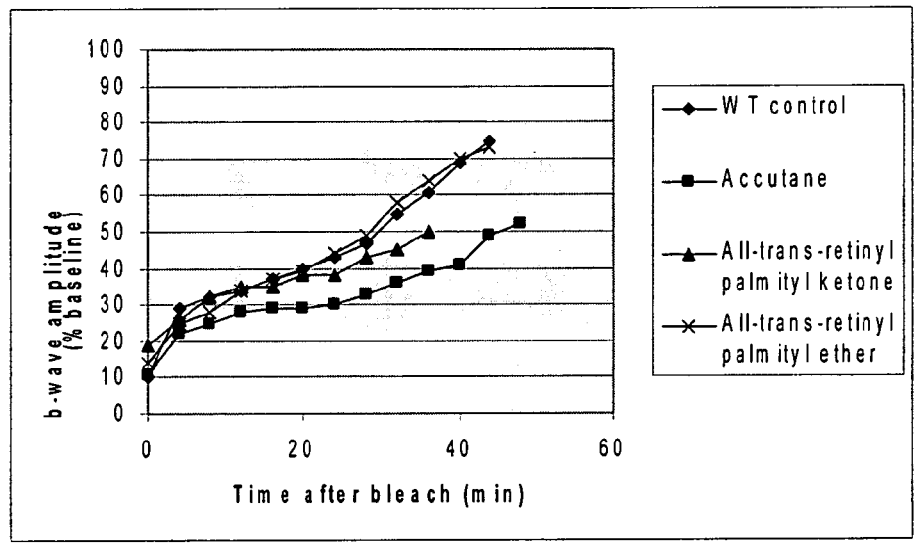

FIG. 19 shows an experiment with these compounds.

B. All-trans-retinyl palmityl ketone, all-trans-retinyl palmityl ether

FIGS. 20A-B and 21A-B show, respectively, two experiments with these compounds in dim (A) and bright (B) light.

C. Octyl farnestimide, palmityl farnestimide

Figure 22A:
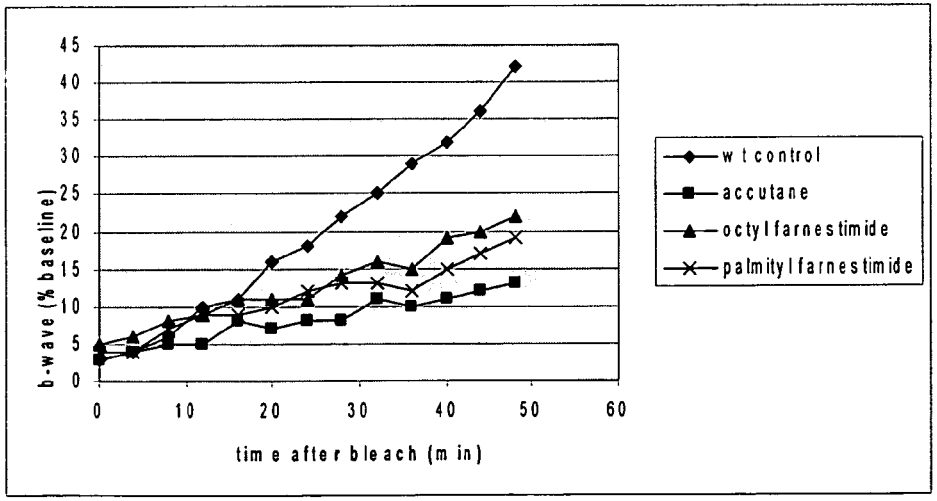
Figure 22B:
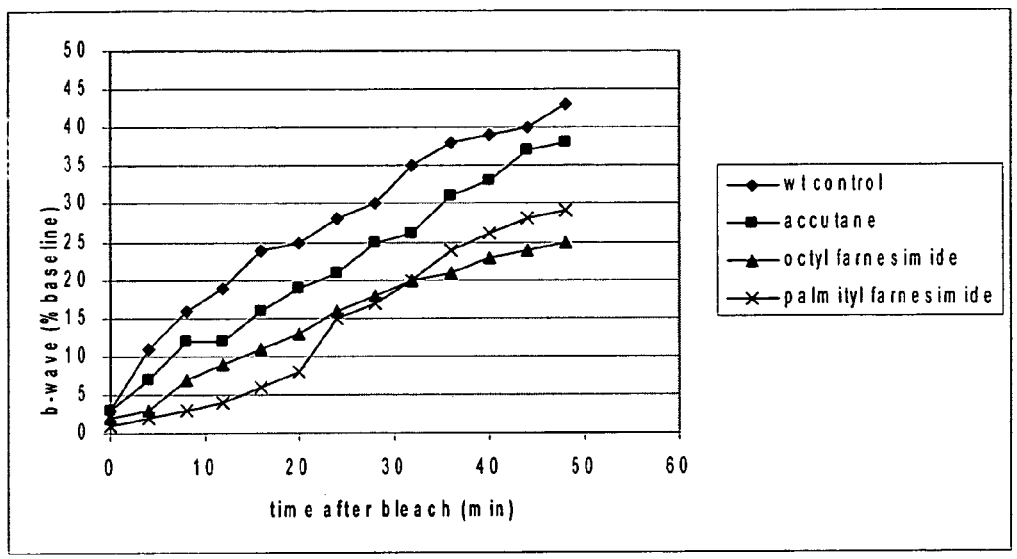

FIG. 22A shows the results of an experiment in dim light using these compounds shortly after administration. FIG. 22B shows the results one week after administration.

D. Farnsyl octyl ketone, farnesyl decyl ketone

Figure 23A:
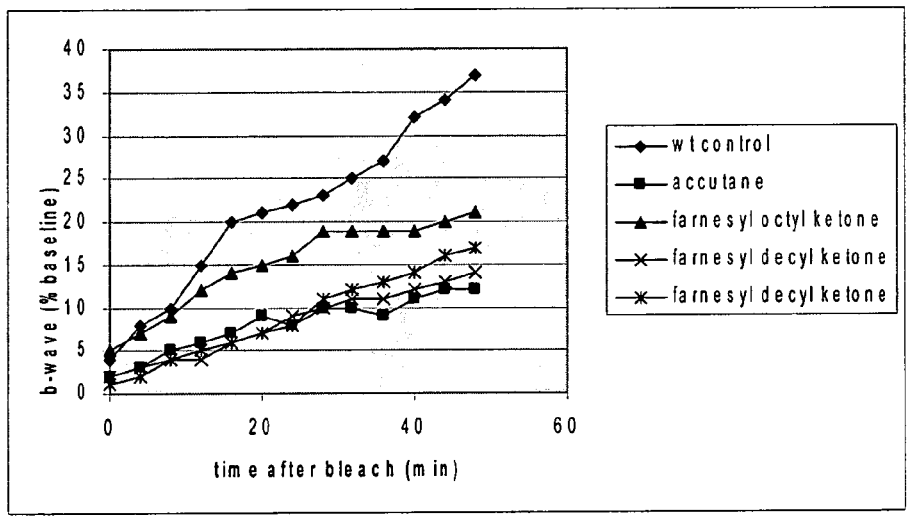
Figure 23B:
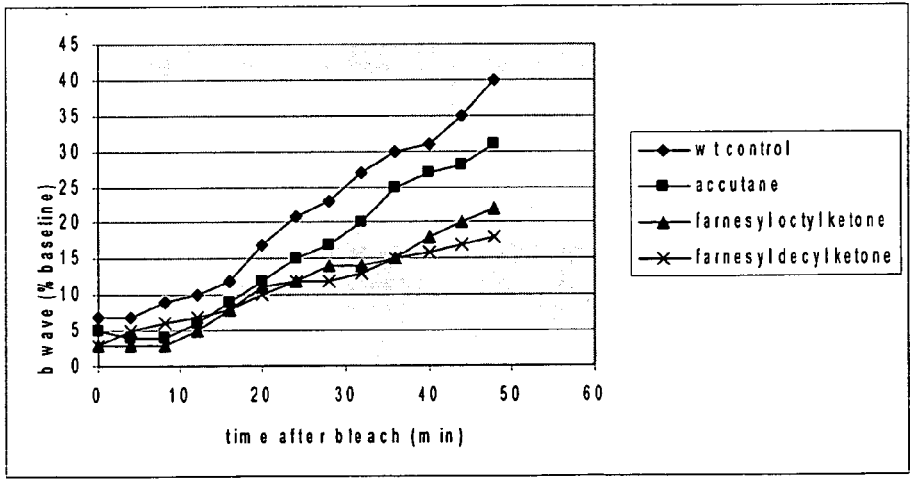
Figure 23C:
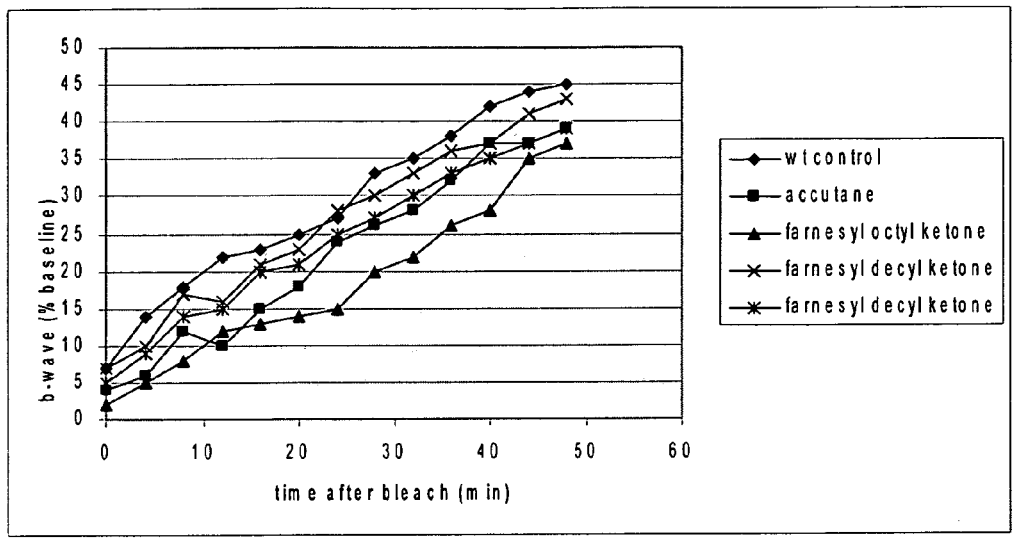

FIGS. 23A-C show experiments performed in dim light using these compounds. The data shown in FIG. 23B was obtained 3 days after administration. The data in FIG. 23C was obtained 8 days after administration.

E. Farnesyl palmityl ketone, farnesyl decyl ketone

Figure 24:
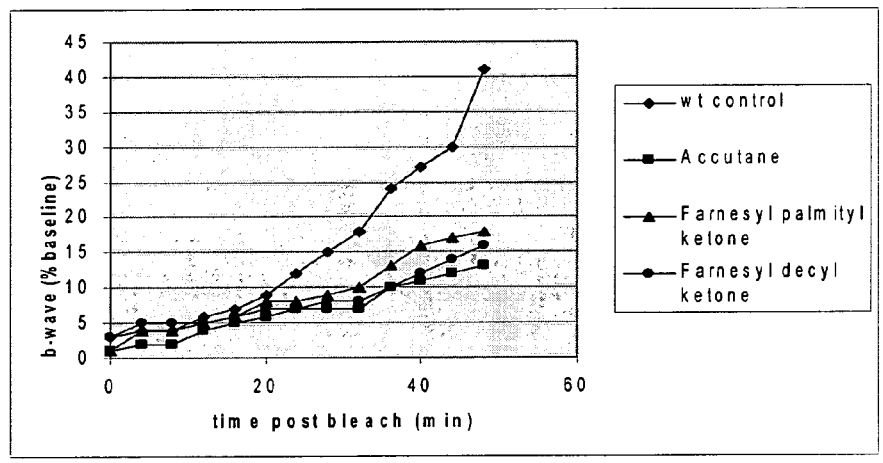

FIG. 24 shows the results of an experiment performed in dim light 1 hour after these compounds were injected.

Example 4

$A_2E$ Formation in the Presence of Aromatic Amine 100 mg (355 µmoles) of all-trans-retinal was dissolved in 3 mL followed by the addition of 9.5 µL of glacial acetic acid 9.5 µL of ethanolamine (155 µmoles). This solution was aliquoted into 300 µL fractions. 3-aminoethylbenzoate (15.5 µmoles) was added to the samples at 0, 2, 3.75, 14, 16.25, 18.0833 19.917 23.75 and 48 hrs. A control sample did not contain aromatic amine. The solutions were shaken at room temperature for 48 hrs. The solutions were then kept at −80° C. and 15 µL was diluted to 250 µL (methanol). The solutions (15 µL) were then analyzed on a reverse phase (C18-5 µm-4.6 mm×150 mm) column on a linear gradient 85%-96% methanol/water and UV detector at 430 nm to determine the amount of $A_2E$ formation. The percent $A_2E$ formation was compared to $A_2E$ formation at 48 h in the absence of aromatic amine.

TABLE 1

| $A_2E$ formation | | |
| --- | --- | --- |
| Time (Hrs) | % formation (48 Hrs = 100) | Area under the Curve |
| 0 | 3.98 | 422.5 |
| 2 | 8.67 | 920 |
| 3.75 | 7.71 | 818.5 |
| 14 | 19.73 | 2094 |
| 16.25 | 19.25 | 2043 |
| 18.0833 | 23.70 | 2515 |
| 19.91667 | 27.65 | 2934 |
| 23.75 | 22.44 | 2382 |
| 48 | 100.00 | 10613 |

Figure 25:
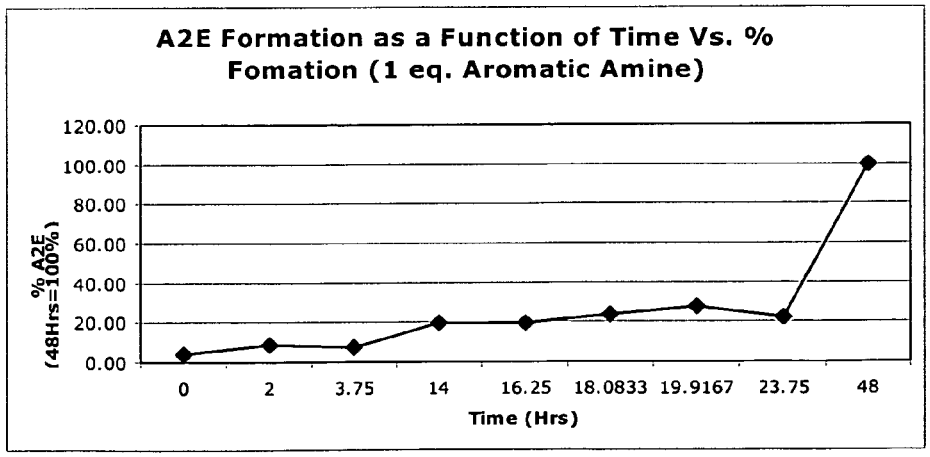
FIG. 25 presents data concerning in vitro formation of $A_2E$ in the presence of aromatic amines.

The data in Table 1 is presented in FIG. 25 and shows that aromatic amines can not form $A_2E$ in the standard in vitro reaction; furthermore, they prevent $A_2E$ from forming.

Example 5

In vivo $A_2E$ Formation

Effects on accumulation of $A_2E$ in abcr knockout mice by farnesyl decyl ketone and N-palmityl farnesimide were investigated. Mice were injected with 50 mg/kg drug in 25 microliters of DMSO or with only DMSO for the control group once or twice a week. After 2 to 2½ months, the mice were sacrificed, and $A_2E$ and iso-$A_2E$ were harvested and quantitated from 4 eyes for each drug or control. Results are shown in Table 2.

Table 2: $A_2E$ Accumulation in treated or untreated abcr mice

|  | (pmoles/eye) | | |
| --- | --- | --- | --- |
|  | A2E | iso-A2E | total |
| no drug | 11.01 | 2.57 | 13.58 |
| Farnesyl decyl ketone | 2.00 | 0.66 | 2.66 |
| N-Palmityl farnesimide | 5.38 | 1.70 | 7.09 |

These data show that farnesyl decyl ketone reduced $A_2E$ accumulation by over 80%, iso-$A_2E$ by about 74%, total by about 80%. N-palmityl farnesimide reduced $A_2E$ accumulation by over 50%, and iso-$A_2E$ by about 33%, total by about 47%.

Example 7

TDT and TDH Bind to mRPE65 with High Affinities

Materials: Frozen bovine eye-cups devoid of retinas were purchased from W. L. Lawson Co., Lincoln, Nebr. Ethylenediaminetetraacetic acid (EDTA), phenyl-Sepharose CL-4B, and Trizma® base, trans-trans-farnesol, pyridinium chlorochromate, Dess-Martin reagent, decyl magnesium bromide, hexadecyl amine, dimethylsulfoxide were from Sigma-Aldrich. Dithiothreitol (DTT) was from ICN Biomedicals Inc. Anagrade™ CHAPS was from Anatrace. HPLC grade solvents were from Sigma-Aldrich Chemicals. Anti RPE65 (NFITKVNPETLETIK) antibody was obtained from Genmed Inc. Broad spectrum EDTA-free protease inhibitor cocktail was obtained from Roche Biosciences. The precast gels (4-20%) for SDS-PAGE, BenchMark prestained molecular weight marker were from Invitrogen. DEAE Sepharose was from Amersham Biosciences. All reagents were analytical grade unless specified otherwise.

Methods

Animal Studies: Protocols were approved by the Standing Committee on Animal Care of Harvard Medical School, the Institutional Animal Care and Use Committee of Columbia University and complied with guidelines set forth by The Association for Research in Vision and Ophthalmology. 7 week old male Balb/c albino mice and 7 week old male Sprague-Dawley rats were from Charles River Breeding Laboratories and were housed in 12:12 h light:dark cycle. 8-10 week old Abcr null mutant mice (129/SV×C57BL/6J) were generated as formerly described (12,20) and Abcr$^{-/-}$ and Abcr$^{+/+}$ mice were raised under 12-hour on-off cyclic lighting with an in-cage illuminance of 30-50 lux. In Abcr$^{-/-}$ and Abcr$^{+/+}$ mice, Rpe65 was 9 sequenced as reported previously [20].

Purification of mRPE65: mRPE65 was extracted and purified from the bovine eye cups using a procedure described earlier [29]. Protein purity was established by silver staining and Western blotting (1:4000 primary antibody—1 h at room temperature and 1:4000 secondary antibody 0.5 h at room temperature). Buffers were changed by dialysis in the request buffer overnight in a slide-a-lyser™ cassette from Pierce (10 KDa MWCO). RPE65 solutions were concentrated with an Amicon Ultra™ centrifugal filtration device (30 KDa-cutoff) from Millipore Corp. The final protein solution contained 100 mM phosphate buffered saline (150 mM NaCl) pH 7.4 and 1% CHAPSO. The protein concentration was measured by a modified Lowry method [30] using the Bio-Rad $D_C$ protein assay protocol.

Syntheses:

13,17,21-Trimethyl-docosa-12,16,20-trien-11-one (TDT): A solution of trans, trans-farnesal (200 mg, 0.9 mmol) in ether (2 mL) was added to a solution of decyl magnesium bromide (1 M solution in ether, 1.5 mL) at 0° C. and stirred for 15 min. The reaction mixture was then warmed to room temperature and quenched with aqueous saturated NH$_4$Cl (1 mL). H$_2$O (2 mL) was added and the reaction mixture was extracted with hexane (3×5 mL). The combined extracts were collected, washed with brine, dried with magnesium sulfate and evaporated under reduced pressure. The residue was chromatographed (SiO$_2$, EtOAc-light petroleum, 10:90) to give the alcohol (319 mg, 92%); $R_f$(EtOAc-light petroleum, 2:8) 0.56. Dess-Martin periodinate (419 mg, 0.99 mmol) was added to a solution of the above alcohol (319 mg, 0.83 mmol) in CH$_2$Cl$_2$ (1.5 mL) at room temperature and stirred for 10 min. The reaction mixture was then treated with sodium thiosulfate-sodium bicarbonate solution (1:1 v/v of 10% sodium thiosulfate and aqueous saturated NaHCO$_3$, 3 mL) and stirring continued for another 10 min. H$_2$O (2 mL) was added, the reaction mixture was extracted with hexane (3×5 mL), washed with brine, dried with Mg$_2$SO4 and the combined extracts were evaporated under reduced pressure. The residue was chromatographed (SiO$_2$, EtOAc-light petroleum, 1:99) to give the ketone (TDT) (283 mg, 89%); $R_f$(EtOAc-light petroleum, 2:8) 0.8; $\delta_H$(200 MHz; CDCl$_3$) 6.04 (s, 1H), 5.19-5.01 (m, 2H), 2.44-2.30 (m, 2H), 2.20-1.85 (m, 8H), 1.71 (s, 3H), 1.59 (s, 6H), 1.55 (s, 3H) and 1.38-1.17 (m, 19H); m/z (ESI)(Found: M+Na 383.3277, C$_{25}$H$_{44}$O requires M+Na 383.3284).

3,7,11-Trimethyl-dodeca-2,6,10-trienoic acid hexadecylamide (TDH): NaCN (31 mg) and MnO2 (590 mg) were added to a stirring solution of trans-trans-farnesol (100 mg, 0.45 mmol) in hexane (3 mL) at room temperature, followed by hexadecyl amine (545 mg, 2.2 mmol) and stirring continued for 1 h. An additional portion of MnO2 (590 mg) was added and the mixture left for overnight at room temperature with stirring. The mixture was then filtered through a pad of silica and celite and washed with hexane several times. The combined extracts were evaporated and the residue was chromatographed (SiO2, EtOAc-light petroleum, 3:97) to give 3,7,11-Trimethyl-dodeca-2,6,10-trienoic acid hexadecylamide ; m/z (ESI)(Found: M+Na 482.4334, C31H57ON requires M+Na 482.2332).

Fluorescence binding assays: RPE65 in PBS, 1% CHAPS, pH 7.4 was used in the fluorometric titration studies. All titrations were performed at 25° C. The samples in PBS buffer were excited at 280 nm and the fluorescence was scanned from 300 to 500 nm. Fluorescence measurements, using 450 µL quartz cuvettes with a 0.5 cm path length, were made at 25° C. on a Jobin Yvon Instruments, Fluoromax 2 employing the right-angle detection method.

The fluorescence of the protein solution was measured after equilibrating it at 25° C. for 10 min. The sample was then titrated with a solution of retinoid dissolved in DMSO in the absence of any overhead light and the solution was mixed thoroughly before fluorescence measurement. In each titration, to a 350 µL solution of the protein an equivalent amount of ligand, typically 0.3 µL, was added and thoroughly mixed before allowing it to equilibrate for 10 min prior to recording the fluorescence intensity. The addition of DMSO (0.1% per addition) did not have any effect on the fluorescence intensity. The binding constant ($K_D$) was calculated from the fluorescence intensity as described before (17,19).

Electroretinogram Determinations (ERG): Mice were dark-adapted overnight before all ERG experiments. To determine the acute effect of compounds under study, mice were given a single i.p. injection of a compound at 50 mg/kg in 25 µL DMSO under dim red light and kept in darkness for an additional 1 h before being exposed to the bleaching light prior to ERG recordings. Control ("untreated") animals were injected with 25 uL of DMSO. Mice were anaesthetized with ketamine (80 mg/kg) and xylazine (5-10 mg/kg) and pupils were dilated with 1% phenylephrine and 1% cyclopentolate, followed by an exposure to 5000 lux bleaching light for 2 min.

The ERG was recorded from the cornea with a cotton wick saline electrodes for about 50 min immediately after bleaching. Subcutaneous 30 gauge needles on the forehead and trunk were used as reference and ground electrodes, respectively. The animals rested on a heater maintaining the body temperature at 37° C. The light stimulus was obtained from a ganzfeld stimulator having a stroboscope (PS33 Grass Instruments Inc., West Warwick, R.I.) removed from its housing and recessed above and behind the head of the mouse. The flash was diffused to cover the ganzfeld homogeneously. Maximum flash intensity was measured with a calibrated light meter (J16 Tektronics Instruments, Beaverton, Oreg.). Responses were averaged by a Macintosh computer-controlled data acquisition system (PowerLab, AD Instruments, Mountain View, Calif.) at a frequency of 0.1 Hz. HCx The same animals were subjected to ERG experiments according to exactly the same protocol 3 days later, except no (repeated) injection of compounds was performed.

Tissue extraction and HPLC analysis: Posterior eye cups were pooled and homogenized in PBS using a tissue grinder. An equal volume of a mixture of chloroform/methanol (2:1) was added and the sample was extracted three times. To remove insoluble material, extracts were filtered through cotton and passed through a reversed phase (C18 Sep-Pak, Millipore) cartridge with 0.1% TFA in methanol. After removing solvent by evaporation under gas, the extract was dissolved in methanol containing 0.1% TFA, for HPLC analysis. For quantification of $A_2E$, a Waters Alliance 2695 HPLC was employed with a Atlantis® dC18 column (Waters, 4.6×150 mm, 3 µm) and the following gradient of acetonitrile in water (containing 0.1% trifluoroacetic acid): 90-100% (0-10 min), 100% acetonitrile (10-20 min), and a flow rate of 0.8 mL/min with monitoring at 430 nm. The injection volume was 10 µL. Extraction and injection for HPLC were performed under dim red light. Levels of $A_2E$ and iso-$A_2E$ were determined by reference to an external standard of HPLC-purified $A_2E$/iso-$A_2E$. Since $A_2E$ and iso-$A_2E$ reach photoequilibrium in vivo [4], use of the term $A_2E$ will refer to both isomers, unless stated otherwise.

Results

Figure 26A:
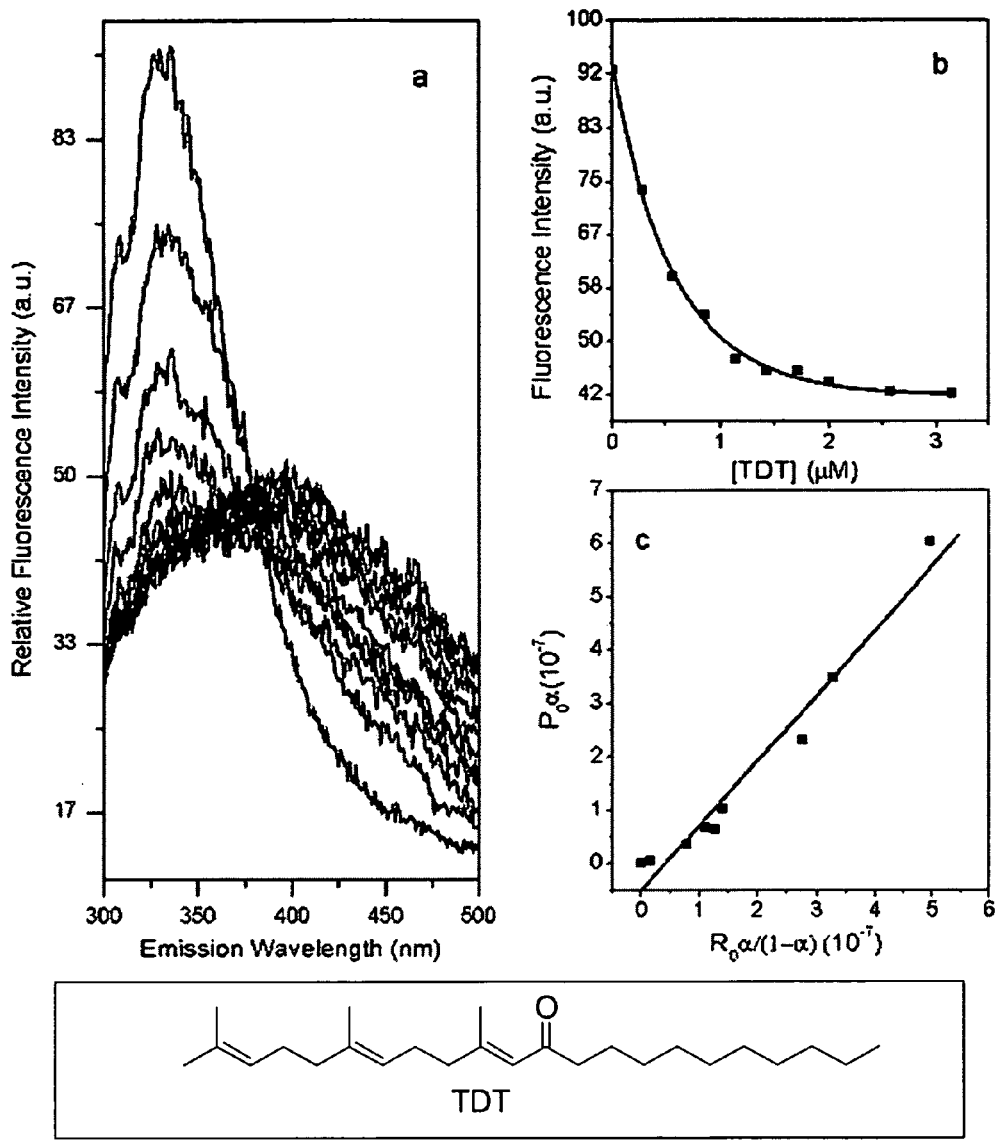
FIGS. 26A-B show that TDT (A) and TDH (B) bind to mRPE65 with high affinities.
Figure 26B:
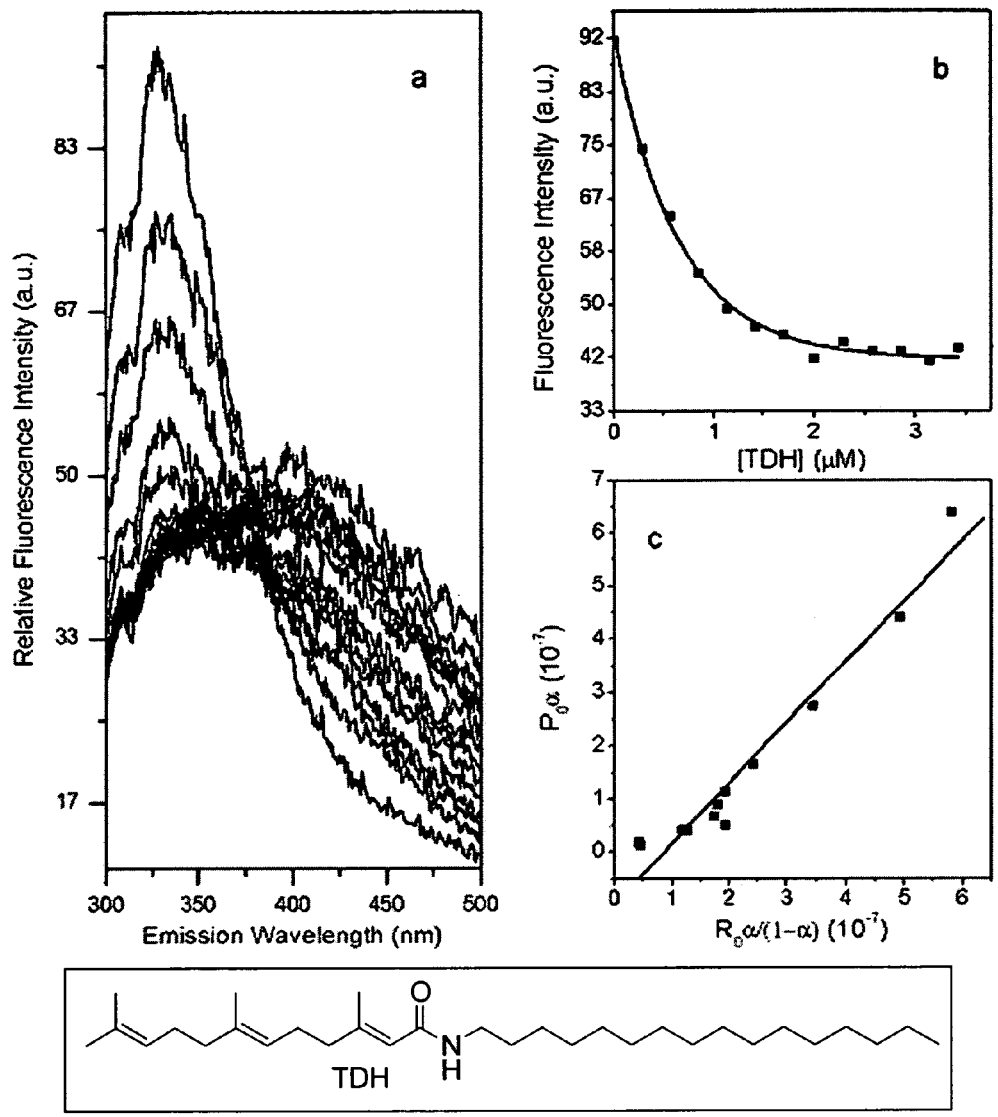

Design and In Vitro Activities of Specific mRPE65 Antagonists: In previous quantitative fluorescence studies we showed that mRPE65 saturably binds all-trans-retinyl palmitate (tRP) with a $K_D$=47 nM [17,19]. Further structure-activity studies on ligand binding to mRPE65 reveals that amide and ketone equivalents of tRP bound approximately as well as tRP itself [unpublished data]. Moreover, isoprenoids, such as C15 farnesyl, can substitute for the all-trans-retinyl moiety [unpublished data]. Based on these observations we prepared the trans,trans-farnesylated ketone (TDT) and amide (TDH) shown in FIGS. 26A-B. TDT and TDH specifically bind to purified bovine mRPE65 as shown by fluorescence titration of mRPE65 with TDT and TDH reported in FIGS. 26A-B. The excitation wavelength was at 280 nm and the emission was observed through 0.5 cm layer of solution. The titration solution consisted of 0.952 µM of mRPE65 in 100 mM phosphate buffered saline (150 mM NaCl) pH 7.4 and 1% CHAPS. Panel (a) of FIG. 26A shows the emission spectra of mRPE65 when binding to TDT. Panel (b) shows the change in the fluorescence intensity at 338 nm with increasing concentrations of TDT or TDH. Panel (c) shows the linear square fit plots of the equation $P_0\alpha$ vs $R_0\alpha/(1-\alpha)$, for the titration of mRPE65 vs. TDT or TDH [17, 19]. TDT binds with $K_D$=58±5 nM while TDH binds with $K_D$=96±14 nM. In these experiments, we made use of the fact that the specific binding of these analogs to mRPE65 quenches protein fluorescence.

In Vivo Studies with Analogs TDT and TDH

Acute effects: In order to determine whether TDT and TDH have an effect on the visual cycle in vivo, the overnight dark-adapted Abca4$^{+/+}$ (Rpe65 450Leu, pigmented, 129/SV× C57BL/6J) mice received single (i.p.) injections of the two compounds at 50 mg/kg. For comparison, mice were also injected with 13-cis-retinoic acid (13-RA; Accutane) at the same concentration. One hour after treatment, the mice were subjected to photo-bleaching (5000 lux for 2 min to bleach ~90% of rhodopsin) and ERGs were recorded.

Figure 27A:
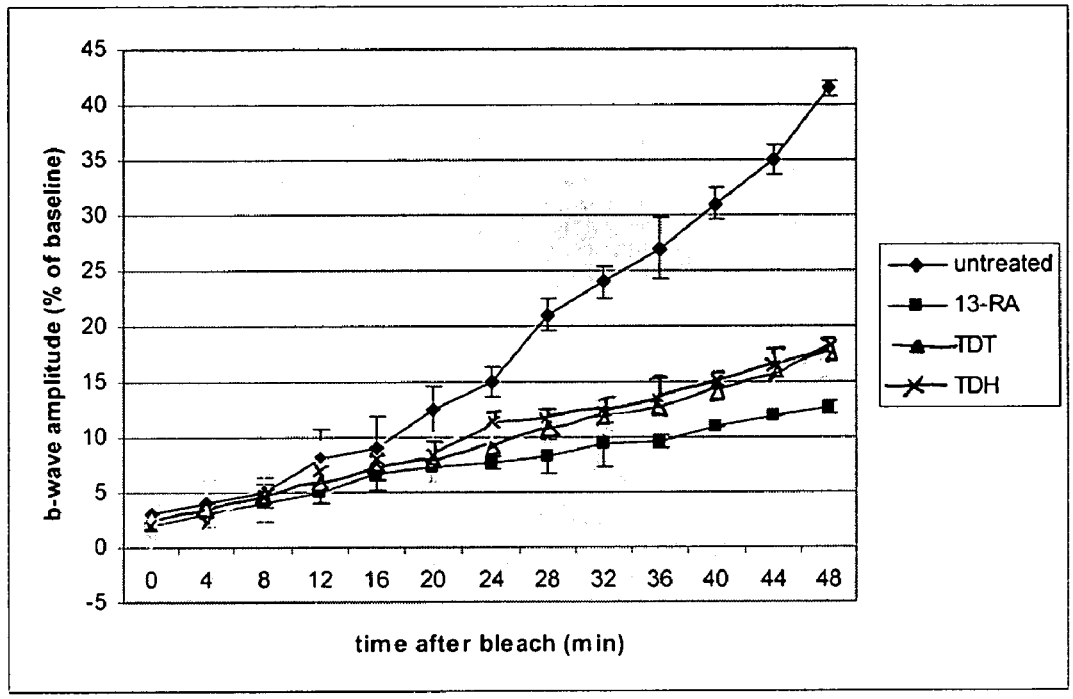
FIGS. 27A-B show ERG-b effects of TDT and TDH.
Figure 27B:
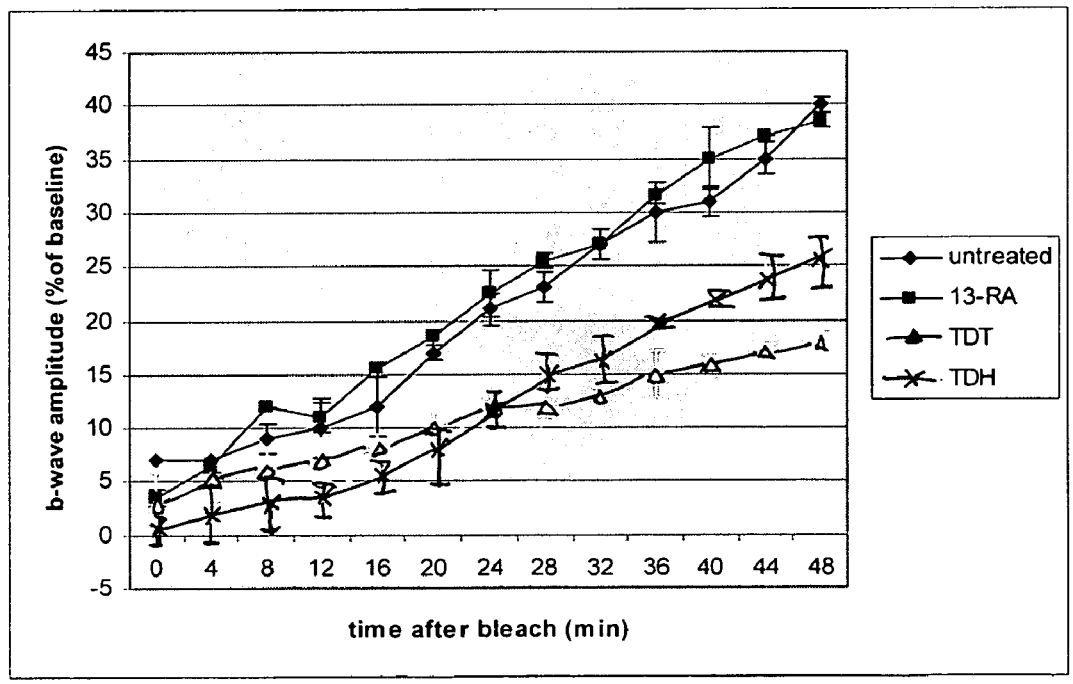

FIG. 27A shows the effects of TDT and TDH on the ERG b-wave amplitudes in animals 1 h after treatment with 50 mg/kg dose of three compounds (13-RA, TDT and TDH) on rod b-wave amplitude recovery after photo-bleaching. Results are averaged from three mice in each group with SD bars shown. Both isoprenoids delayed the recovery of dark-adapted visual responses to an extent similar to that of 13-RA as judged from dark-adapted ERG b-wave amplitudes recorded using dim light flashes delivered immediately before and at regular intervals after photo-bleaching. A substantial effect on rod b-wave recovery induced by TDT and TDH was still present 3 days after treatment while no sustained effect of 13-RA was detected (FIG. 27B).

To establish whether recovery of the dark-adapted rod b-wave was retarded because of an effect on 11-cis-retinal synthesis we studied the effects of TDT on 11-cis-retinal regeneration in rats and mice. The 11-cis-retinal that is regenerated is essentially all bound to rhodopsin in rodents, so that measuring its level is equivalent to measuring the rhodopsin content [27]. Initial experiments were performed on Sprague Dawley rats because similar experiments using 13-RA were previously carried out using these animals so that ready comparisons of potency and effectiveness can be made [24]. In these experiments, 13-RA was shown to exhibit profound effects on visual cycle function by interfering with 11-cis-retinal regeneration after a bleaching [24]. Accordingly, in the current experiments, the rats were given single injections (i.p.) of TDT (TDH) (50 mg/kg in DMSO), 13-RA (50 mg/kg in DMSO), and DMSO alone. After injecting the analogs, the rats were dark adapted for 2 h, and then exposed to light that led to <10% of dark adapted 11-cis-retinal in these animals, compared to dark adapted controls (data not shown). After allowing the bleached rats to dark-adapt again for 30 min, the animals were sacrificed, and the regenerated 11-cis-retinal was determined as indicated in Methods. In these experiments, the amount of resynthesized 11-cis-retinal, the chromophore of rhodopsin, is measured by HPLC and compared to the amounts of all-trans-retinyl ester precursor.

Figures 28A, 28B:
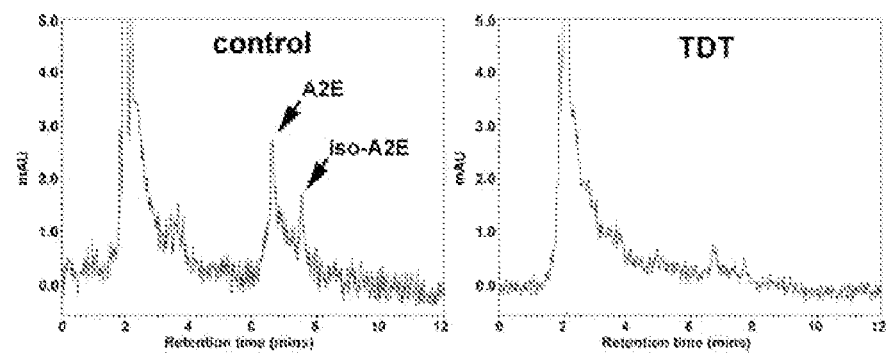
FIGS. 28A-D shows that certain isprenoid mRPE65 antagonists lower $A_2E$ accumulation.
Figures 28C, 28D:
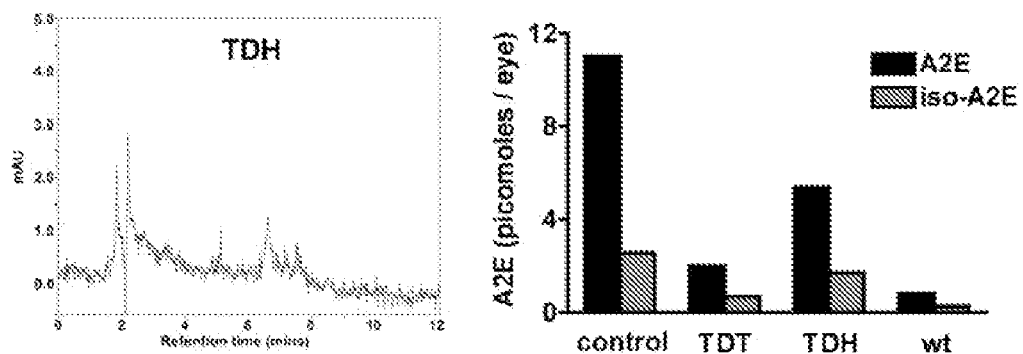

As shown in FIGS. 28A-C, both 13-RA (FIG. 28A) and TDT (FIG. 28B) achieved substantial (4-5-fold) inhibition of 11-cis-retinal regeneration, while the inhibitory effect of TDH (FIG. 28C) is less pronounced than with TDT. These figures show results of HPLC analysis of extracted retinoids from drug treated rats. FIG. 28A shows HPLC data from 13-RA treated Sprague Dawley rats. In FIG. 28A, the relative amounts of 11-cis-retinal-syn-oxime and all-trans-(cis)-retinyl esters are shown for the control (–13-RA) (top) and drug treated animals (bottom). In FIG. 28B, the corresponding data are shown for the TDT treated rats (top-control, bottom TDT treated). In this case, the ester pool in the drug treated rat is largely, if not exclusively, all-trans. FIG. 28C shows corresponding data for TDH treated rats (top-control, bottom TDH treated). These results are consistent with the observed lower potency of TDH as an mRPE65 antagonist compared to TDT. Upon repetition of the experiments two further times the average inhibition values are as follows: 13-RA (78±2%), TDT (79±4%), and TDH (55±2%). These percent inhibition values are generated by comparing the integrated areas under the retinyl ester and 11-cis-retinal-syn-oxime peaks. (Materials and Methods).

It is significant that the all-trans-retinyl ester pool increases at the expense of the 11-cis-retinal pool in the presence of TDT and TDH (FIGS. 28A-C). The concomitant increase in the all-trans-retinyl ester pool is expected of an antagonist of mRPE65. The magnitude of inhibition by 13-RA is approximately the same as reported [25]. In the case of 13-RA inhibition, the ester pool is a mixture of the 11-cis and all-trans isomers because of the inhibition of 11-cis-retinol-dehydrogenase [22, 25]. In the experiments described here with the isoprenoid antagonists, only all-trans-retinyl esters are detectable [data not shown].

Similar experiments with inhibitors were also performed in Balb/c mice. Here again inhibition is observed, but the effects are less pronounced than in rats, both with 13-RA and the isoprenoid antagonists. The inhibition values are as follows: 13-RA (33±4%), TDT (35±2%), and TDH (24±6%). It is noteworthy that in rats the 11-cis chromophore is regenerated considerably more slowly than in mice [27]. In mice, as in rats, the isoprenoid mRPE65 antagonists and 13-RA proved to be approximately equi-potent with respect to the inhibition of 11-cis-retinal regeneration.

b) Effect of the long-term (chronic) treatment of ABAC4$^{-/-}$ mice with TDT and TDH on A$_2$E accumulation: The RPE65 antagonists TDT and TDH were further tested for their abilities to reduce the accumulation of the RPE lipofuscin fluorophores A$_2$E and iso-A$_2$E. Beginning at 2 months of age, Abca4$^{-/-}$ mice (on the same genetic background as the Abca4$^{+/+}$ animals) were given i.p. injections of the two compounds at 50 mg/kg twice a week and A$_2$E and iso-A$_2$E levels were determined by quantitative HPLC after an additional 2 months.

As shown in FIGS. 29A-D, both compounds, but especially TDT, were highly efficient in lowering A$_2$E accumulation. FIGS. 29A-D show quantitation of A$_2$E and iso-A$_2$E in eye cups of Abcr –/– mice. (A-C) Typical chromatograms obtained by reverse-phase HPLC with monitoring at 430 nm illustrate the detection of A$_2$E and iso-A$_2$E and a reduction in peak intensity with TDT and TDH treatment relative to vehicle-treated controls. FIG>29D: A$_2$E/iso-A$_2$E quantitation from integrated peak areas normalized to external standards. Values expressed as picomoles per eye and are based on single samples obtained by pooling 4 eyes.

Specifically, the levels of A$_2$E in eyecups of mice treated with TDT were 85% lower than in vehicle-treated (DMSO) Abca4$^{-/-}$ animals. This is an under estimate of the extent of A$_2$E reduction because drug treatment did not commence until two months of age, and the data is not corrected for A$_2$E accumulation in the knockout mice up to this point. These results demonstrate that the mRPE65 antagonists TDT and TDH are effective in vivo and slow the rate of A$_2$E accumulation by limiting visual cycle function.

Discussion

RPE65 is of central importance in the operation of the visual cycle and been shown to be necessary for rhodopsin regeneration [15]. The retinoic acids specifically bind to mRPE65 and can block isomerization in RPE membranes [22]. The fact that 13-RA limits the visual cycle in rats in vivo [24] suggests the possibility that mRPE65 might be a viable target for interfering with toxic lipofuscin formation. In rats, the effects of 13-RA on visual function are pronounced. There is an approximately 4-fold inhibition measured for 11-cis-retinal regeneration after bleaching [24]. This inhibition is translated into a diminution in the accumulation of the lipofuscins in the A$_2$E series in the Abca4$^{-/-}$ knockout mouse model [25]. However, since the retinoic acids exhibit pleotropic effects, we undertook to prepare non-retinoid antagonists of mRPE65 to directly determine if inhibition of this target in and is of itself could limit the visual cycle, establish that RPE65 function is part of the rate-limiting step in visual pigment regeneration, and lessen the accumulation of the retinotoxic lipofuscins.

Two non-retinoid antagonists of mRPE65 were readily designed and shown to bind potently to mRPE65, a target unique to the visual cycle. Both TDT and TDH inhibited 11-cis-retinal regeneration after photobleaching to approximately the same extent as 13-RA. However unlike 13-RA, both TDT and TDH are directed solely at mRPE65, and in vivo inhibition results are consistent with this protein being the operant target. Rodents treated with TDT and TDH accumulate all-trans-retinyl esters behind the mRPE65 block. This result is expected, because the all-trans-retinyl esters are converted into 11-cis-retinol more slowly when mRPE65 is inhibited. By comparison, in the presence of 13-RA, the accumulation of both all-trans-retinyl and 11-cis-retinyl esters is noted [24]. This occurs because 13-RA inhibits both mRPE65 and 11-cis-retinol dehydrogenase [22,23].

Chronic treatment with TDT and TDH had profound effects on limiting A$_2$E accumulation in the animal model of STGD, the Abca4$^{-/-}$ mice. TDT, in particular, prevented A$_2$E formation by approximately 85% compared to untreated Abca4$^{-/-}$ animals, and brought A$_2$E levels down to approximately those observed in wt animals of similar age. The relationship between the extent of inhibition of visual cycle turnover and A$_2$E accumulation remains to be explored. It is likely to be non-linear, at least in part due to the fact that A$_2$E formation is second order in all-trans-retinal. Other non-linear effects may operate as well.

With respect to the pharmacology of the isoprenoid mRPE65 antagonists, it should be noted that the effects of both TDT and TDH are substantially more persistent than with 13-RA, probably because they are more hydrophobic than the retinoic acids. An increase in hydrophobicity tends to slow down rates of elimination of drugs. In addition, animals treated with TDT and TDH tolerated the compounds extremely well, showing no obvious signs of toxicity and/or distress, even when the compounds were administered every 48 h.

In conclusion, we have designed and studied specific, non-retinoid mRPE65 antagonists, which inhibit 11-cis-retinal regeneration after bleaching, further supporting the hypothesis that mRPE65 is minimally part of the rate-limiting process in visual pigment regeneration. The analogs described here will be useful in a chemical genetic approach to the temporal function of mRPE65 in visual cycle function visual pigment regeneration. Similar analogs will be used to probe the function of the congeneric sRPE65 as it relates to the regulation of the visual cycle [19]. In addition to analyzing the function of RPE65 in vitro, the non-retinoid antagonists also profoundly inhibited lipofuscin $A_2E$ accumulation in the Abca4$^{-/-}$ mouse model of macular degeneration. Our studies suggest that these, or similar molecules, may be efficient and non-toxic candidates as drugs aimed at preventing the onset of lipofuscin-sensitive forms of macular degeneration, including STGD and a prevalent form of AMD (geographic atrophy) leading to visual loss [28].

References Cited in Example 7

1). Lamb, T. D. & Pugh E. N., Jr. (2004) Dark adaptation and the retinoid cycle of vision. Prog. Retin. Eye Res. 23: 307-380.

2). Sakmar, T. P., Menon, S. T., Marin, E. P., & Awad, E. S. (2002) Rhodopsin: insights from recent structural studies. Ann. Rev. Biophys. and Biomolec. Struct. 31: 443-484.

3). Rattner, A., Smallwood, P. M., & Nathans, J. J. (2000) Identification and characterization of all-trans-retinol dehydrogenase from photoreceptor outer segments, the visual cycle enzyme that reduces all-trans-retinal to all-trans-retinol. J. Biol. Chem. 275: 11034-11043.

4). Parish, C. A., Hashimoto, M., Nakanishi, K., Dillon, J., & Sparrow, J. (1998) Isolation and one-step preparation of A2E and iso-A2E, fluorophores from human retinal pigment epithelium. Proc. of the Natl. Acad. of Sci. (U.S.A.) 95: 14609-14613.

5). Sparrow, J. R., Nakanishi, K., & Parish, C. A. (2000) The lipofuscin fluorophore A2E mediates blue light-induced damage to retinal pigmented epithelial cells. Invest. Ophthalmol. Vis. Sci. 41: 1981-1989.

6). Mata, N. L., Weng, J., & Travis, G. H. (2000) Biosynthesis of a major lipofuscin fluorophore in mice and humans with ABCR-mediated retinal and macular degeneration. Proc. Natl. Acad. Sci. U.S.A., 97: 7154-7159.

7). Fishkin, N. E., Sparrow, J. R., Allikments, R., & Nakanishi, K. (2005) Isolation and characterization of a retinal pigment epithelial cell fluorophore: An all-trans-retinal dimer conjugate. Proc. Natl. Acad. Sci. U.S.A., 10: 7091-7096.

8). Allikmets, R., Singh, N., Sun, H., Shroyer, N. F., Hutchinson, A., Chidambaram, A., Gerrard, B., Baird, L., Stauffer, D., Peiffer, A., et al. (1997) A photoreceptor cell-specific ATP-binding transporter gene (ABCR) is mutated in recessive Stargardt macular dystrophy. Nat Genet 15: 236-246.

9). Allikmets, R., Shroyer, N. F., Singh, N., Seddon, J. M., Lewis, R. A., Bernstein, P., Peiffer, A., Zabriskie, N., Li, Y., Hutchinson, A., et al. (1997b) Mutation of the Stargardt disease gene (ABCR) in age-related macular degeneration. Science 277: 1805-1807.

10). Allikmets, R. (2000a) Simple and complex ABCR: genetic predisposition to retinal disease. Am J Hum Genet 67: 793-799.

11). Beharry, S., Zhong, M., & Molday, R. S. (2004) N-retinylidene-phosphatidylethanolamine is the preferred retinoid substrate for the photoreceptor-specific ABC transporter ABCA4 (ABCR). J Biol Chem 279: 53972-53979.

12). Weng, J., Mata, N. L., Azarian, S. M., Tzekov, R. T., Birch, D. G., & Travis, G. H. (1999) Insights into the function of Rim protein in photoreceptors and etiology of Stargardt's disease from the phenotype in abcr knockout mice. Cell 98: 13-23.

13). Bavik, C. O., Eriksson, U., Allen, R. A., & Peterson, P. A. (1991) Identification and partial characterization of a retinal pigment epithelial membrane receptor for plasma retinol-binding protein. J. Biol. Chem. 266: 14978-14985.

14). Hamel, C. P., Tsilou, E. Harris, E., Pfeffer, B. A., Hooks, J. J., Detrick, B., & Redmond, T. M. (1993) A developmentally regulated microsomal protein specific for the pigment epithelium of the vertebrate retina. J. Neurosci. Sci. 34: 414-425.

15). Redmond, T. M., Yu, S., Lee, E., Bok, D., Hamasaki, D., Chen, N., Goletz, P., Ma, J. X., Crouch, R. K., & Pfeifer, K. (1998) RPE65 is necessary for production of 11-cis-vitamin A in the retinal visual cycle. Nat. Genet. 20: 344-351.

16). Jahng, W. J., David, C., Nesnas, N., Nakanishi, K., & Rando, R. R. (2003) A cleavable affinity biotinylating agent reveals a retinoid binding role for RPE65. Biochemistry 42:6159-6168.

17). Gollapalli, D. R., Maiti, P., & Rando, R. R. (2003) RPE65 operates in the vertebrate visual cycle by stereospecifically binding all-trans-retinyl esters. Biochemistry 42:11824-11830; erratum in: Biochemistry 43: 7226 (2003).

18). Mata, N. L., Moghrabi, W. N., Lee, J. S., Bui, T. V., Radu, R. A., Horwitz, J., & Travis, G. H. (2004) RPE65 is a retinyl ester binding protein that presents insoluble substrate to the isomerase in retinal pigment epithelial cells. J. Biol. Chem. 279:635-643.

19). Xue, L. Gollapalli, D. R., Maiti, P., Jahng, W. J., Rando, R. R. (2004) A palmitoylation switch mechanism in the regulation of the visual cycle. Cell 117: 761-771.

20). Kim, S. R., Fishkin, N., Kong, J., Nakanishi, K., Allikmets, R., & Sparrow, J. R. (2004) RPE65 Leu450Met variant is associated with reduced levels of the retinal pigment epithelium lipofuscin fluorophores A2E and iso A2E. Proc. Natl. Acad. Sci. USA 101: 11668-11672.

21). Lyubarsky, A. L. Savchenko, A. B., Morocco, S. B., Daniele, L. L., Redmond, T. M. and Pugh, E. N. (2005) Mole quantity of RPE65 and its productivity in the generation of 11-cis-retinal from retinal esters in the living mouse eye. Biochemistry 44: 9880-9888.

22). Gollapalli, D. R. and Rando, R. R. (2004) The specific binding of retinoic acid to RPE65 and approaches to the treatment of macular degeneration. Proc. Natl. Acad. Sci. U.S.A. 101, 10030-10035.

23). Law, W. C. & Rando, R. R. (1989) The molecular basis of retinoic acid induced night blindness. Biochem. Biophys. Res. Commun. 161: 825-829.

24). Sieving, P. A., Chaudhry, P., Kondo, M., Provenzano, M., Wu, D., Carlson, T. J., Bush, R. A., & Thompson, D. A. (2001) Inhibition of the visual cycle in vivo by 13-cis retinoic acid protects from light damage and provides a mechanism for night blindness in isotretinoin therapy. Proc. Natl. Acad. Sci. USA 98: 1835-1840.

25). Radu, R. A., Mata, N. L., Nusinowitz, S., Liu, X., Sieving P. A., & Travis, G. H. (2003) Treatment with isotretinoin inhibits lipofuscin accumulation in a mouse model of recessive Stargardt's macular degeneration. Proc. Natl Acad Sci USA 100: 4742-4747.

26). Guzzo, C. A., Lazarus, G. S., & Werth, V. P. (1996) in Goodman and Gilman's: The Pharmacological Basis of Therapeutics, 9$^{th}$ Ed, eds. Hardman, J. G. & Limbird, L. E. (McGraw Hill, New York), pp. 1598-1602.

27). Van Hooser, J. P., Garwin, G. G., & Saari J. C. (2000) Analysis of visual cycle in normal and transgenic mice. Methods in Enzymology, 316: 565-575.

28). Holz, F. G., Bellman, C., Staudt, S., Schmitt, F. and Volcker, H. E. (2001) Fundus autofluorescence and development of geographic atrophy in age-related macular degeneration. Invest. Ophthalmol. Vis, Sci. 42, 1051-1056.

29). Ma, J., Zhang, J., Othersen, K. L., Moiseyev, G., Ablonczy, Z., Redmond, T. M., Chen, Y., & Crouch, R. K. (2001) Expression, purification, and MALDI analysis of RPE65. Invest. Ophthalmol. Vis. Sci. 42: 1429-1435.

30). Lowry, O. H., Rosebrough, N. J., Farr, A. L., & Randall. R. J. (1951) Protein measurement with the folin phenol reagent. J. Biol. Chem., 193: 265-275.

31). Groenendijk, G. W. T., De Grip, W. J., & Daemen, F. J. M. (1980) Quantitative determination of retinals with complete retention of their geometric configuration. Biochim. Biophys. Acta 617: 430-438.

The examples should not be construed as limiting in any way. The contents of all cited references (including literature references, issued patents, published patent applications as cited throughout this application) are hereby expressly incorporated by reference.

Those skilled in the art will recognize, or be able to ascertain using no more than routine experimentation, many equivalents of the specific embodiments described herein.

The invention claimed is:

1. The compound of formula IV:

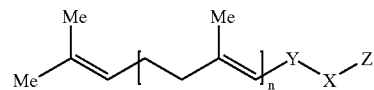

IV wherein,
n is 2;
Y is —C(=O)—;
X is —CH$_2$—; and
Z is —(CH$_2$)$_8$CH$_3$.